(12) United States Patent
Andres et al.

(10) Patent No.: US 11,787,819 B2
(45) Date of Patent: Oct. 17, 2023

(54) CRYSTALLINE SALT OF A MULTI-TYROSINE KINASE INHIBITOR, METHOD OF PREPARATION, AND USE THEREOF

(71) Applicant: Mirati Therapeutics, Inc., San Diego, CA (US)

(72) Inventors: Patricia Andres, Bend, OR (US); Ekaterina Albert, West Lafayette, IN (US); Emily Rigsbee, West Lafayette, IN (US); Zhiwei Cao, Basking Ridge, NJ (US); Dalian Zhao, Fanwood, NJ (US); Zhonghua Zhang, Ridgefield, CT (US)

(73) Assignee: MIRATI THERAPEPEUTICS, INC., San Diego, CA (US)

( * ) Notice: Subject to any disclaimer, the term of this patent is extended or adjusted under 35 U.S.C. 154(b) by 0 days.

(21) Appl. No.: 17/691,658

(22) Filed: Mar. 10, 2022

(65) Prior Publication Data
US 2022/0289760 A1    Sep. 15, 2022

Related U.S. Application Data

(60) Provisional application No. 63/159,417, filed on Mar. 10, 2021.

(51) Int. Cl.
  *C07D 495/04*    (2006.01)
  *A61P 35/00*    (2006.01)

(52) U.S. Cl.
  CPC ........ *C07D 495/04* (2013.01); *C07B 2200/13* (2013.01)

(58) Field of Classification Search
  CPC .............................. C07D 495/04; A61P 35/00
  See application file for complete search history.

*Primary Examiner* — Bruck Kifle
(74) *Attorney, Agent, or Firm* — WOOD PHILLIPS KATZ CLARK & MORTIMER

(57) ABSTRACT

The present invention relates to malate salt of a multi-tyrosine kinase inhibitor. In particular, the present invention relates to crystalline forms of the malate salt of multi-tyrosine kinase inhibitor N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1), pharmaceutical compositions comprising the crystalline form, processes for preparing the crystalline form and methods of use therefore.

28 Claims, 27 Drawing Sheets

CRYSTALLINE SALT OF A MULTI-TYROSINE KINASE INHIBITOR, METHOD OF PREPARATION, AND USE THEREOF

FIELD OF THE DISCLOSURE

Disclosed herein is a crystalline salt form of a multi-tyrosine kinase inhibitor. In particular, disclosed herein are crystalline forms of multi-tyrosine kinase inhibitor N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate, pharmaceutical compositions comprising the crystalline form, processes for preparing the crystalline form, and methods of use therefore.

BACKGROUND OF DISCLOSURE

N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (Compound 1 (sitravatinib), free base) is a multi-tyrosine kinase inhibitor with demonstrated potent inhibition of a closely related spectrum of tyrosine kinases, including RET, CBL, CHR4q12, DDR and Trk, which are key regulators of signaling pathways that lead to cell growth, survival and tumor progression.

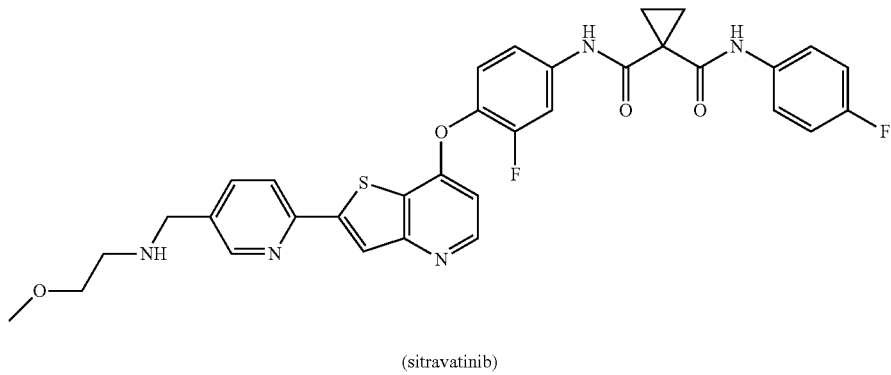

Compound 1

(sitravatinib)

Compound 1 shows tumor regression in multiple human xenograft tumor models in mice, and is presently in human clinical trials as a monotherapy as well as in combination for treating a wide range of solid tumors. Compound 1 is presently in Phase 2 clinical trial for patients with advanced cancer, advanced liposarcoma, and non-small cell lung cancer (NSCLC).

Compound 1 free base and the corresponding drug product exhibit poor long term stability at room temperature, thus requiring storage of the drug substance and drug product under refrigerated conditions. The identification and development of a solid form exhibiting enhanced stability, particularly at room temperature, is therefore of great interest to improve the commercial acceptability and commercial viability of Compound 1 as a drug candidate.

It is also well known in pharmaceutical industry that any improvement of bioavailability will have a positive economic impact for a company and also benefit our environment because less quantity of API will be needed and manufactured. Although forming a crystalline salt is sometimes a possible way to increase the solubility and dissolution rate of a drug, whether salt formation would increase or decrease bioavailability is not predictable and can only be found by manufacturing and testing in animals and humans.

In practice, it is difficult to predict which physical forms of a particular compound will be stable and suitable for pharmaceutical processing. It is even more difficult to predict whether a particular crystalline solid state form can be produced with the desired chemical and physical properties for pharmaceutical formulations.

For pharmaceutical applications, to ensure uniformity of the product, a single solid phase with good control over polymorphism is essential. Compound 1 possesses a high number of carbon-carbon, carbon-oxygen and carbon-nitrogen σ-bonds (13 in total), which can engage in rotational isomerism. In the solid state, extensive polymorphism or mixture between energetically similar rotational isomers may exist. Overcoming rotational isomerism by defining a robust, scalable process that reliably produces a single crystalline phase is a key hurdle to for development and commercialization of a drug candidate.

For all the foregoing reasons, there is a great need to find a crystalline forms of a salt of Compound 1 that provides enhanced dissolution rate, adequate bioavailability with little or no use of surfactants, acceptable stability/shelf life during storage at room temperature, and good manufacturability of the pharmaceutical composition. The present invention advantageously addresses one or more of these requirements.

SUMMARY OF THE INVENTION

The present disclosure addresses the foregoing challenges and need by providing a stable crystalline forms of a salt of Compound 1. Various salts produced by pharmaceutically acceptable salt-forming agents including citric acid, 1,2-ethanedisulfonic acid, hydrochloric acid, sulfuric acid, maleic acid, L-malic acid, succinic acid, L-tartaric acid, malonic acid, p-toluenesulfonic acid, p-toluic acid, and mandelic acid were investigated, as well as polymorphic screening of selected salts of interest for this purpose. Salts produced from these experiments were determined to be prone to forming a high number of solid materials, difficult to obtain as single crystalline non-solvated phases.

After extensive experimentation, the inventors have found a crystalline form of Compound 1 malate, which possesses superior physical and chemical properties suitable for pharmaceutical formulations and can be manufactured in large commercial scales with high quality as a single polymorphic crystalline phase and with good reproducibility.

In a first aspect, disclosed herein is a crystalline salt of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (hereinafter referred to as Compound 1), which is selected from malate salts, tartrate salts, succinate salts, citrate salts, 1,2-ethane-disulfonate salts, hydrochloride salts, sulfate salts, maleate, malonate, p-tosylate, p-toluate, and mandelate salts of Compound 1. In one embodiment, the salt is pharmaceutically acceptable.

The inventors found it was extremely difficult to reproducibly prepare a single phase of crystalline forms of a salt of Compound 1, including the L-malate salt, succinate salt, or L-tartrate salt, and most of the crystalline materials obtained were solvated, in some degree of disorder and/or composed of multi-phase forms. For example, the L-malate salt of Compound 1 can exist in various crystalline forms or materials, which are hereinafter referred to as Compound 1 bient temperature necessary for the drug product prepared from the free base. The increase in bioavailability was demonstrated in clinical trials where 20-30% dose reduction was achieved when the salt was dosed in patients, translating in bioequivalence between 100 mg capsules of Compound 1 Malate Form A and 120 mg capsules of Compound 1 Free Base.

In a second aspect, disclosed herein is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1), hereinafter referred to as a crystalline form of Compound 1 Malate (1:1).

In one embodiment, the crystalline form of Compound 1 Malate is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1), hereinafter referred to as a crystalline form of Compound 1 (S)-2-hydroxysuccinate (1:1) or Compound 1 L-Malate (1:1).

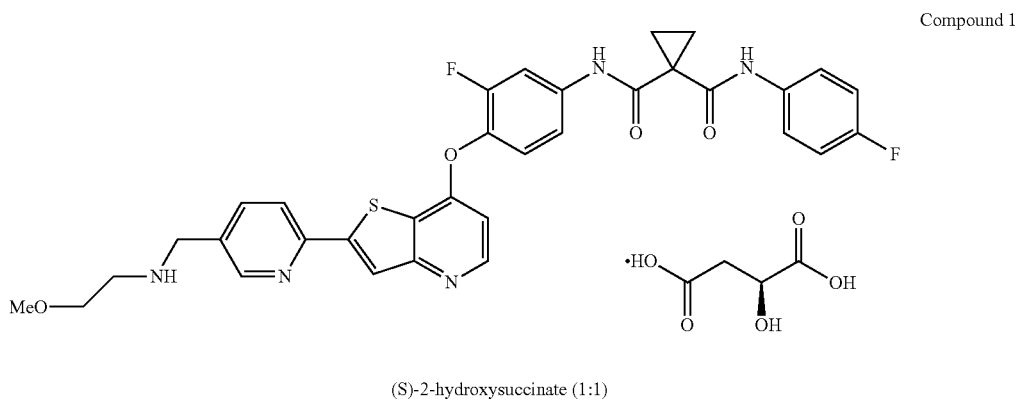

Compound 1

(S)-2-hydroxysuccinate (1:1)

Malate Form A (a single phase of crystalline forms, abbreviated as Malate Form A), Malate Material B, Malate Material C, Malate Material D, Malate Form E, Malate Material F, Malate Material G, Malate Material H, Malate Material J, Malate Material K, Malate Material L, Malate Material M, Malate Material N, Malate Material O, Malate Material P, Malate Material Q. The L-tartrate salt of Compound 1 can also exist in various crystalline forms or materials, which are hereinafter referred to as Tartrate Form A, Tartrate Material B, Tartrate Material C, Tartrate Material D, Tartrate Material E and Tartrate Material F.

Despite the many competing crystalline forms of the malate and tartrate salts of Compound 1, it was found that Compound 1 Malate Form A (abbreviated as Malate Form A) and Compound 1 Tartrate Form A (abbreviated as Tartrate Form A), could be produced reproducibly as single crystalline phases at large scale.

Additionally, the inventors discovered that Malate Form A demonstrated improved and unpredictable properties advantageous for pharmaceutical use, including increased long-term chemical/physical stability as well as improved bioavailability compared to the previously disclosed free base. The improvement in chemical stability in practice allows ambient temperature storage of the drug product prepared from the L-malate Form A, compared to subam- In one embodiment, the crystalline form of Compound 1 (S)-2-hydroxysuccinate (1:1), containing 0~3.0 moles of $H_2O$ per mole of Compound 1 (S)-2-hydroxysuccinate (1:1).

In one embodiment, the crystalline form has an X-ray powder diffraction pattern comprising a diffraction peak having °2θ angle values in the range of 9.4° to 10.2°.

In one embodiment, the crystalline form has an X-ray powder diffraction pattern (XRPD) furtherly comprising diffraction a peak having a °2θ angle value of 12.6±0.2°.

In one embodiment, the crystalline form of Compound 1 (S)-2-hydroxysuccinate (1:1) is designated as Malate Form A.

In one embodiment, Malate Form A has an XRPD pattern substantially as shown in FIG. 1A. And, Malate Form A has an XRPD pattern having peak diffraction angles substantially as shown in Table 1A.

In another embodiment, Malate Form A has an XRPD pattern substantially as shown in FIG. 2A(a) and FIG. 2A(b).

In another embodiment, Malate Form A is a variable hydrate with an XRPD pattern exhibiting substantial XRPD peak shifting upon heating and cooling or changes in relative humidity as shown in FIG. 2A(c) and FIG. 2A(d).

In one embodiment, Malate Form A has an X-ray powder diffraction pattern comprising a diffraction peak having a °2θ angle in the range of 9.4° to 10.2°.

In one embodiment, the crystalline form of Compound 1 (S)-2-hydroxysuccinate (1:1) is designated as Malate Form E.

In another embodiment, Malate Form E has an XRPD pattern substantially as shown in FIG. 2A(e).

In another embodiment, the crystalline forms of Compound 1 (S)-2-hydroxysuccinate (1:1) exhibiting XRPD patterns substantially as shown in FIG. 1A, FIG. 2A(a), FIG. 2A(b), FIG. 2A(c), FIG. 2A(d), and FIG. 2A(e).

In a third aspect, disclosed herein is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide tartrate (hereinafter referred to as Compound 1 Tartrate).

In one embodiment, the crystalline form of Compound 1 Tartrate is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide tartrate (1:1), hereinafter referred to as a crystalline form of Compound 1 Tartrate (1:1).

In one embodiment, the crystalline form of Compound 1 Tartrate is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (2R,3R)-2,3-dihydroxysuccinate (1:1), hereinafter referred to as a crystalline form of Compound 1 (2R,3R)-2,3-dihydroxysuccinate (1:1) or Compound 1 L-Tartrate (1:1).

In one embodiment, the crystalline form of Compound 1 (2R,3R)-2,3-dihydroxysuccinate (1:1) is designated as Tartrate Form A.

In another embodiment, Tartrate Form A has an XRPD pattern substantially as shown in FIG. 2B(a).

In one embodiment, the crystalline forms are at least 40%, 50%, 60%, 70%, 80%, 90% or 95% crystalline.

In a fourth aspect, disclosed herein is a pharmaceutical composition comprising a therapeutically effective amount of a salt of Compound 1, and pharmaceutically acceptable excipients. In one embodiment, the salt is selected from malate salts, tartrate salts, succinate salts, citrate salts, 1,2-ethanedisulfonate salts, hydrochloride salts, sulfate salts, maleate salts, malonate salts, p-tosylate salts, p-toluate salts, and mandelate salts of Compound 1. In one embodiment, the salt is pharmaceutically acceptable. In one preferred embodiment, the salt is in a crystalline form.

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1).

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide tartrate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (2R,3R)-2,3-dihydroxysuccinate (1:1).

In one embodiment, the salt is in a crystalline form of L-malate and L-tartrate, particularly Malate Form A, Malate Form E, and Tartrate Form A. In another embodiment, the salt is in a crystalline form, Malate Form A.

In a fifth aspect, disclosed herein is a method for inhibiting multi-tyrosine kinase activity in a cell, comprising contacting the cell in which inhibition of multi-tyrosine kinase activity is desired with a therapeutically effective amount of a pharmaceutically acceptable salt of Compound 1, and pharmaceutically acceptable excipients. In one embodiment, the salt is selected from malate salts, tartrate salts, succinate salts, citrate salts, 1,2-ethanedisulfonate salts, hydrochloride salts, sulfate salts, maleate salts, malonate salts, p-tosylate salts, p-toluate salts, and mandelate salts of Compound 1. In one embodiment, the salt is

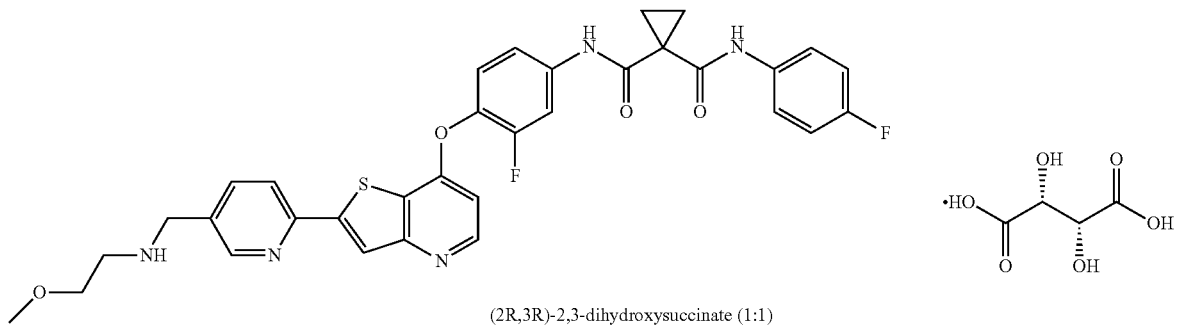

Compound 1

(2R,3R)-2,3-dihydroxysuccinate (1:1)

pharmaceutically acceptable. In one preferred embodiment, the salt is in a crystalline form.

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1).

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide tartrate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (2R,3R)-2,3-dihydroxysuccinate (1:1).

In one embodiment, the salt is in a crystalline form of L-malate and tartrate, particularly Malate Form A, Malate Form E, and Tartrate Form A. In another embodiment, the salt is in a crystalline form, Malate Form A.

In the sixth aspect, disclosed herein are a method of treating cancer in a subject in need thereof, comprising administering to the subject a therapeutically effective dose of a pharmaceutically acceptable salt of Compound 1, and pharmaceutically acceptable excipients.

In one embodiment, the salt is selected from malate salts, tartrate salts, succinate salts, citrate salts, 1,2-ethanedisulfonate salts, hydrochloride salts, sulfate salts, maleate salts, malonate salts, p-tosylate salts, p-toluate salts, and mandelate salts of Compound 1. In one embodiment, the salt is pharmaceutically acceptable. In one embodiment, the salt is pharmaceutically acceptable. In one preferred embodiment, the salt is a crystalline form.

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1).

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide tartrate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (2R,3R)-2,3-dihydroxysuccinate (1:1).

In one embodiment, the salt is in a crystalline form of L-malate and L-tartrate, particularly Malate Form A, Malate Form E, and Tartrate Form A. In another embodiment, the salt is in a crystalline form, Malate Form A.

In a seventh aspect, disclosed herein is a process for the preparation of a crystalline form of a salt of Compound 1. In one embodiment, the crystalline form is selected from Malate Form A and Tartrate Form A. In another embodiment, the crystalline form is Malate Form A.

BRIEF DESCRIPTION OF THE FIGURES

FIG. 2A(a) illustrates an indexing solution for X-ray powder diffraction (XRPD) pattern of Crystalline Form A of Compound 1 malate (Malate Form A) prepared according to Example 2.

FIG. 2A(b) illustrates an indexing solution for X-ray powder diffraction (XRPD) pattern of Crystalline Form A of Compound 1 malate (Malate Form A) shifted, prepared according to Example 2.

FIG. 2A(c) illustrates Variable Temperature X-ray powder diffraction (VT-XRPD) pattern shifting for Compound 1 Malate Form A upon heating and cooling.

FIG. 2A(d) illustrates Variable Relative Humidity X-ray powder diffraction (VRH-XRPD) pattern shifting for Compound 1 Malate Form A upon variations in relative humidity.

FIG. 2A(e) illustrates an indexing solution for X-ray powder diffraction (XRPD) pattern of Crystalline Form E of Compound 1 malate (Malate Form E) prepared according to Example 2.

FIG. 2B(a) illustrates an indexing solution for X-ray powder diffraction (XRPD) pattern of Crystalline Form of Compound 1 tartrate (Tartrate Form A), prepared according to Example 2.

FIG. 2B(b) illustrates an indexing solution for X-ray powder diffraction (XRPD) pattern of Crystalline Form of Compound 1 tartrate (Tartrate Form A) shifted, prepared according to Example 2.

DETAILED DESCRIPTION OF THE DISCLOSURE

Figure 1A:
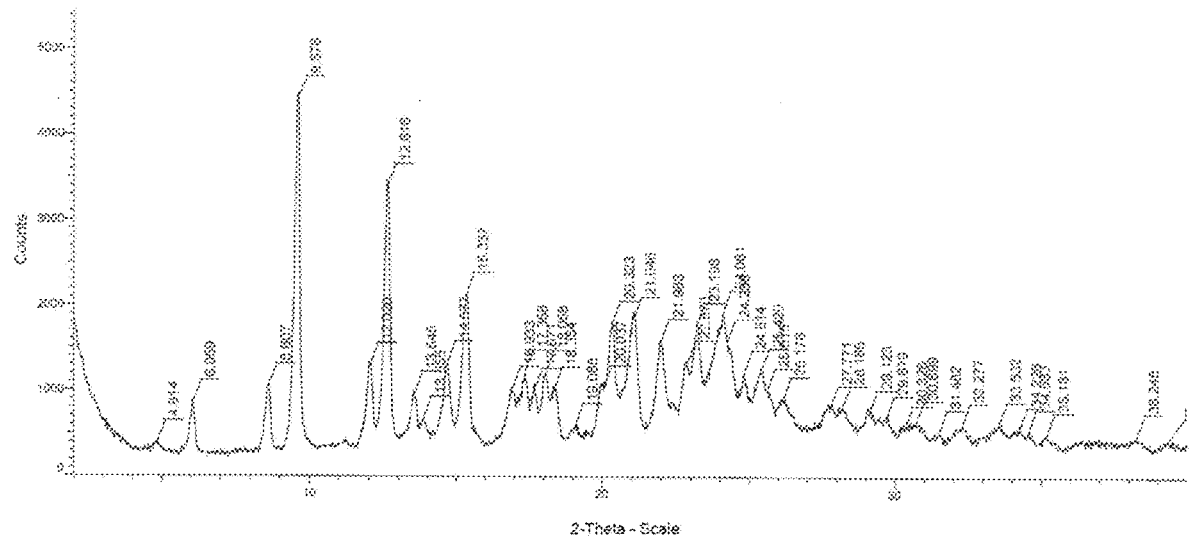
FIG. 1A illustrates an X-ray powder diffraction (XRPD) pattern of Crystalline Form A of Compound 1 malate (Malate Form A) prepared according to Example 1B.

The present disclosure relates to a salt of Compound 1. In particular, disclosed herein is a crystalline form of a Compound 1 salt, a pharmaceutical composition comprising the crystalline form, a process for preparing the crystalline form and a method of use thereof.

In a first aspect, disclosed herein is a salt of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (Compound 1), which is selected form malate salts, tartrate salts, succinate salts, citrate salts, 1,2-ethanedisulfonate salts, hydrochloride salts, sulfate salts, maleate salts, malonate salts, p-tosylate salts, p-toluate salts, and mandelate salts of Compound 1. In one embodiment, the salt is pharmaceutically acceptable. In one preferred embodiment, the salt is in a crystalline form.

Also, the inventors found it was extremely difficult to reproducibly prepare a single phase of crystalline forms of the malate salt or tartrate salt, and most of the crystalline materials obtained were in some degree of disorder, composed of multi-phase forms, or were solvated materials. For example, the L-malate salt of Compound 1 can exist in various crystalline forms or materials, which are hereinafter referred to as Compound 1 Malate Form A (a single phase of crystalline forms, abbreviated as Malate Form A), Malate Material B, Malate Material C, Malate Material D, Malate Form E, Malate Material F, Malate Material G, Malate Material H, Malate Material J, Malate Material K, Malate Material L, Malate Material M, Malate Material N, Malate Material O, Malate Material P, and Malate Material Q. The L-tartrate salt of Compound 1 can also exist in various crystalline forms or materials, which are hereinafter referred to as Tartrate Form A, Tartrate Material B, Tartrate Material C, Tartrate Material D, Tartrate Material E and Tartrate Material F.

In spite of the extremely complex polymorph landscape of salts of Compound 1, the isolation of the Malate Form A was found to be possible reproducibly under well-controlled crystallization conditions and is suitable for the manufacture of a uniform pharmaceutical product. Additionally, while other crystalline forms were obtained as solvated forms with a solvent other than water or obtained as mixtures, L-malate Form A was found to be manufacturable at large scale as a single crystalline phase substantially free of solvent other than water.

Moreover, Malate Form A is a variable hydrate which demonstrates unpredictable properties, such as good stability. The increased long-term chemical stability of the Malate Form A enables room temperature storage of the formulated drug product prepared with the malate salt, as opposed to the formulated drug product containing sitravatinib free base which necessitates refrigerated storage. The Malate Form A was also discovered to be physically the most stable form of the Malate salt of Compound 1 above ~23% RH at ambient temperature, and physically stable when exposed to 40° C./75% RH and 30° C./60% RH. While remaining the same form under these conditions, Malate Form A appeared to be a variable hydrate with a water content dependent on the relative humidity and temperature. Upon exposure to 30% and 93% RH for over ~4 days, Malate Form A was found to contain 3.7% and 5.3% of water, respectively (equivalent to ~1.5 and ~2.5 mol). Outside of the specified physical stability RH and temperature ranges, Malate Form A was observed to reversibly dehydrate to a suspected anhydrous but likely unstable material or lower hydrate (designated Malate Materials B, C and D). Of these materials, Malate Material D was further characterized by DVS and Karl Fischer, which confirmed its low water content (~0.67%, equivalent to ~0.3 mol).

Additionally, Malate Form A was also discovered to have superior properties compared to the free base, particularly increased long-term chemical/physical stability and greater bioavailability. The bioavailability of Malate Form A in dogs was shown to be improved dramatically as compared with the free base. The increase of bioavailability has also been demonstrated in clinical trials where 20-30% dose reduction is achieved for RP2D when drug product from the salt is dosed in patients.

In a second aspect, disclosed herein is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1), hereinafter referred to as a crystalline form of Compound 1 Malate (1:1).

In one embodiment, the crystalline form of Compound 1 Malate is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1), hereinafter referred to as a crystalline form of Compound 1 (S)-2-hydroxysuccinate (1:1) or Compound 1 L-Malate (1:1).

In one embodiment, the crystalline form of Compound 1 (S)-2-hydroxysuccinate (1:1) comprising 0~3 mol $H_2O$.

In one embodiment, the crystalline form has an X-ray powder diffraction pattern comprising a diffraction peak having °2θ angle values in the range of 9.4° to 10.2°.

In one embodiment, the crystalline form has an X-ray powder diffraction pattern comprising a diffraction peak having °2θ angle values in the range of 9.6±0.2°.

In another embodiment, the crystalline form has an X-ray powder diffraction pattern (XRPD) furtherly comprising diffraction a peak having a °2θ angle value of 12.6±0.2°.

In another embodiment, the crystalline form has an X-ray powder diffraction pattern (XRPD) furtherly comprising diffraction a peak having a °2θ angle value independently selected from the group consisting of 15.3±0.2°, 20.3±0.2°, 21.0±0.2° and 24.1±0.2°.

In another embodiment, the crystalline form has an X-ray powder diffraction pattern (XRPD) furtherly comprising diffraction a peak having a °2θ angle value independently selected from the group consisting of 12.0±0.2°, 15.3±0.2°, 20.3±0.2°, 21.0±0.2°, 22.0±0.2°, 23.2±0.2°, 24.1±0.2°, and 24.2±0.2°.

In another embodiment, the crystalline form has an X-ray powder diffraction pattern (XRPD) furtherly comprising diffraction a peak having a °2θ angle value independently selected from the group consisting of 6.1±0.2°, 8.6±0.2°, 12.0±0.2°, 13.5±0.2°, 15.3±0.2°, 16.9±0.2°, 17.4±0.2°, 17.7±0.2°, 18.1±0.2°, 18.4±0.2°, 20.0±0.2°, 20.3±0.2°, 21.0±0.2°, 22.0±0.2°, 22.9±0.2°, 23.2±0.2°, 24.1±0.2°, 24.2±0.2°, 24.8±0.2° and 25.4±0.2°.

In another embodiment, the crystalline form has an X-ray powder diffraction pattern (XRPD) furtherly comprising diffraction a peak having a °2θ angle value independently selected from the group consisting of 6.1±0.2°, 8.6±0.2°, 12.0±0.2°, 13.5±0.2°, 15.3±0.2°, 16.9±0.2°, 17.4±0.2°, 17.7±0.2°, 18.1±0.2°, 18.4±0.2°, 20.0±0.2°, 20.3±0.2°, 21.0±0.2°, 22.0±0.2°, 22.9±0.2°, 23.2±0.2°, 24.1±0.2°, 24.2±0.2°, 24.8±0.2°, 25.4±0.2°, 25.6±0.2°, 26.2±0.2°, 27.8±0.2°, 28.2±0.2° and 29.1±0.2°.

In one embodiment, the crystalline form of Compound 1 (S)-2-hydroxysuccinate (1:1) is designated as Malate Form A.

In one embodiment, Malate Form A has an XRPD pattern substantially as shown in FIG. 1A and Malate Form A has an XRPD pattern typically having following peak diffraction angles shown in Table 1A, below.

Figure 1B:
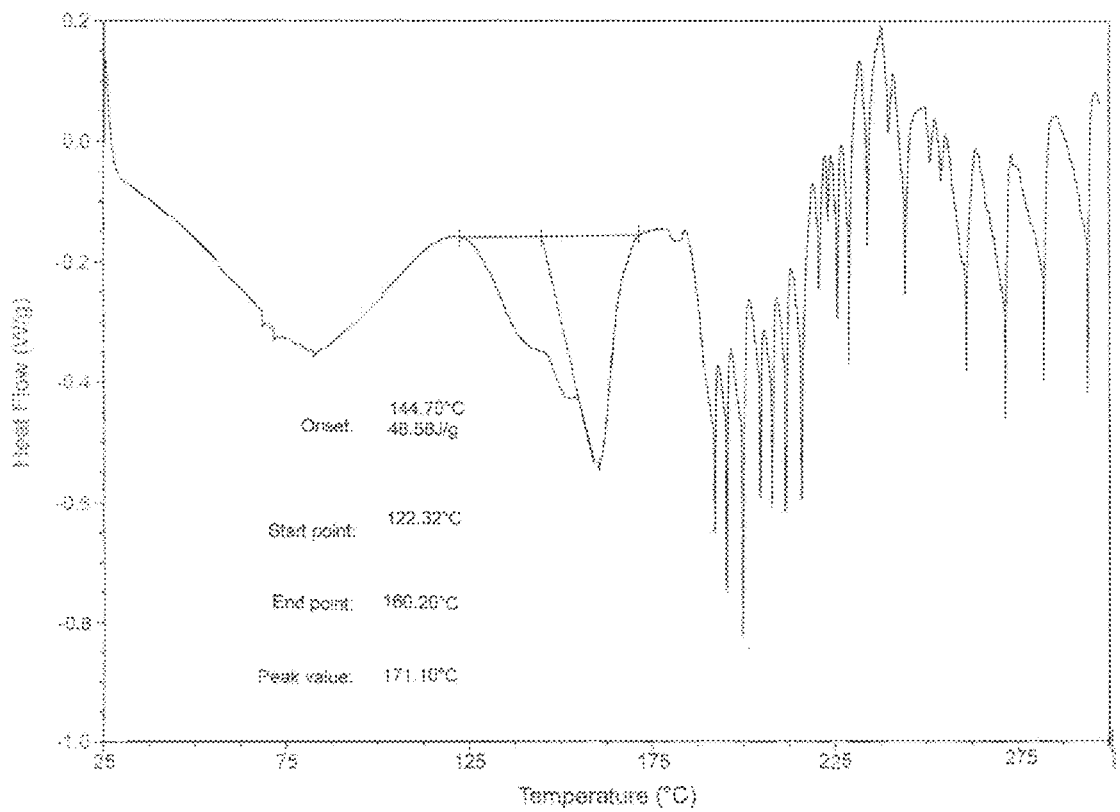
FIG. 1B illustrates a differential scanning calorimetry (DSC) profile of Crystalline Form A of Compound 1 malate (Malate Form A) prepared according to Example 1.

In another embodiment, Malate Form A is characterized by having a broad endothermic event between about 50-125° C. and overlapping endothermic events with a peak maximum at about 171° C. by differential scanning calorimetry ("DSC"). In another embodiment, Malate Form A has a DSC thermogram substantially as shown in FIG. 1B.

Figure 1C:
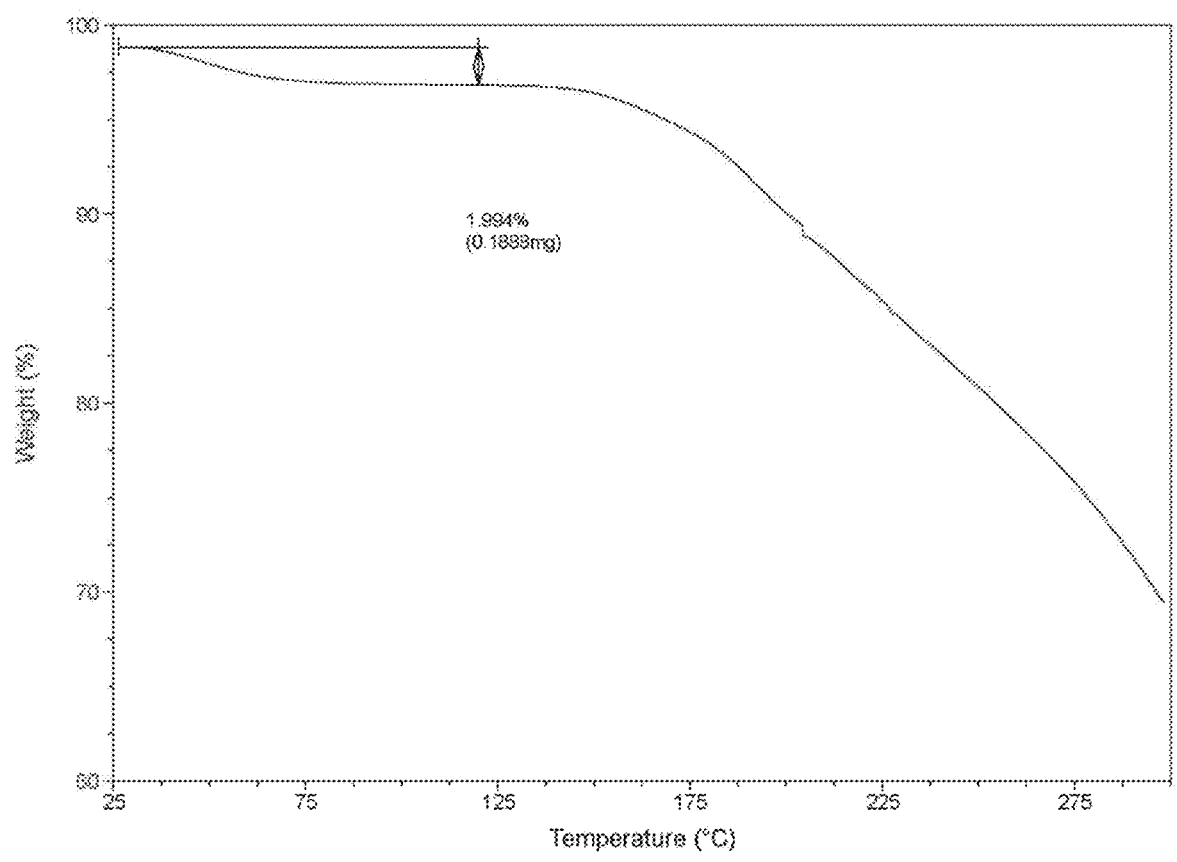
FIG. 1C illustrates a thermogravimetric analysis (TGA) profile of Crystalline Form A of Compound 1 malate (Malate Form A) prepared according to Example 1.

In one embodiment, Malate Form A is characterized by having a weight loss at 120° C. by thermogravimetric analysis ("TGA"). In another embodiment Malate Form A has a TGA profile substantially as shown in FIG. 1C.

Figure 1D:
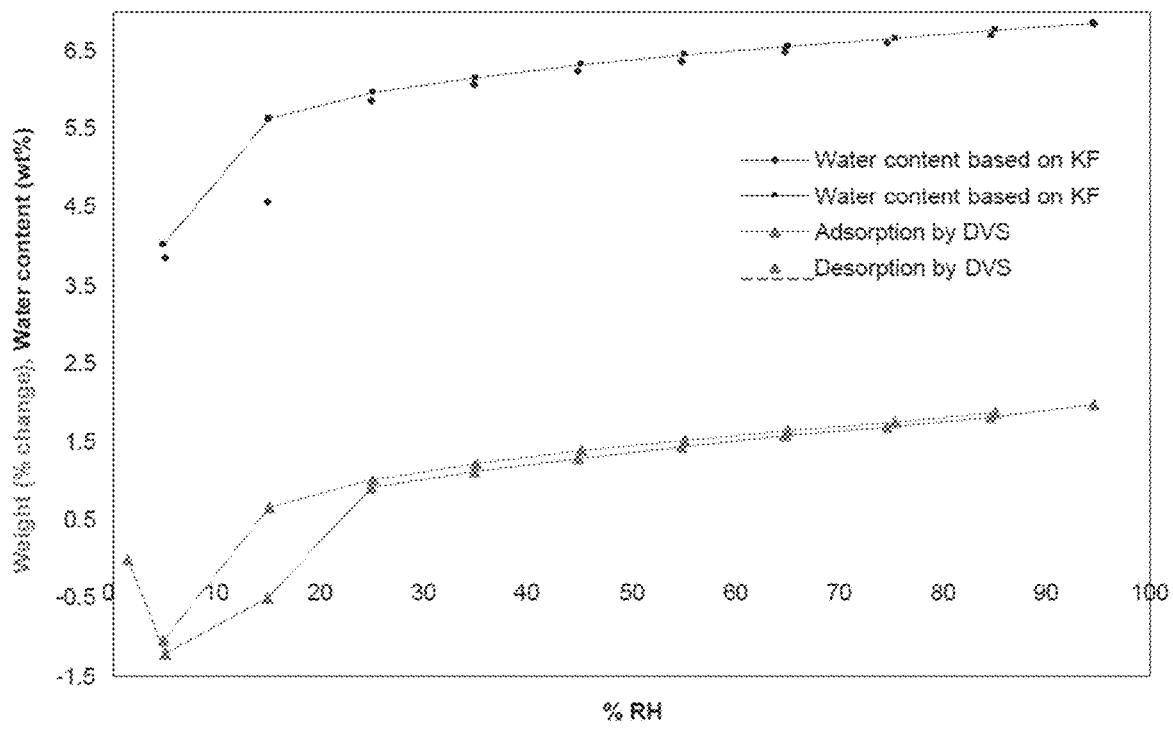
FIG. 1D illustrates a dynamic vapor sorption (DVS) isotherm profile of Crystalline Form A of Compound 1 malate (Malate Form A) prepared according to Example 1.

In one embodiment, Malate Form A is characterized by having a weight loss of about 1.2 wt % upon equilibration at 5% relative humidity (RH), a weight gain of about 2.1 wt % between 5-25% RH and additional 1.1 wt % gain between 25-95% during the sorption phase. During the desorption cycle, the material loses approximately 1.3 wt % and 1.7% in the 95-15% RH and 15-5% RH, respectively, with minimal hysteresis between ~25% and 5% RH, as determined by dynamic vapor sorption ("DVS"). In another embodiment, Malate Form A has a DVS isotherm substantially as shown in FIG. 1D.

Malate Form A was determined to be a variable hydrate, exhibiting an X-ray powder diffraction pattern comprising a shifted diffraction peak having °2θ angle values in the range of 9.4° to 10.2°.

Figure 2A:
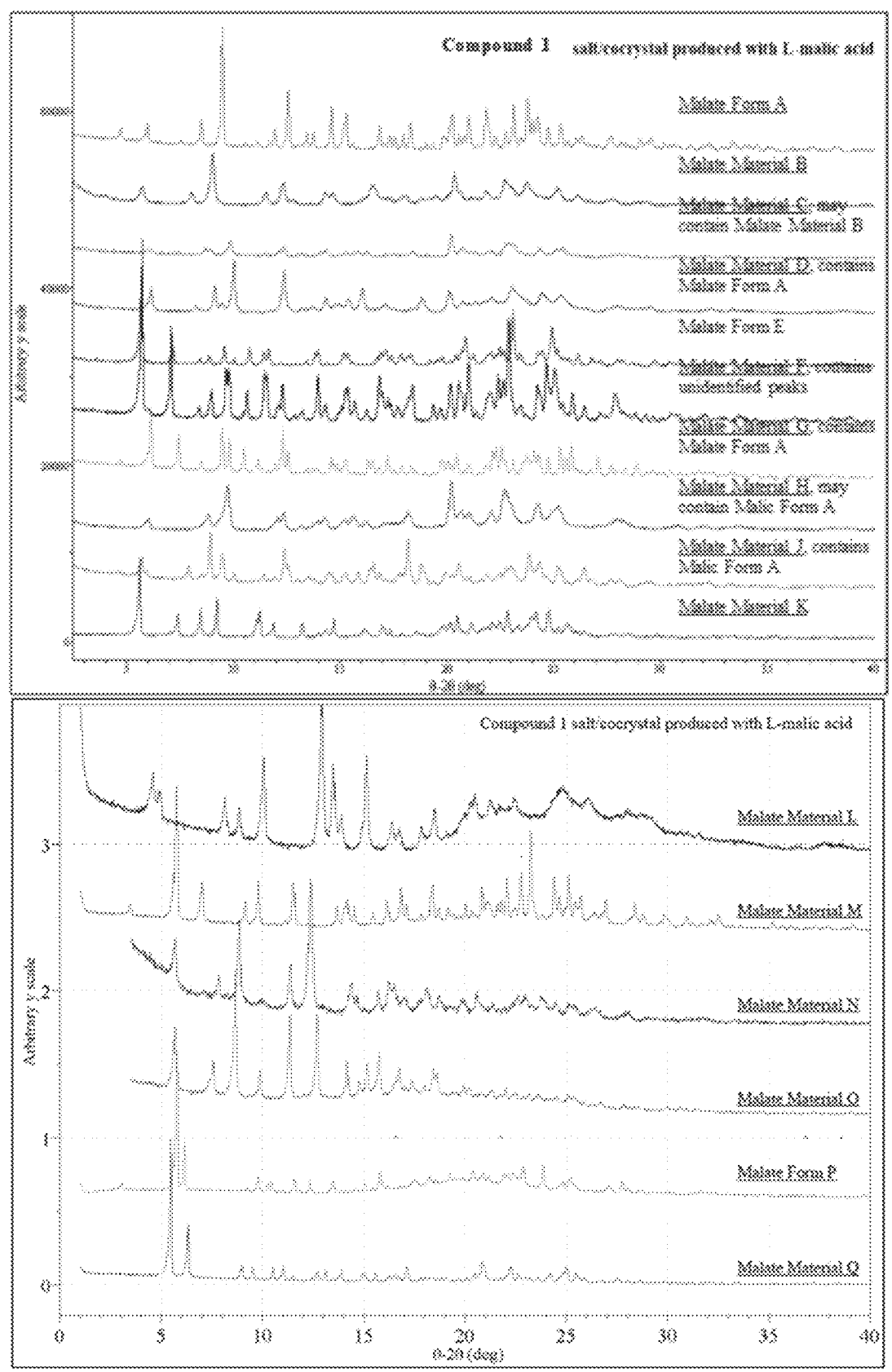
FIG. 2A illustrates X-ray powder diffraction (XRPD) patterns of Compound 1 salt/cocrystal produced with L-malic acid, prepared according to Example 2.
Figure 2A:
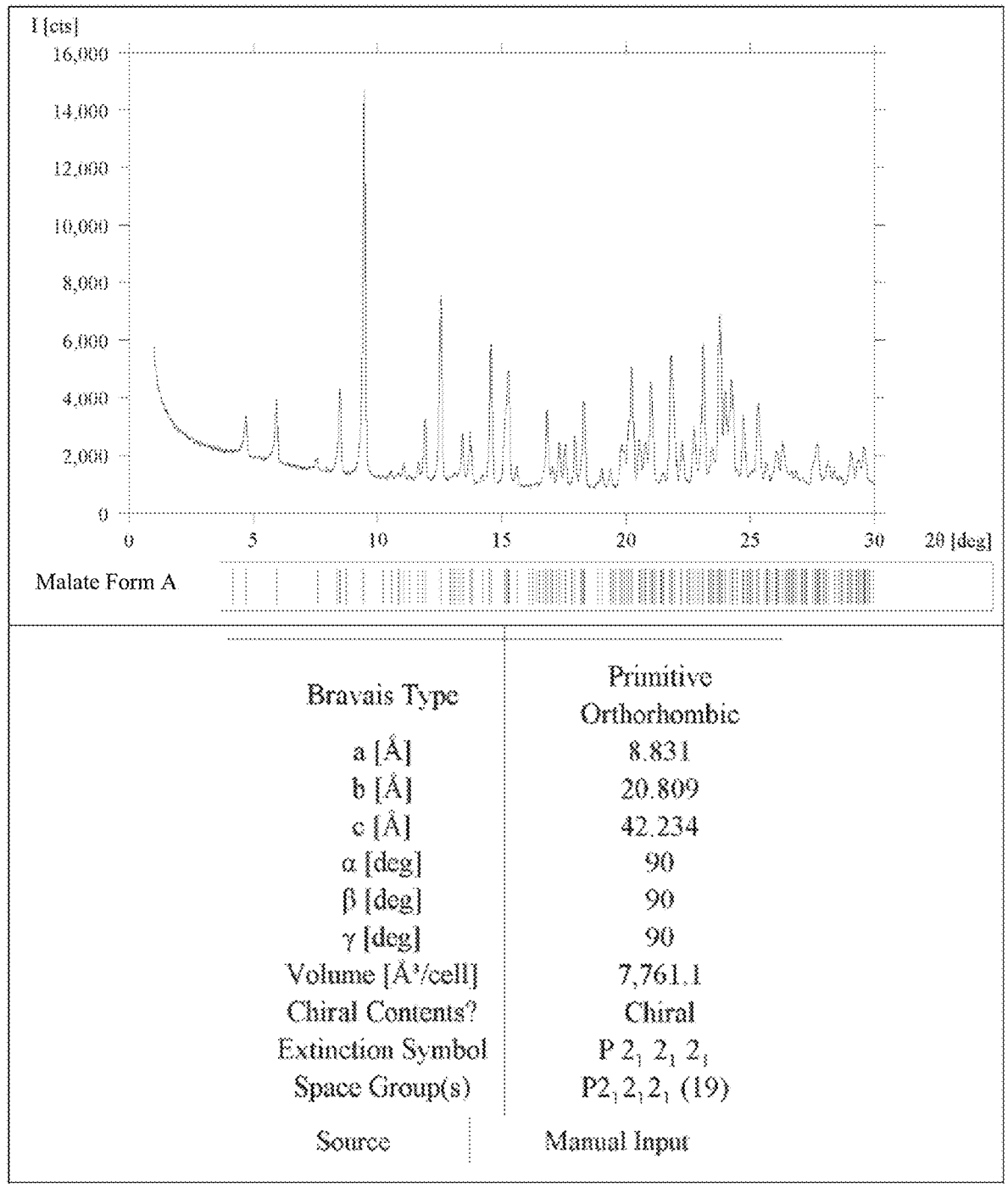
Figure 2A:
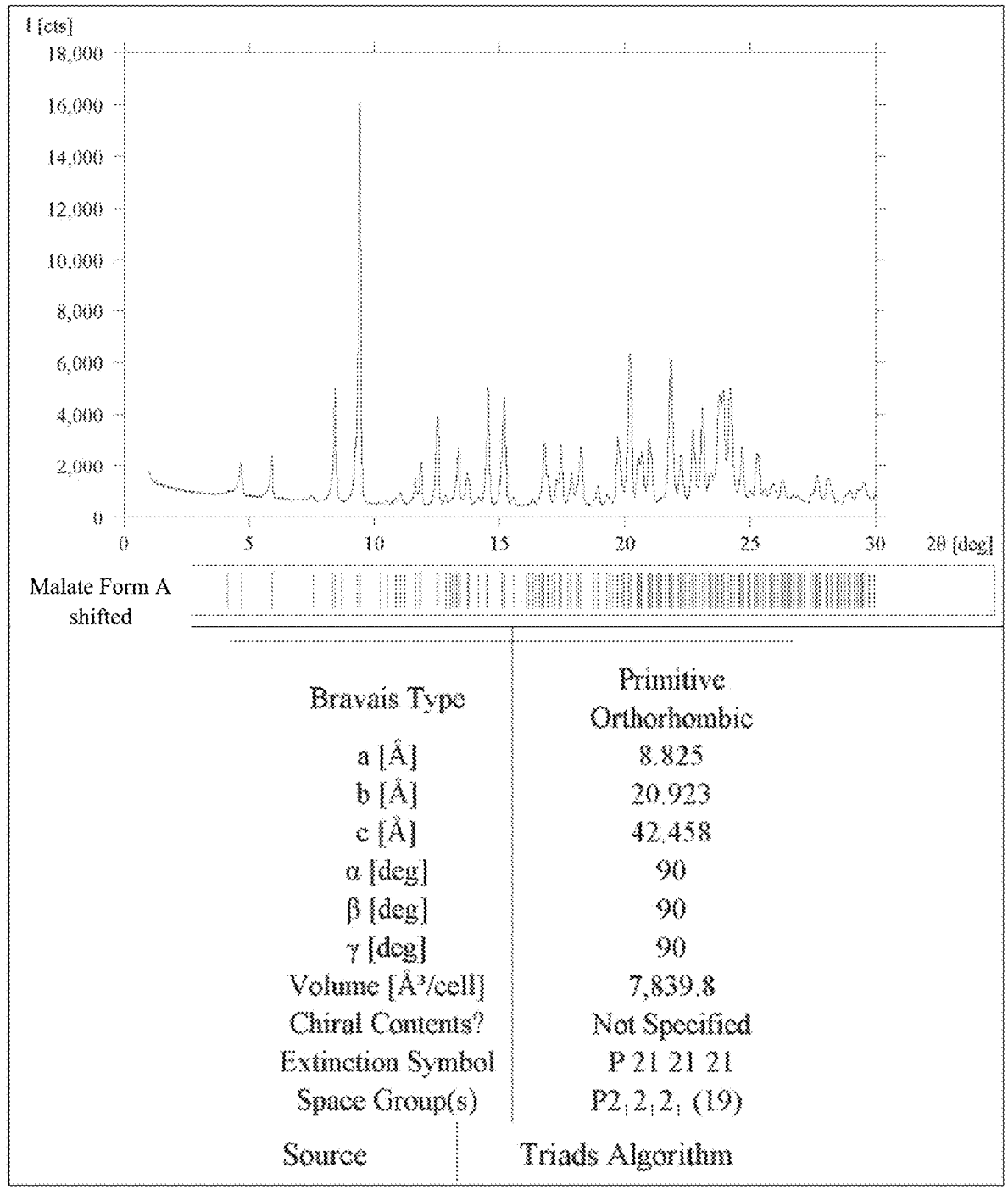
Figure 2A:
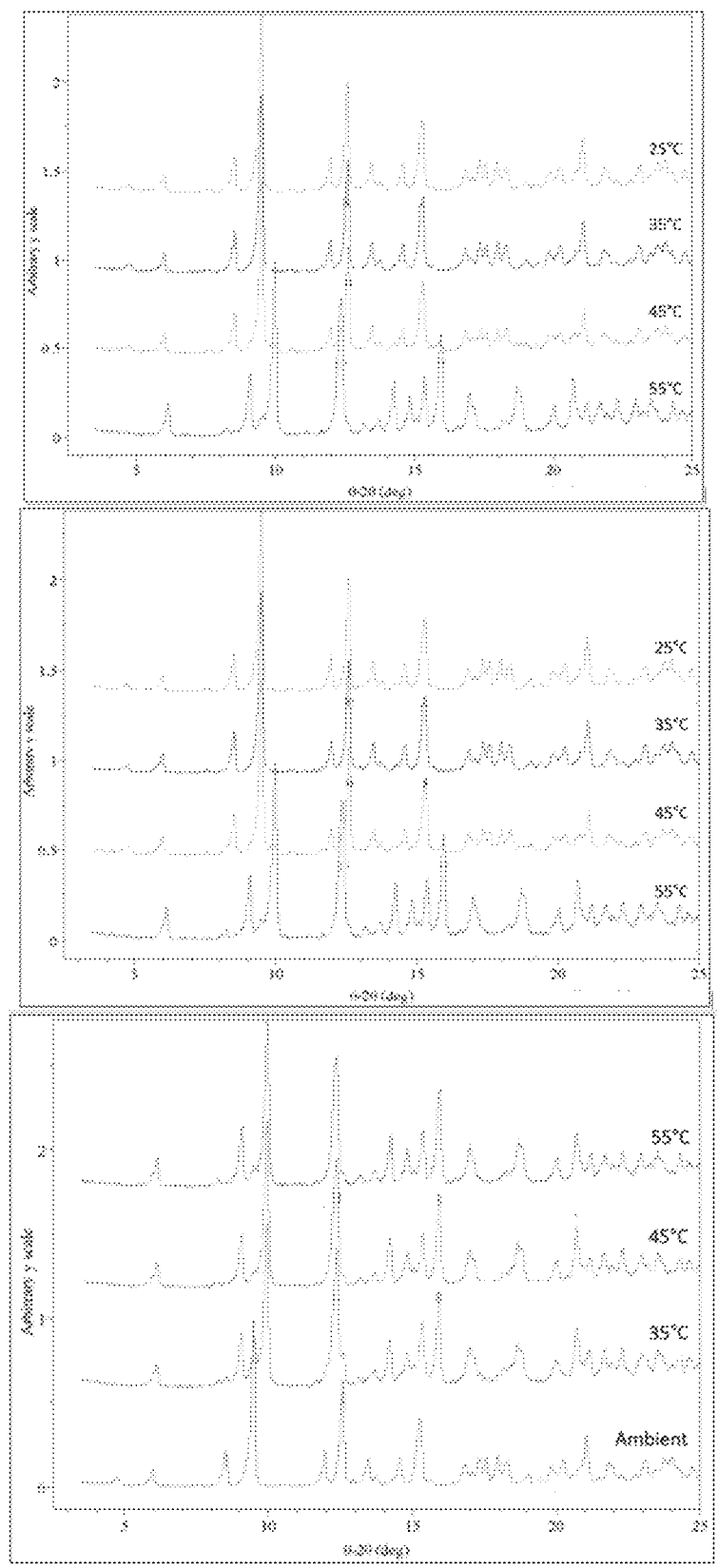
Figure 2A:
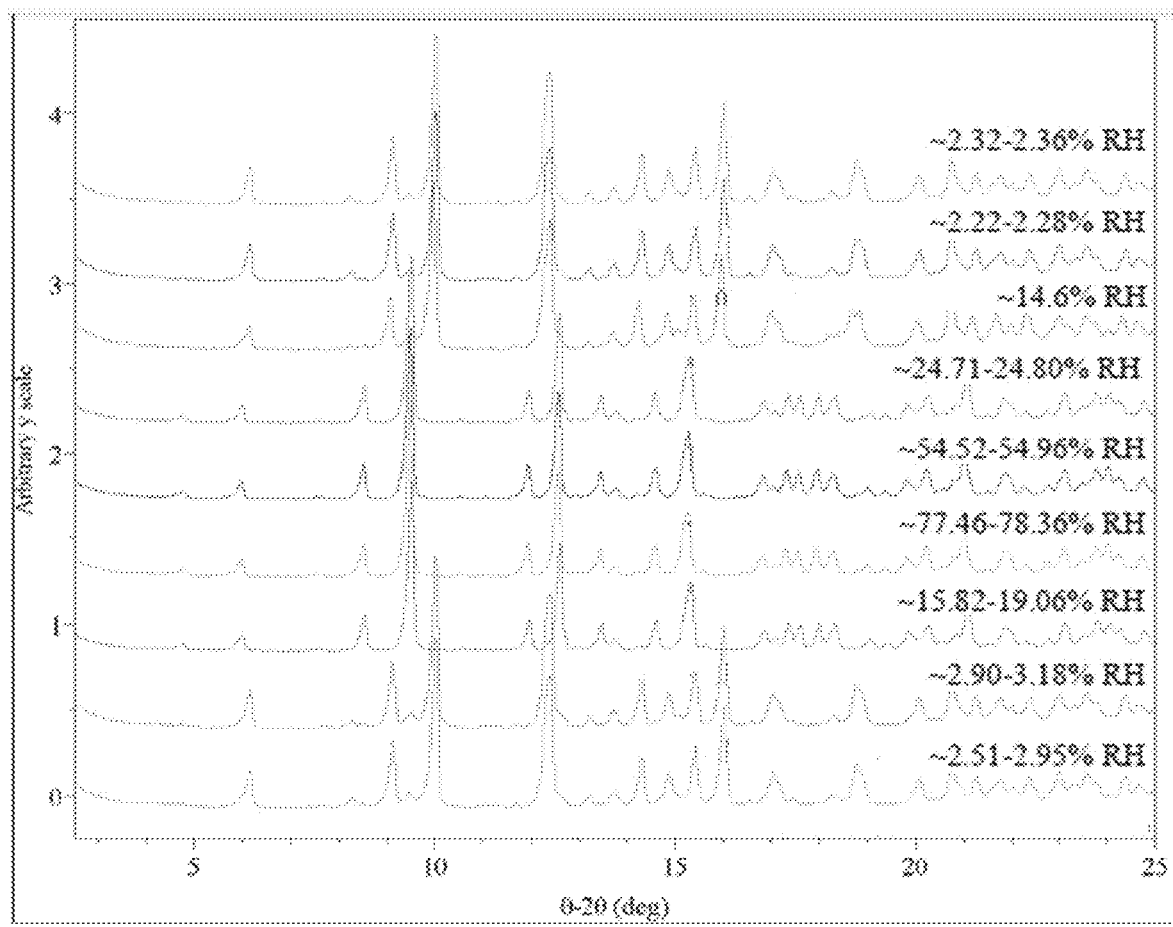
Figure 2A:
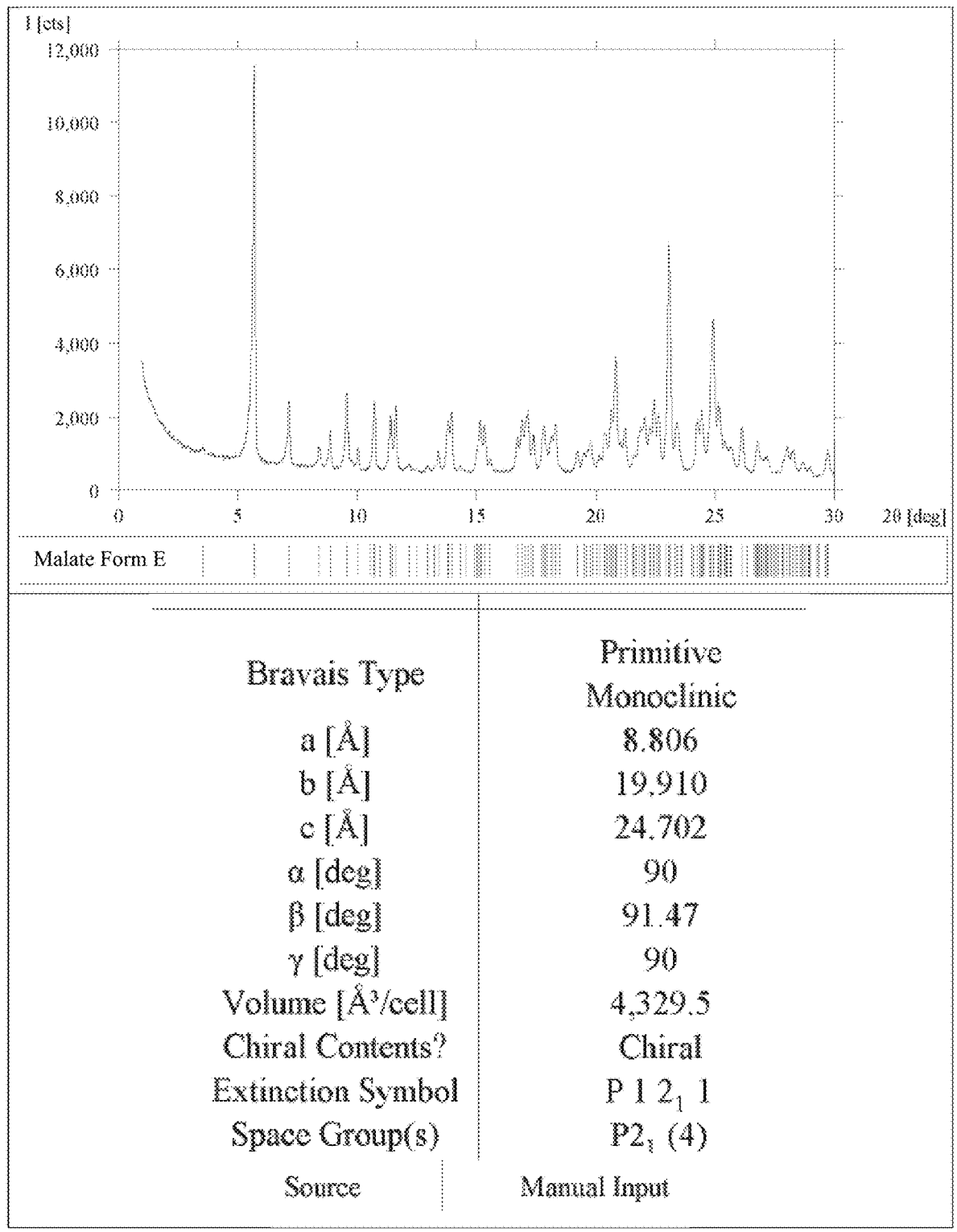

In another embodiment, Malate Form A has an XRPD pattern and indexing solution substantially as shown in FIG. 2A(a) and FIG. 2A(b).

In one embodiment, Malate Form A is substantially free of residual organic solvents.

In one embodiment, the crystalline form of Compound 1 (S)-2-hydroxysuccinate (1:1) is designated as Malate Form E.

In another embodiment, Malate Form E has an XRPD pattern and indexing solution substantially as shown in FIG. 2A(e).

In another embodiment, the crystalline form of Compound 1 (S)-2-hydroxysuccinate (1:1) has an XRPD pattern substantially as shown in FIG. 1A, FIG. 2A(a), FIG. 2A(b), FIG. 2A(c), FIG. 2A(d), and FIG. 2A(e).

In a third aspect, disclosed herein is a crystalline form of N-(3-fluoro-4-((2-(5-(((2-methoxyethyl)amino)methyl) pyridin-2-yl)thieno[3,2-b]pyridin-7-yl)oxy)phenyl)-N'-(4-fluorophenyl)cyclopropane-1,1-dicarboxamide tartrate (hereinafter referred to as Compound 1 Tartrate).

In one embodiment, the crystalline form of Compound 1 Tartrate is a crystalline form of N-(3-fluoro-4-((2-(5-(((2-methoxyethyl)amino)methyl)pyridin-2-yl)thieno[3,2-b] pyridin-7-yl)oxy)phenyl)-N'-(4-fluorophenyl)cyclopropane-1,1-dicarboxamide tartrate (1:1), hereinafter referred to as a crystalline form of Compound 1 Tartrate (1:1).

In one embodiment, the crystalline form of Compound 1 Tartrate is a crystalline form of N-(3-fluoro-4-((2-(5-(((2-methoxyethyl)amino)methyl)pyridin-2-yl)thieno[3,2-b] pyridin-7-yl)oxy)phenyl)-N'-(4-fluorophenyl)cyclopropane-1,1-dicarboxamide (2R,3R)-2,3-dihydroxysuccinate (1:1), hereinafter referred to as a crystalline form of Compound 1 (2R,3R)-2,3-dihydroxysuccinate (1:1) or Compound 1 L-Tartrate (1:1).

In one embodiment, the crystalline form of Compound 1 (2R,3R)-2,3-dihydroxysuccinate (1:1) is designated as Tartrate Form A.

Figure 2B:
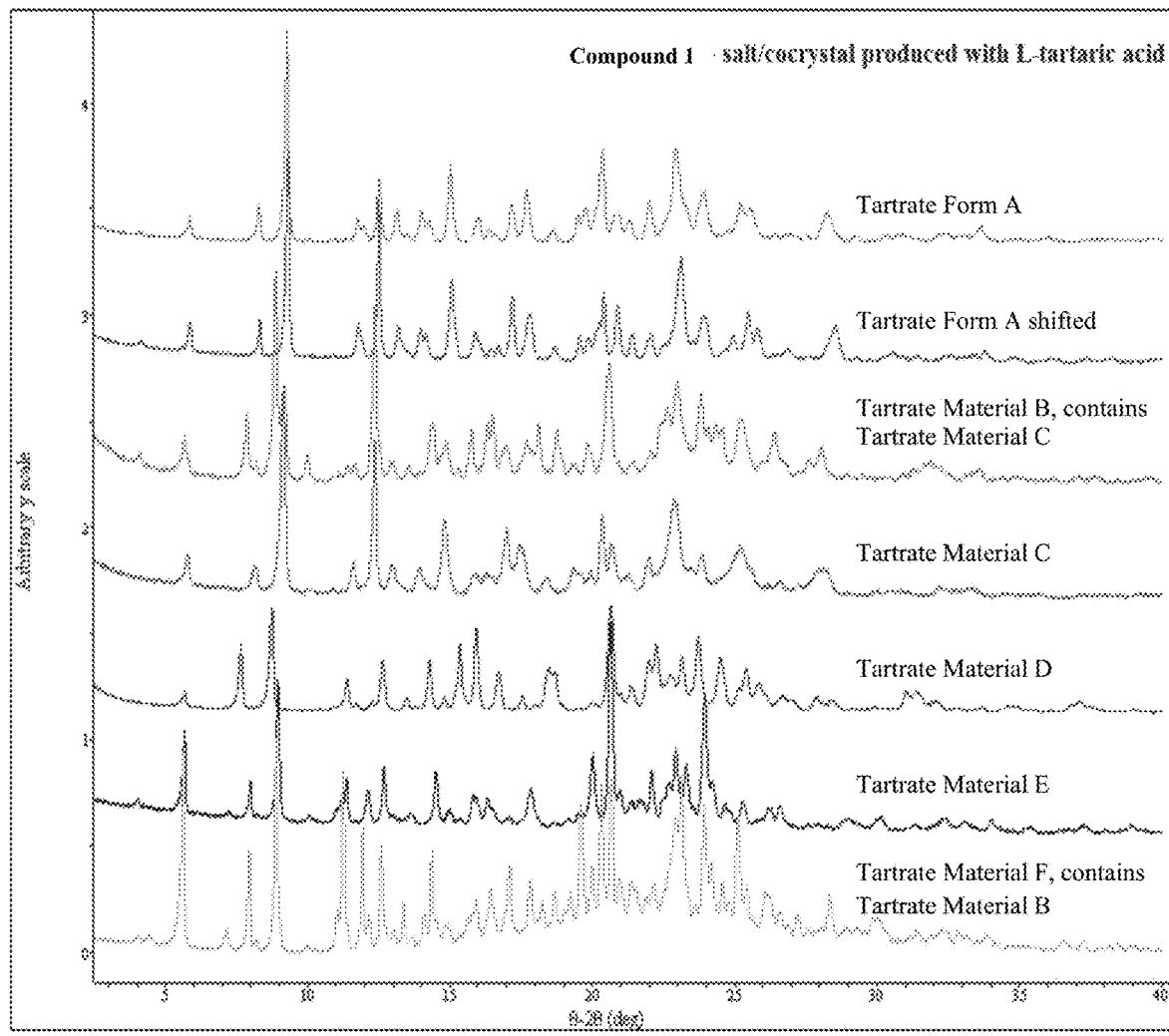
FIG. 2B illustrates X-ray powder diffraction (XRPD) patterns of Compound 1 salt/cocrystal produced with L-tartaric acid, prepared according to Example 2.
Figure 2B:
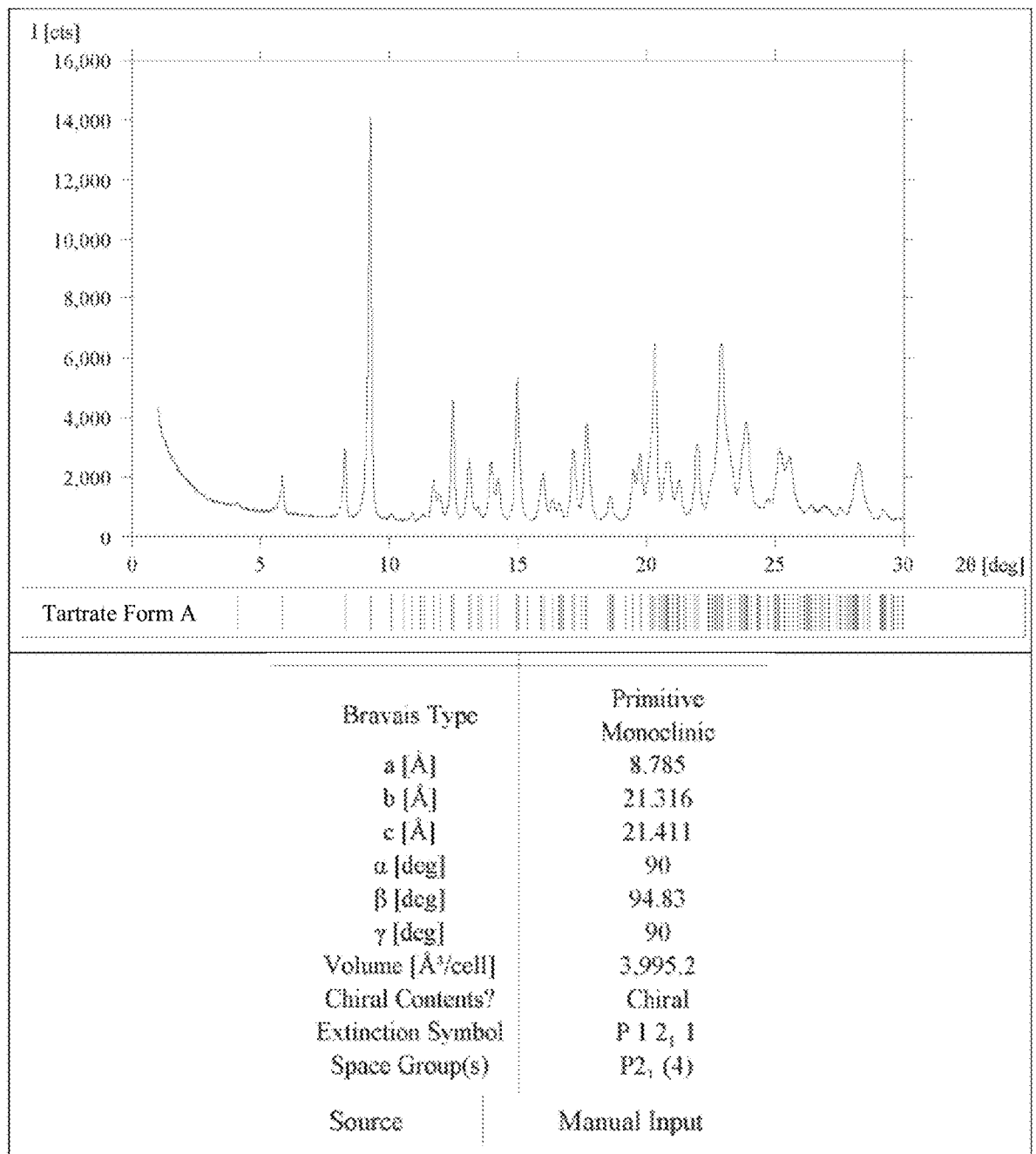
Figure 2B:
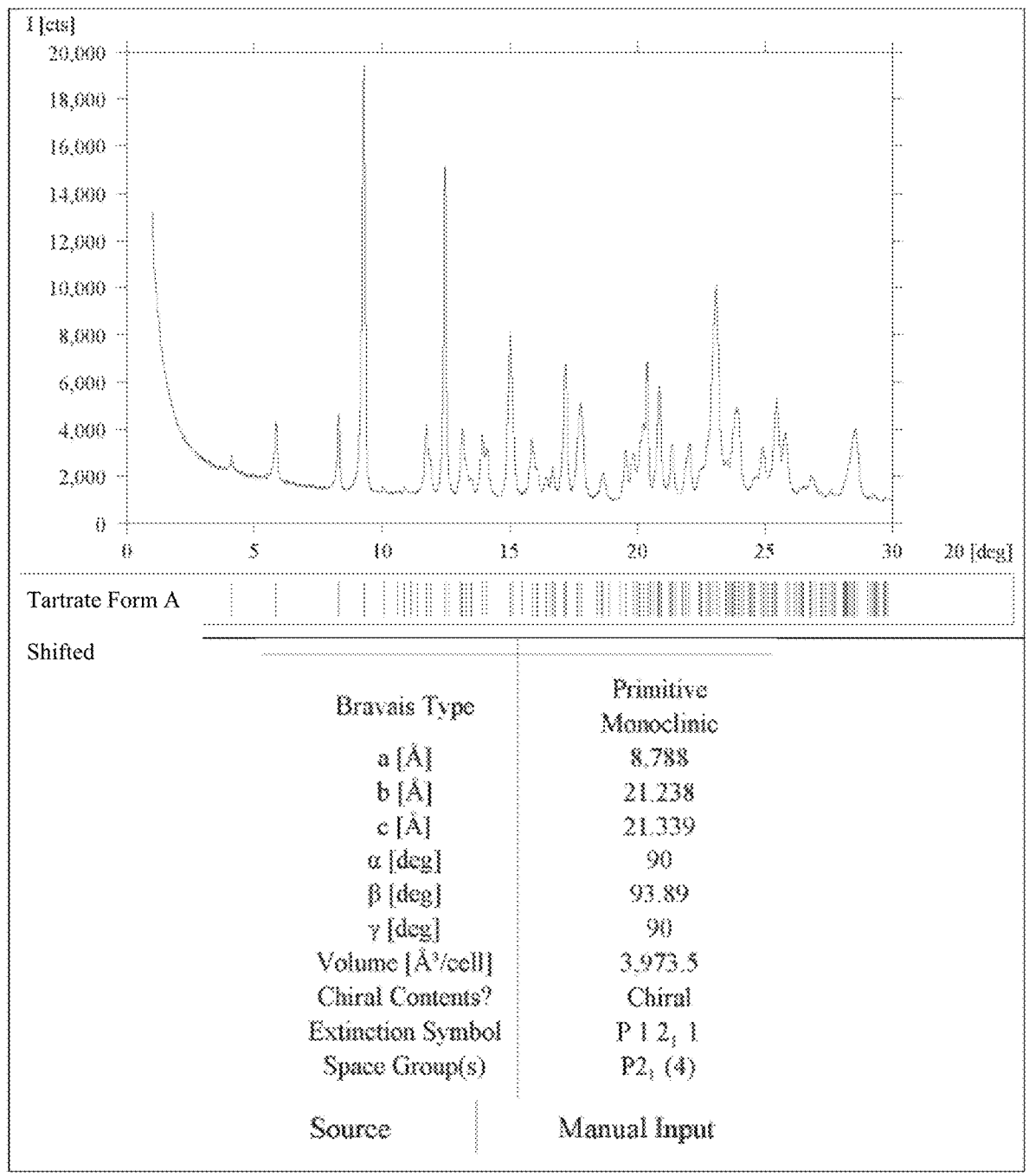

In another embodiment, Tartrate Form A has an XRPD pattern substantially as shown in FIG. 2B(a).

In one embodiment, the crystalline forms are at least 40%, 50%, 60%, 70%, 80%, 90% or 95% crystalline.

In the fourth aspect, disclosed herein is a pharmaceutical composition comprising a therapeutically effective amount of a salt of Compound 1, and pharmaceutically acceptable excipients. In one embodiment, the salt is selected from malate salts, tartrate salts, succinate salts, citrate salts, 1,2-ethanedisulfonate salts, hydrochloride salts, sulfate salts, maleate salts, malonate salts, p-tosylate salts, p-toluate salts, and mandelate salts of Compound 1. In one embodiment, the salt is pharmaceutically acceptable. In one preferred embodiment, the salt is a crystalline form.

In one embodiment, the malate salt is N-(3-fluoro-4-((2-(5-(((2-methoxyethyl)amino)methyl)pyridin-2-yl)thieno[3, 2-b]pyridin-7-yl)oxy)phenyl)-N'-(4-fluorophenyl)cyclopropane-1,1-dicarboxamide malate (1:1).

In one embodiment, the malate salt is a crystalline form of N-(3-fluoro-4-((2-(5-(((2-methoxyethyl)amino)methyl) pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1).

In one embodiment, the tartrate salt is N-(3-fluoro-4-((2-(5-(((2-methoxyethyl)amino)methyl)pyridin-2-yl)thieno[3, 2-b]pyridin-7-yl)oxy)phenyl)-N'-(4-fluorophenyl)cyclopropane-1,1-dicarboxamide tartrate (1:1).

In one embodiment, the tartrate salt is N-(3-fluoro-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (2R,3R)-2,3-dihydroxysuccinate (1:1).

In one embodiment, the salt is in a crystalline form selected from Malate Form A, Malate Form E, and Tartrate Form A. In another embodiment, the salt is in a crystalline form, Malate Form A.

The crystalline forms of Compound 1 salts may be formulated by any method well known in the art and may be prepared for administration by any route, including, without limitation, parenteral, oral, sublingual, transdermal, topical, intranasal, intratracheal, or intrarectal. In certain embodiments, the crystalline form of Compound 1 salts is administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

The active compound is included in the pharmaceutically acceptable carrier or diluent in an amount sufficient to deliver to a patient a therapeutically effective amount without causing serious toxic effects in the patient treated.

In one embodiment, the pharmaceutical composition contain 95% of a crystalline form of a salt of Compound 1. In another embodiment, the pharmaceutical compositions of the present invention contain at least 95% of a crystalline form of a salt of Compound 1. In another embodiment, the pharmaceutical composition contains at least 90% of a crystalline form of a salt of Compound 1. In another embodiment, the pharmaceutical composition contains at least 80% of a crystalline form of a salt of Compound 1. In another embodiment, the pharmaceutical composition contains at least 70% of acrystalline form of a salt of Compound 1. In another embodiment, the pharmaceutical composition contains at least 60% of a crystalline form of a salt of Compound 1. In another embodiment, the pharmaceutical composition contains at least 50% of a crystalline form of a salt of Compound 1.

The pharmaceutical composition comprising a crystalline form of a salt of Compound 1 may be used in the method of use described herein.

In the fifth aspect, disclosed herein is a method for inhibiting multi-tyrosine kinase activity in a cell, comprising contacting the cell in which inhibition of multi-tyrosine kinase activity is desired with a therapeutically effective amount of a pharmaceutically acceptable salt of Compound 1, and pharmaceutically acceptable excipients. In one embodiment, the salt is selected from malate salts, tartrate salts, succinate salts, citrate salts, 1,2-ethanedisulfonate salts, hydrochloride salts, sulfate salts, maleate salts, malonate salts, p-tosylate salts, p-toluate salts, and mandelate salts of Compound 1. In one preferred embodiment, the salt is in a crystalline form.

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1).

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide tartrate (1:1).

In one embodiment, the crystalline form of Compound 1 Tartrate is a crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (2R,3R)-2,3-dihydroxysuccinate (1:1).

In one embodiment, the salt is in a crystalline form selected from Malate Form A, Malate Form E, and Tartrate Form A. In another embodiment, the salt is in a crystalline form, Malate Form A.

In the sixth aspect, disclosed herein is a method of treating cancer in a subject in need thereof, comprising administering to the subject a therapeutically effective dose of a pharmaceutically acceptable salt of Compound 1, and pharmaceutically acceptable excipients.

In one embodiment, the cancer is a multi-tyrosine kinase-associated cancer.

In one embodiment, the multi-tyrosine kinase-associated cancer is lung cancer, including non-small cell lung cancer (NSCLC). In one embodiment, the multi-tyrosine kinase-associated cancer is non-small cell lung cancer (NSCLC).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

In one embodiment, the multi-tyrosine kinase inhibitor, the salt of Compound 1 is orally administered once daily (QD). In one embodiment, the salt of Compound 1 is orally administered twice daily (BID).

In one embodiment, the salt is selected from malate salts, tartrate salts, succinate salts, citrate salts, 1,2-ethanedisulfonate salts, hydrochloride salts, sulfate salts, maleate salts, malonate salts, p-tosylate salts, p-toluate salts, and mandelate salts of Compound 1. In one embodiment, the salt is pharmaceutically acceptable. In one preferred embodiment, the salt is a crystalline form.

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1).

In one embodiment, the malate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide tartrate (1:1).

In one embodiment, the tartrate salt is N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (2R,3R)-2,3-dihydroxysuccinate (1:1).

In one embodiment, the salt is in a crystalline form of L-malate and L-tartrate, particularly Malate Form A, Malate Form E, and Tartrate Form A. In another embodiment, the salt is in a crystalline form, Malate Form A.

In some embodiments of any of the methods described herein, before treatment with the compositions or methods of the present invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

One skilled in the art will recognize that, both in vivo and in vitro trials using suitable, known and generally accepted cell and/or animal models are predictive of the ability of a test compound of the combination or the combination to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

In the seventh aspect, disclosed herein is a process for the preparation of a crystalline form of a salt of Compound 1. In one embodiment, the crystalline form is selected from Malate Form A, Malate Form E, and Tartrate Form A. In another embodiment, the crystalline form is Malate Form A. And, Malate Form A appeared to be a variable hydrate with the water content dependent on the relative humidity and temperature.

In another embodiment, the processes describe the crystallization procedures to prepare Malate Form A from another form or mixture of forms of malate salt of Compound 1.

In one embodiment, Malate Form A is obtained by the process comprising any one of the following procedures:

a) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a water-immiscible solvent, wherein the solvent is selected from methanol, ethanol, acetone or a mixture thereof, heating, cooling, or furtherly removing the solvent, to obtain Malate Form A;

b) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) and Malate Form A as crystal seed in a water-immiscible solvent acetone, heating, adding methanol, cooling, to obtain Malate Form A;

c) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a water-immiscible solvent acetone, slurrying, to obtain Malate Form A;

d) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a water-immiscible ethanol, heating, slurrying, cooling, stirring, to obtain Malate Form A (shifted).

In one embodiment, Malate Form A is obtained by the process comprising the steps:

1) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a mixture of the water-immiscible solvent acetone and a water-miscible organic solvent methanol;
2) heating the resulting suspension to about 70° C. to generate a clear solution;
3) cooling the solution to stimulate crystal formation; and,
4) removing the acetone-methanol mixture to obtain Malate Form A.

In one embodiment, the percent volume ratio of acetone to methanol is 59:41 (v/v).

In another embodiment, the process further comprises collecting the Malate Form A. In another embodiment, the process further comprises drying the Malate Form A in a vacuum oven prior to or after collection.

In one embodiment, Malate Form A is obtained by the process comprising the steps:

1) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) and Malate Form A as crystal seed in a water-immiscible solvent acetone;
2) heating the resulting suspension to about 70° C. to;
3) adding a hot water-miscible organic solvent methanol;
4) cooling the solution to stimulate crystal formation; and,
5) removing the acetone-methanol mixture to obtain Malate Form A.

In one embodiment, the percent volume ratio of acetone to methanol is 59:41 (v/v).

In another embodiment, the process further comprises collecting the Malate Form A. In another embodiment, the process further comprises drying the Malate Form A in a vacuum oven prior to or after collection.

In one embodiment, Malate Form A is obtained by the process comprising the steps:

1) suspending Compound 1 Malate Form A in a water-miscible organic solvent ethanol;
2) heating the resulting suspension to about or over 55° C.;
3) raising the temperature of the resulting suspension to a temperature of about 65-70° C.; and,
4) slowly cooling the suspension to ambient temperature to obtain Malate Form A.

In another embodiment, the process further comprises collecting the Malate Form A. In another embodiment, the process further comprises drying the Malate Form A in a vacuum oven prior to or after collection.

In another embodiment, the processes describe the crystallization procedure to prepare Compound 1 Malate salt from Compound 1 and Malic acid.

In one embodiment, Malate Form A is obtained by the process comprising any one of the following procedures:
1) suspending Compound 1 in a water-miscible organic solvent ethanol, heating, cooling, adding L-malic acid to form the malate salt, cooling to initiate a crystalline form, and further cooling a lower temperature to obtain Malate Form A.

In one embodiment, Malate Form A is obtained by the large scale process comprising the steps:

2) suspending Compound 1 in a water-miscible organic solvent ethanol;
3) heating the resulting suspension to about 75° C.;
4) cooling the temperature of the resulting suspension to a temperature of about 62° C.;
5) adding L-malic acid to form the malate salt;
6) slowly cooling the suspension to a temperature of about 25° C. to initiate a crystalline form; and,
7) cooling the suspension to a temperature of about 0° C. to obtain Malate Form A.

In another embodiment, the process further comprises collecting the Malate Form A. In another embodiment, the process further comprises drying the Malate Form A in a vacuum oven prior to or after collection.

In one embodiment, Malate Form A obtained by the process disclosed herein are at least 40%, 50%, 60%, 70%, 80%, 90% or 95% crystalline.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "Compound 1" refers to N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide, which is a free base.

As used herein, "a salt of Compound 1," "a Compound 1 salt," "salts of Compound 1" or "Compound 1 salts" refers to a salt of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide. For example, "Compound 1 malate salt" or "Compound 1 malate" refers to a malate of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide.

As used herein, a "crystalline form of a salt of Compound 1," "crystalline form of a Compound 1 salt," "crystalline form of salts of Compound 1" or "crystalline form of Compound 1 salts" refers to a crystalline form of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide salts.

Materials exhibiting unique crystalline XRPD patterns are assigned sequential Roman alphabetical characters as the default designation, if no other characteristic types already pertain to the compound. The designation is tentatively associated with the term 'Material' until the phase purity obtained through indexing of the XRPD pattern, and chemical identity obtained through proton nuclear magnetic resonance spectroscopy ($^1$H NMR) is determined. When the characterization data is consistent with a unique crystalline form composed of a single phase, Materials are further designated as "Forms" with the same letter designation (i.e., Material C becomes Form C). In the present disclosure, the XRPD pattern of a "Form" of the compound can be successfully indexed. But, the XRPD pattern of a "Material" can not be indexed, whether due to the "Material" existing as a crystalline material with some degree of disorder, or as a mixture.

As used herein, the term "Malate Form A" or "Compound 1 Malate Form A" when used alone refers to Crystalline Form A of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1). The terms "Malate Form A" or "Compound 1 Malate Form A," "Malate Form E" or "Compound 1 Malate Form E," "Tartrate Form A" or "Compound 1 Tartrate Form A", have similar meaning as that of "Malate Form A" or "Compound 1 Malate Form A".

As used herein, the term "solvate" refers to a crystalline form of Compound 1 or its salts which contains solvent.

As used herein, the term "hydrate" refers to a solvate wherein the solvent comprises water. For its special crystal structure, Malate Form A disclosed herein could be a variable hydrate comprising water or not comprising water, which may not effect the properties of Malate Form A.

As a variable hydrate, the selected Malate Form A, along with patterns or Materials C and D, represent a continuum of interrelated crystal types which differ in the amount of water contained in the crystal lattice. Their relationship to each other is evidenced by the following observations:

1.) Fully reversible conversion of Form A to patterns C and D and back to Form A through dehydration and rehydration, without loss of crystallinity. This behavior is characteristic of a variable hydrate where XRPD reflection angles migrate slightly due to changes in spatial dimensions of the unit cell from the influx or outflux of moisture. However, throughout the RH cycle, the crystal lattice remains fully preserved, with no sign of deterioration;

2.) Tight correlation between weight gain/weight loss observed by DVS and changes in KF as a function of RH; and, 3.) DVS with no noticeable hysteresis, showing complete reversibility of hydration states.

As used herein, the term "residual organic solvents" refers to organic volatile chemicals used or produced during the crystallization/manufacturing processes that are not completely removed during the manufacturing technique.

As used herein, the term "substantially free of residual organic solvents" means that the manufactured pharmaceutical preparation, e.g., a crystalline form of Compound 1 salts, contains less than 0.5% by weight of residual organic solvents, contains less than 0.4% by weight of residual organic solvents, contains less than 0.3% by weight of residual organic solvents, contains less than 0.2% by weight of residual organic solvents, or contains less than 0.1% by weight of residual organic solvents.

A "multi-tyrosine kinase-associated disease or disorder" as used herein refers to diseases or disorders associated with or mediated by oncogenic driver mutations in RET, CBL, CHR4q12, DDR and/or Trk.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject is suspected of having a multi-tyrosine kinase-associated cancer.

In one embodiment, the multi-tyrosine kinase-associated cancer is lung cancer cancer, including non-small cell lung cancer (NSCLC). In one embodiment, the multi-tyrosine kinase-associated cancer is non-small cell lung cancer (NSCLC)

As used herein, a "therapeutically effective amount" of a crystalline form of a salt of Compound 1 is an amount that is sufficient to ameliorate, or in some manner reduce a symptom or stop or reverse progression of a condition, or negatively modulate or inhibit the activity of a multi-tyrosine kinase. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, the term "about" when used to modify a numerically defined parameter (e.g., the dose of a crystalline form of a salt of Compound 1 detailed herein, or the length of treatment time described herein) means that the parameter may vary by as much as 10% below or above the stated numerical value for that parameter. For example, a dose of about 5 mg/kg may vary between 4.5 mg/kg and 5.5 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg. Likewise, about 5% or more, 10% or more, 15% or more, 20% or more, and 25% or more means about 5% or more, about 10% or more, about 15% or more, about 20% or more, and about 25% or more.

As used herein, the term "about" when used in reference to XRPD peak positions refers to the inherent variability of peaks depending on the calibration of the instrument, processes used to prepare the crystalline forms of the present invention, age of the crystalline forms and the type of instrument used in the analysis. The variability of the instrumentation used for XRPD analysis was about ±0.2°2θ.

As used herein, the term "about" when used in reference to DSC endothermic peak onset refers to the inherent variability of peaks depending on the calibration of the instrument, method used to prepare the samples of the present invention, and the type of instrument used in the analysis. The variability of the instrumentation used for DSC analysis was about ±1° C.

General Methods

The general methods outlined below were used in the exemplified Examples, unless otherwise noted.

I. Crystallization Techniques

Crystalline forms disclosed herein may be prepared using a variety of methods well known to those skilled in the art including crystallization or recrystallization from a suitable solvent or by sublimation. A wide variety of techniques may be employed, including those in the exemplified Examples, for crystallization or recrystallization including evaporation of a water-miscible or a water-immiscible solvent or solvent mixture, crystal seeding in a supersaturated solution, decreasing the temperature of the solvent mixture, or freeze drying the solvent mixture.

Crystallization disclosed herein may be done with or without crystal seed. The crystal seed may come from any previous batch of the desired crystalline form.

| ABBREVIATIONS and ACRONYMS | | |
|---|---|---|
| Category | Abbreviations/ Acronyms | Full Name/Description |
| Analytical Techniques | DSC | Differential scanning calorimetry |
| | DVS | Dynamic vapor sorption |
| | HPLC | High Performance Liquid Chromatography |
| | KF | Karl Fischer |
| | NMR | Nuclear magnetic resonance |
| | TGA | Thermogravimetric analysis |
| | XRPD | X-ray powder diffraction |
| | VRH-XRPD | Variable relative humidity X-ray powder diffraction |
| | VT-XRPD | Variable temperature X-ray powder diffraction |
| Solvent | ACN | Acetonitrile |
| | CHCl3 | Chloroform |
| | CH3NO2 | Nitromethane |
| | DCM | Dichloromethane |
| | DEE | Diethyl ether |
| | DMA | Dimethylamide |
| | DMF | Dimethylformamide |
| | DMSO | Dimethyl sulfoxide |
| | EtOH | Ethanol |
| | EtOAc | Ethyl acetate |
| | HFIPA | Hexafluoroisopropanol |
| | IPA | Isopropyl alcohol |
| | MEK | Methyl ethyl ketone |
| | MeOH | Methanol |
| | MTBE | Methyl-tert-butyl ether |
| | TFE | Trifluoroethanol |
| | THF | Tetrahydrofuran |
| Agent | t-BuOK | Potassium tert-butoxide |
| | EDSA | 1,2-ethanedisulfonic acid |
| | NaOH | Sodium hydroxide |
| | aq. | Aqueous |
| | BE | Birefringence with Extinction |
| | Eq. | Equivalent |
| | IPC | In process control |
| | Vol or vol. | Volume |
| | w/w | Weight/weight |

The following Examples are intended to illustrate further certain embodiments of the invention and are not intended to limit the scope of the invention.

Example 1

Preparation of Crystalline Form A of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1)

This Example illustrates the preparation of Crystalline Form A of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1).

Methods for manufacturing the multi-tyrosine kinase inhibitor disclosed herein, N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (Compound 1), are known. For example, commonly owned international applications Publication Nos. WO 2009/026717A and WO2009/026720A describe suitable intermediates and general reaction schemes for preparing multi-tyrosine kinase inhibitor compounds, and also provide a detailed synthetic route for the preparation of the free base of the multi-tyrosine kinase inhibitor disclosed herein. In addition, Compound 1 malate may be prepared, for example, according to the process described in Example 1.

Example 1A: Preparation of Crystalline Form A of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) (Compound 1 Malate Form A, or Malate Form A)

N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (Compound 1, free base) was taken in absolute ethanol (30 vol.), heated to 75±5° C. to get a clear solution and cooled to 62±5° C. L-(-) Malic acid solution (1.0 eq. in 3.8 vol. of absolute ethanol) was added dropwise and stirred for about 24 hours. The reaction mass was slowly cooled to 25±5° C. over a period of about 8 hours and then stirred for about 8 hours at 25±5° C. The reaction mass was cooled to 0±5° C., stirred for about 1 hour, filtered and washed the solid with absolute ethanol (2.0 vol.). The sample was analyzed for XRPD and purity by HPLC. The sample was dried under vacuum 45±5° C. to afford Compound 1 malate salt as off-white solid (Compound 1 Malate Form A).

Compound 1 Malate Form A: $^1$H NMR (500 MHz, DMSO) δ=10.41 (s, 1H), 10.00 (s, 1H), 8.64 (d, J=1.5 Hz, 1H), 8.53 (d, J=5.5 Hz, 1H), 8.37 (s, 1H), 8.29 (d, J=8.0 Hz, 1H), 7.98 (dd, J=2.0, 6.0 Hz, 1H), 7.89 (dd, J=2.0, 11.5 Hz, 1H), 7.62 (td, J=5.0, 2.0 Hz, 2H), 7.45 (m, 2H), 7.12 (tq, J=3.5 Hz, 2H), 6.65 (d, J=5.5 Hz, 1H), 4.03 (s, 4H), 3.50 (t, J=5.5 Hz, 7H), 2.92 (m, 3H), 2.51 (m, 1H), 2.34 (dd, 5.5, 10.5 Hz, 1H), 1.47 (d, J=5.0 Hz, 4H).

Example 1B: Preparation of Compound 1 Malate Form A (Salt Formation and Crystallization)

A 3.0 kg amount of Compound 1 (free base) was suspended in a flask containing 91.25 L of absolute ethanol and the suspension was heated to 75±5° C. to form a clear solution, which was cooled to a temperature of about 62±5° C. A 0.69 kg of L-(-) Malic acid was added dropwise and stirred for up to 24 hr. The solution was slowly cooled to 25±5° C. over a period up to 8 hr, and stirred for an additional 8 hr at a temperature of about 25±5° C. The solution was cooled to a temperature of about 0±5° C., stirred for 1 hr, filtered by vacuum filtration, washed with 7.6 L of chilled absolute ethanol. The final solid (Compound 1 malate salt) was dried at a temperature of about 45±5° C. and collected. Weight of the Compound 1 malate salt: 3.38 kg at a yield of 92.86%, with a purity of 98.7% as determined by HPLC analysis.

X-Ray Powder Diffraction (XRPD)

In one instance, X-Ray Powder Diffraction patterns (diffractograms) were collected using a PANalytical X'Pert PRO MPD diffractometer using an incident beam of Cu radiation produced using an Optix long, fine-focus source. An elliptically graded multilayered mirror was used to focus Cu Kα X-rays through the specimen and onto the detector. Prior to analysis, a silicon specimen (NIST SRM 640e) was analyzed to verify the observed peak position of the Si 111 peak is consistent with NIST-certified position.

A specimen of each sample was sandwiched between two 3 μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen using Data Collection software v2.2b.

In another instance, XRPD patterns were collected using a PANalytical X'Pert PRO MPD diffractometer using an incident beam of Cu radiation produced using an Optix long, fine-focus source and a nickel filter. The diffractometer was configured using the symmetric Bragg-Brentano geometry. Prior to analysis, a silicon specimen (NIST SRM 640e) was analyzed to verify the observed peak position of the Si 111 peak is consistent with NIST-certified position.

A specimen of each sample was prepared as a thin, circular layer centered on a silicon zero-background substrate. Antiscatter slits were used to minimize the background generated by air. Soller slits for the incident and diffracted beams were used to minimize broadening from axial divergence. Diffraction patterns were collected using a scanning position-sensitive detector (X'Celerator) located 240 mm from the specimen using Data Collection software v2.2b.

The X-ray powder diffraction (XRPD) pattern was used to characterize the Compound 1 L-malate salt obtained, which showed that the Compound 1 L-malate salt was in a crystalline form, designated as Crystalline Form A of Compound 1 L-malate salt (Compound 1 Malate Form A, or Malate Form A), see FIG. 1A. The characteristic peaks and percent peak intensities obtained from the XRPD analysis are listed in Table 1A.

TABLE 1A

XRPD pattern of Crystalline Form A of Compound 1 Malate (Malate Form A)

| Diffraction angle (2-theta) | Intensity/% |
|---|---|
| 4.8 | 2.1 |
| 6.0 | 14.2 |
| 8.6 | 18.2 |
| 9.6 | 100.0 |
| 12.0 | 22.2 |
| 12.6 | 73.6 |
| 13.5 | 13.4 |
| 13.9 | 6.3 |
| 14.7 | 22.2 |
| 15.3 | 42.2 |
| 16.9 | 14.7 |
| 17.4 | 19.1 |
| 17.7 | 13.7 |
| 18.1 | 8.6 |
| 18.4 | 13.6 |
| 19.1 | 3.1 |
| 20.0 | 12.7 |
| 20.3 | 31.1 |
| 21.0 | 31.4 |
| 22.0 | 24.4 |
| 22.9 | 17.5 |
| 23.2 | 28.4 |
| 24.1 | 31.8 |
| 24.2 | 23.5 |
| 24.8 | 14.5 |
| 25.4 | 15.3 |
| 25.6 | 9.5 |
| 26.2 | 7.5 |
| 27.8 | 5.7 |
| 28.2 | 5.9 |
| 29.1 | 5.2 |
| 29.7 | 3.8 |
| 30.3 | 1.6 |
| 30.7 | 3.4 |
| 31.5 | 1.6 |
| 32.3 | 3.8 |
| 33.5 | 4.6 |
| 34.2 | 3.5 |
| 34.5 | 3.1 |
| 35.2 | 2.8 |

TABLE 1A-continued

XRPD pattern of Crystalline Form A of
Compound 1 Malate (Malate Form A)

| Diffraction angle (2-theta) | Intensity/% |
|---|---|
| 38.2 | 2.9 |
| 39.3 | 1.6 |

Example 1C: Preparation of Compound 1 Malate Form A (Recrystallization)

A 34 mg amount of a mixture of Compound 1 Malate Form A and another crystalline material of Compound 1 malate was weighed, placed in a tube and mixed with 2 mL of acetone added in four 500 μL aliquots. The suspension was heated at 70° C. on a hot plate to which 1.4 mL of 70° C. methanol was added in succession in five separate aliquots (500 μL×2; 200 μL; then 100 μL×2) until a clear solution was obtained. The final ratio of acetone to methanol for the clear solution was 59:41 (% volume).

Once the solution was clear, the hot plate was turned off and the sample was slowly cooled to ambient temperature. After three days at ambient temperature, aggregates of small fines and needles, with birefringence and extinction, were observed in the solution. The sample was transferred to subambient temperatures, e.g., 2-8° C. After 11 days, the solvent was decanted and the remaining solids were briefly dried with a gentle stream of nitrogen gas prior to XRPD analysis, which yielded an XRPD pattern substantially the same as that shown in FIG. 1A.

Example 1D: Preparation of Compound 1 Malate Form A (Recrystallization)

A 48 mg amount of a mixture of Compound 1 Malate Form A and another crystalline material of Compound 1 malate was weighed, placed in a tube and mixed with 1.4 mL of ethanol in seven 200 μL aliquots. The suspension was heated to about 55° C. An additional twenty six 200 μL aliquots of 55° C. ethanol were added in succession and the temperature was raised to about 65-70° C.

After heating at about 65-70° C., solids were still present to which another twenty 200 μL aliquots of ~65° C. ethanol were added in succession. The resulting solution was stirred for an hour at about 65-70° C. to which another ten 200 μL aliquots of about 65° C. ethanol were added in succession. A slightly cloudy solution was obtained, and the hot plate was turned off and the cloudy solution was allowed to slowly cool to ambient temperature. After one day at ambient temperature, resulting solids were collected by vacuum filtration. The XRPD pattern for the alternative preparation of crystalline malate salt was substantially the same as that shown in FIG. 1A.

Example 1E Differential Scanning Calorimetry (DSC) Analysis of Compound 1 Malate Form A Differential Scanning Calorimetry (DSC)

DSC data were collected on a TA Instruments Q2000 differential scanning calorimeter. Temperature calibration was performed using NIST-traceable indium metal. The samples were placed into an aluminum DSC pan, covered with a lid and the weight was accurately recorded. A weighed aluminum pan configured as the sample pan was placed on the reference side of the cell.

Alternatively, DSC analysis was performed using a Mettler-Toledo TGA/DSC3+ analyzer. Temperature calibration was performed using adamantane, phenyl salicylate, indium, tin and zinc. The samples were placed into an aluminum DSC pan, covered with a lid and the weight was accurately recorded. A weighed aluminum pan configured as the sample pan was placed on the reference side of the cell. The sample pan lid was pierced prior to heating and analysis.

Typically, samples were heated for analysis at a rate of 10° C./min from a temperature of about −30° C. to a temperature of about 250° C.

DSC analysis of Compound 1 Malate Form A was conducted using a TA Instrument Q2000 differential scanning calorimetry module per the manufacturer's instructions.

Briefly, ~3 mg of malate Form A was placed in a tared aluminium pan, covered with a crimped aluminum lid and heated using an underlying heating rate of 10° C./min and temperature modulation from 25° C. to 300° C. A purge of dry nitrogen at 50 ml/min was maintained over the sample. A weighed aluminum pan configured as the sample pan was placed on the reference side of the cell. The instrument control software used was Advantage for Q Series and Thermal Advantage and the data were analyzed using Universal Analysis.

The DSC thermogram of a sample of Compound 1_Malate Form A is shown in FIG. 1B. As shown in FIG. 1B, Compound 1_Malate Form A has a broad endothermic event between about 50-125° C. and overlapping endothermic events with a maximum peak value of about 171° C., and degradation above about 185° C.

Example 1F Thermo-Gravimetric Analysis (TGA) of Compound 1 Malate Form A

Thermo-Gravimetric Analysis (TGA)

TGA data were collected on a TA Instruments Q5000 IR thermogravimetric analyzer. Each sample was placed in an aluminum pan with the lid crimped and inserted into the TG furnace. The furnace was heated under nitrogen.

In one embodiment, samples were heated at a rate of 10° C./min from ambient temperature to a temperature of about 300° C. The percent weight loss was calculated at a temperature of about 120° C.

TGA analysis was also conducted using a calibrated TA Instruments Q500 TGA.

Briefly, an ~5 mg of Compound 1 Malate Form A (Malate Form A) was loaded onto a pre-tared, 100 μL platinum TGA pan and heated at 10° C./min from ambient temperature to 300° C. A nitrogen purge at 25 mL/min was maintained over the sample. The instrument control software employed for the analysis was Advantage for Q Series and Thermal Advantage and the data were analyzed using Universal Analysis.

The TGA thermogram of Malate Form A is shown in FIG. 1C. As shown in FIG. 1C, there was a minimal gradual loss of mass for Malate Form A of about 2% at 120° C. until degradation onset beginning at about 175° C.

Example 1G Dynamic Vapor Sorption (DVS) Analysis of Compound 1 Malate Form A

Dynamic Vapor Sorption (DVS)

Moisture sorption/desorption data were collected using a Surface Measurement System (SMS) DVS Intrinsic Instrument according to the manufacturer's instructions. Samples were not dried prior to analysis. Sorption/desorption data were collected over a range from 5% to 95% relative humidity (RH) at 10% RH increments under a nitrogen gas purge. The equilibrium criterion used for analysis was less than 0.0100% weight change in 5 min with a maximum equilibration time of three hours. Data were not corrected for initial moisture content of the samples.

The sample was recovered after completion of the isotherm and re-analyzed by XRPD Sorption isotherms of Compound 1 Malate Form A were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Briefly, Malate Form A was placed in a tared mesh stainless steel basket under ambient conditions. The sample was loaded and unloaded at 40% RH and 25° C. (typical room conditions) and allowed to equilibrate to 5% RH. A moisture sorption isotherm was performed as outlined below (1 scan per complete cycle). The standard isotherm was performed at 25° C. at 10% RH intervals over a 5-95% RH range. Data analysis was carried out within Microsoft Excel using the DVS Analysis Suite.

DVS isotherm profile of Malate Form A is shown in FIG. 1D. As shown in FIG. 1D, Malate Form A is characterized by having a weight loss of 1.2 wt % upon equilibration at 5% relative humidity (RH), a weight gain of about 2.1 wt % between 5-25% RH and additional 1.1 wt % gain between 25-95% during the sorption phase. During the desorption cycle, the material loses approximately 1.3 wt % and 1.7% in the 95-15% RH and 15-5% RH, respectively, with minimal hysteresis between ~25% and 5% RH, indicating the sample exists as a variable hydrate.

Example 111 Variable Temperature (VT) and Variable Relative Humidity (VRH) XRPD of Compound 1 Malate Form A Variable Temperature X-Ray Powder Diffraction (VT-XRPD)

An Anton Paar TTK 450 stage was used to collect in-situ XRPD patterns as a function of temperature. The sample was heated with a resistance heater located directly under the sample holder, and the temperature was monitored with a platinum-100 resistance sensor located in the specimen holder. The heater was powered and controlled by an Anton Paar TCU 100 interfaced with Data Collector.

The VT-XRPD data for Malate Form A shown in FIG. 2A(c) show XRPD peak shifting during dehydration of Malate Form A upon gradual heating to 55° C. and rehydration to Malate Form A upon cooling back to ambient temperature.

Variable Relative Humidity X-Ray Powder Diffraction (VRH-XRPD)

An Anton Paar temperature-humidity chamber (THC) was used to collect in-situ XRPD patterns as a function of humidity. The temperature of the specimen was changed with a Peltier thermoelectric device located directly under the specimen holder and monitored with a platinum-100 resistance sensor located in the specimen holder. The thermoelectric device was powered and controlled by an Anton Paar TCU 50 interfaced with Data Collector. The humidity was generated with an RH-200 manufactured by VTI Inc. and carried by a flow of nitrogen gas. The humidity and temperature was monitored by a HygroClip sensor manufactured by Rotronic located next to the specimen inside the THC.

The VRH-XRPD data of Malate Form A suggest that Malic Form A is stable between ~23% and ~78% RH (highest relative humidity tested) and appears to dehydrate reversibly to Malic Material D (or C) at the relative humidity below ~15-23%. This is consistent with the VT-XRPD data. In this respect, Malate Form A, Material C and Material D may be understood as a continuum of interrelated crystal types which differ in the amount of water contained in the crystal lattice, resulting in XRPD peak shifting.

Example 2

Salt/Cocrystal of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (Compound 1)

Salts of N-(3-fluoro-4-((2-(5-(((2-methoxyethyl)amino) methyl)pyridin-2-yl)thieno[3,2-b]pyridin-7-yl)oxy)phenyl)-N-(4-fluorophenyl)cyclopropane-1,1-dicarboxamide (Compound 1) with eight salt-forming agents (salt formers), including L-malic acid, L- and D-tartaric acid, succinic acid, citric acid, 1,2-ethanedisulfonic acid, hydrochloric acid, sulfuric acid, maleic acid, malonic acid, p-toluenesulfonic acid, p-toluic acid, and mandelic acid were prepared, and further investigations for the salts/cocrystal were conducted.
X-Ray Powder Diffraction (XRPD)

Pattern Match versions 2.3.6 and 3.0.4 were used to create the X-ray powder diffraction pattern overlays. Figures labeled "Image by PatternMatch v3.0.4" were generated using unvalidated software and are non-cGMP representations.
PANalytical, Transmission Mode XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.
PANalytical, Reflection Mode XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Data were collected and analyzed using Data Collector software v. 2.2b. Prior to the analysis, a silicon specimen (NIST SRM 640d) was analyzed to verify the observed position of the Si 111 peak is consistent with the NIST-certified position. A specimen of the sample was packed in a nickel-coated copper well. Antiscatter slits (SS) were used to minimize the background generated by air scattering. Soller slits for the incident and diffracted beams were used to minimize broadening from axial divergence. Diffraction patterns were collected using a scanning position-sensitive detector (X'Celerator) located 240 mm from the sample.

Indexing

Indexing of XRPD patterns was performed using either using X'Pert High Score Plus [X'Pert High Score Plus 2.2a (2.2.1).], or the proprietary SSCI software TRIADS. Selected patterns were indexed utilizing previously obtained unit cell parameters and refined using CheckCell. [CheckCell Nov. 1, 2004; http:/www.ccp14.ac.uk/tutorial/lmgp/.] No attempts at molecular packing were performed to confirm tentative indexing solutions.

Polarized Light Microscopy (PLM)

Samples were observed using a Leica MZ12.5 stereomicroscope with a first order red compensator. Various objectives typically ranging from 0.8-10× were used with crossed-polarized light to view the samples. Selected samples were observed in mineral oil.

Thermogravimetry (TGA)

TG analyses were performed using a TA Instruments 2950 thermogravimetric analyzer. Temperature calibration was performed using nickel and Alumel™. Each sample was placed in an aluminum pan and inserted into the TG furnace. The furnace was heated under a nitrogen purge. The data acquisition parameters are displayed above each thermogram in the Data section of this report. The method code on the thermogram is an abbreviation for the start and end temperature as well as the heating rate; e.g., 25-350-10 means "from 25° C. to 350° C., at 10° C./min".

Differential Scanning Calorimetry (DSC)

DSC analyses were performed using a TA Instruments 2920 and Q2000 differential scanning calorimeters. Temperature calibration was performed using NIST-traceable indium. The sample was placed into an aluminum DSC pan, covered with a lid, and the weight was accurately recorded. A weighed aluminum pan (T° C.—Tzero crimped pan, T0CMP—Tzero crimped pan, perforated manually, T0HSLP—Tzero lid hermetically sealed and perforated with a laser pinhole or T0HSMP—Tzero lid hermetically sealed and perforated manually) configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., –30-250-10 means "from –30° C. to 250° C., at 10° C./min.

Solution Proton Nuclear Magnetic Resonance Spectroscopy ($^1$H NMR)

Solution proton NMR spectra were acquired using a 400 MHz instrument using deuterated DMSO.

Karl Fischer Titration

Coulometric Karl Fischer analysis for water determination was performed using a Mettler Toledo DL39 Karl Fischer titrator with a Stromboli oven attachment. Prior to analyses samples tested were exposed to specified ambient relative humidity for ~2 hours. Two replicates of the sample were placed into the drying oven set at a temperature of approximately 140 or 145° C. The drying oven was purged into the titrator vessel with dry nitrogen. The samples were then titrated by means of a generator electrode, which produces iodine by electrochemical oxidation: $2I^- \rightarrow I_2 + 2e^-$. A NIST-traceable water standard (Hydranal Water Standard 10.0) was analyzed to check the operation of the coulometer.

Example 2A: Compound 1 Salt/Cocrystal

Experiments targeting the generation of crystalline materials of several Compound 1 salts were conducted, and typically involved crystallization techniques such as cooling, slurrying at elevated or ambient temperature, evaporation, or combinations of Compound 1 designed on the basis of solubility and stability of Compound 1 and each salt former under various conditions and observed behavior under the selected conditions. The experiments were typically performed at a medium (40-100 mg) scale. Equimolar amounts of the free base and salt formers were utilized in the majority of experiments. Selected experiments were conducted with a 2-fold excess of either the free base or the salt former.

Solids produced were typically analyzed by polarized light microscopy (PLM) initially as a preliminary evaluation of crystallinity. X-ray powder diffraction (XRPD) was subsequently used as a primary analytical technique for initial identification of new crystalline phases. The XRPD patterns were compared to each other, to the patterns of the free base and available patterns of salt formers. $^1$H-NMR spectroscopy was utilized to confirm salt formation when possible, determine stoichiometries of produced candidates and ensure no degradation had occurred.

Crystalline materials of Compound 1 were produced with several salt-forming agents, including L-malic acid, L-tartaric acid, succinic acid, citric acid, 1,2-ethanedisulfonic acid, hydrochloric acid, sulfuric acid, maleic acid, malonic acid, p-toluenesulfonic acid, p-toluic acid, and mandelic acid. The conditions and results of the salt screen experiments of malate, tartrate and succinate are summarized in Table 2A.

At least one material out of those generated with each salt former was characterized by $^1$H-NMR. $^1$H-NMR spectras for the corresponding Compound 1 salt/cocrystal are shown in FIG. 2J, 2K, 2L, 2M, 2N, 2O, 2P, 2Q, 2R, 2S, and 2T. In each case, the data were consistent with salt or cocrystal formation, based on shifts of peaks near 4.4-2.6 ppm range, likely associated with the non-aromatic protons near the secondary amine group, peaks observed due to corresponding counterions (when applicable), or additional peaks near 9-10 ppm likely due to protonation of Compound 1.

XRPD was used to characterize the Compound 1 salt/cocrystals produced. Materials exhibiting unique XRPD patterns are illustrated in FIGS. 2A, 2B, 2C, 2C, 2D, 2E, 2F, 2G, 2H, and 2I. The majority of materials produced are crystalline solids displaying various degree of disorder or were solvated. A material produced with 1,2-ethanedisulfonic acid has a severely disordered nature. One crystalline form of each, the malate and the tartrate salt could successfully be produced in a single crystalline phase of crystalline form, as evidenced by indexing of their XRPD pattern. The two forms are designated as Malate Form A and Tartrate Form A. The indexing XRPD patterns of Malate Form A, Malate Form A (shifted), Tartrate Form A and Tartrate Form A (shifted) are further shown as FIG. 2A(a), FIG. 2A(b), FIG. 2B(a) and FIG. 2B(b). Peak shifting and slightly different indexing results for these forms when produced from different conditions indicate a similar ability of the two crystal structures to expand and contract to some level depending on conditions of formation or water content. In addition, Malate Materials B and C had an XRPD pattern as substantially the same as that of Malate Form A, but with some shifted peaks.

TABLE 2A

| | | | Observation | XRPD |
|---|---|---|---|---|
| Salt Former | No. | Conditions (a) | (b) | Results |
| L-malic acid
The ¹H NMR data for the material (generated in ethanol) is consistent with Compound 1 containing ~1 mol of malic acid per mol of Compound 1, based on multiplets near 4.0 ppm and 2.6-2.2 ppm, each overlapped with protons from Compound 1 and solvent of analysis. | 1 | Suspended free base/acid mixture in acetone (partial dissolution then precipitation). Slurried at RT (by stirring and rotating wheel) for 5 days. | Gel-like + very small particles with birefringence and extinction | Crystalline, Malate Form A |
| | 2 | Suspended free base in EtOH at 62-64° C. (majority dissolved). Mixed with hot solution of acid in EtOH (clear then precipitated). Added more EtOH, slurry at 62-64° C. for 3 hours. Slowly cooled to RT, stirred at RT overnight. | Needles, birefringence and extinction | Crystalline, Malate Form A (shifted) |
| | 3 | Suspended free base/acid mixture in warm THF (slightly cloudy). Stirred at 60° C. for 20 mins. Slowly cooled to RT (further precipitated, gel-like). Slurried at RT (rotating wheel) for 5 days. | Unknown morphology, birefringence and extinction | Crystalline with disorder, Malate Material B |
| | 4 | Dissolved acid in EtOH. Mixed with solution of free base in THF (clear). Stirred at RT for 4 days. | Unknown morphology, small particles, some birefringence and extinction | Crystalline with disorder, Malate Material C, may contain Malate Material B + peaks |
| L-tartaric acid
The material generated is consistent Compound 1 containing ~1 mol of tartaric acid per mol of Compound 1, based on the additional peak at ~4.1 ppm. | 1 | Suspended free base in EtOH at 62-64° C. Mixed with hot solution of acid in EtOH (additional precipitation). Added more EtOH, slurry at 62-64° C. for 3 hours. Slowly cooled to RT, and stirred at RT overnight. | Needles or rods, smaller particles, birefringence and extinction | Crystalline with some disorder. Tartrate Form A, single crystalline phase [Tartrate Form A-1] |
| | 2 | Tartaric Form A-1 obtained above, was stored at 2-8° C. for 4 weeks. | — | Remained same as Tartrate Form A |
| | 3 | Dissolved acid in MeOH. Mixed with suspension of free base in acetone (additional precipitation). Stirred at RT for 3 days. | Unknown morphology, small particles, birefringence and extinction | Crystalline with some disorder. Tartrate Form A (shifted) |
| | 4 | Suspended free base/acid mixture in MEK at 62-64° C. (nearly clear). Slurried at 62-64° C. for 3 hours. Slowly cooled to RT, stirred at RT overnight. | Unknown morphology, small particles, birefringence and extinction | Crystalline with some disorder Tartrate Material B, contains Tartrate Material C |
| | 5 | Suspended free base/acid mixture in MEK/acetone/MeOH (3/3/1) (clear then precipitation). Stirred at RT for 4 days. | Gel + unknown morphology, birefringence and extinction | Crystalline with some disorder, Tartrate Material B, may contain Tartrate Material E |
| | 6 | Suspended free base/acid mixture in EtOAc at 60° C. (partial dissolution). Added EtOH and THF (EtOAc/THF/EtOH 20/5/3). Continued stirring at 60° C. | — | Crystalline with some disorder, Tartrate Material C |

TABLE 2A-continued

Compound 1 salt/cocrystal

| Salt Former | No. | Conditions (a) | Observation (b) | XRPD Results |
|---|---|---|---|---|
| Succinic acid The $^1$H NMR data of the materials (produced from methanol/chloroform and dioxane) are consistent with Compound 1 containing ~1 mol of succinic acid per mol Compound 1, based on the additional peak near ~2.4 ppm. | 1 | Dissolved acid in MeOH. Mixed with solution of free base in chloroform, MeOH/chloroform 1/12 (clear). Stirred at RT. | Clear | — |
| | 2 | Dissolved acid in MeOH. Mixed with solution of free base in chloroform, MeOH/chloroform 1/12 (clear). Stirred at RT.. Slowly evaporated to dryness. | Very small needles, birefringence and extinction | Crystalline with some disorder, Succinate Material A or B, contains Succinate Material C |
| | 3 | Dissolved free base in dioxane at 62-64° C. Mixed with warm solution of acid in dioxane (clear then some precipitation). Stirred at 62-64° C. Fast cooled to RT, overnight. | Needles, birefringence and extinction | Crystalline, Succinate Material C, contains Succinate Material B |
| | 4 | Suspended free base/acid mixture in acetone (clear then precipitation). Stirred at RT for 4 days | Possibly needles, very small, birefringence and extinction | Crystalline with some disorder. Succinate Material D, contains Succinate Material A or B |
| | 5 | Suspended free base/acid mixture in warm THF (clear). Stirring at 60° C., 5 min. slowly cooled to RT with stirring for 5 days. | Unknown morphology, birefringence and extinction | Crystalline with some disorder. Succinate Material E |
| | 6 | Suspended free base/acid mixture in MEK at 62-64° C. (re- precipitation). Slurry at 62-64° C., 3 hours. Slowly cooled to RT, and stirred at RT overnight. | Needles, birefringence and extinction | Crystalline Succinate Material F, contains Succinate Materials D and A or B |

(a) Ratio of free base to acid is 1/1. Temperature and duration of experiments are approximate.
(b) Observed in mineral oil unless otherwise indicated.

Example 2B Scale-Up of Compound 1 Salts/Cocrystals

The crystalline materials of Compound 1 salts/cocrystals, including Compound 1 Malate Form A, Tartrate Form A and Succinate Material A were selected for a scale-up to generate additional quantities for further characterization and stable form activity. Due to a large number of different materials produced with the same salt former (most not indexable by XRPD), the selection of targeted forms for the scale-up was mainly based on the apparent crystallinity by XRPD and the absence of organic solvents by $^1$H-NMR.

The conditions and results of scale-up experiments are summarized in Table 2B. The XRPD patterns were used to characterize the Compound 1 salts/cocrystals produced, which is illustrated in FIG. 2U. Based on XRPD data, a new material designated as Malate Material D was obtained at larger scale, Tartrate Form A with slightly shifted pattern was obtained, and a new material designated as Succinate Material G (possibly contained Succinic Material D) but not the targeted Succinate Material A was obtained. $^1$H NMR, TGA/DSC data were acquired on the samples to further characterize the salt/cocrystal obtained.
Malate Material D obtained $^1$H NMR spectrum is consistent with containing ~0.8 moles of malic acid, based on additional peaks near ~4.0 ppm and 2.6-2.2 ppm range attributable to the counterion and overlapped with protons from and the solvent of analysis and no process solvent was detected by $^1$H NMR.

Figure 2C:
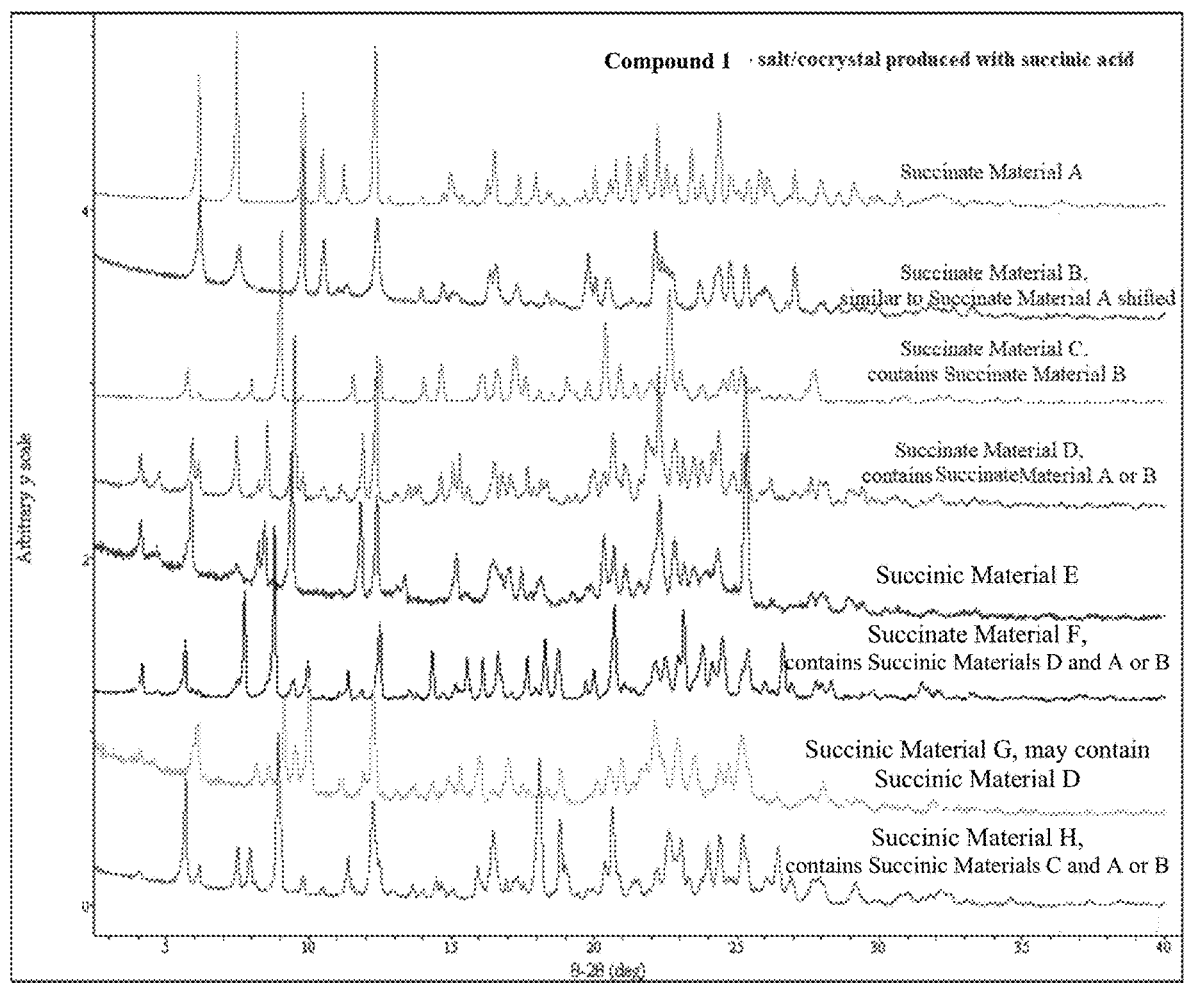
FIG. 2C illustrates X-ray powder diffraction (XRPD) patterns of Compound 1 salt/cocrystal produced with succinic acid, prepared according to Example 2.
Figure 2D:
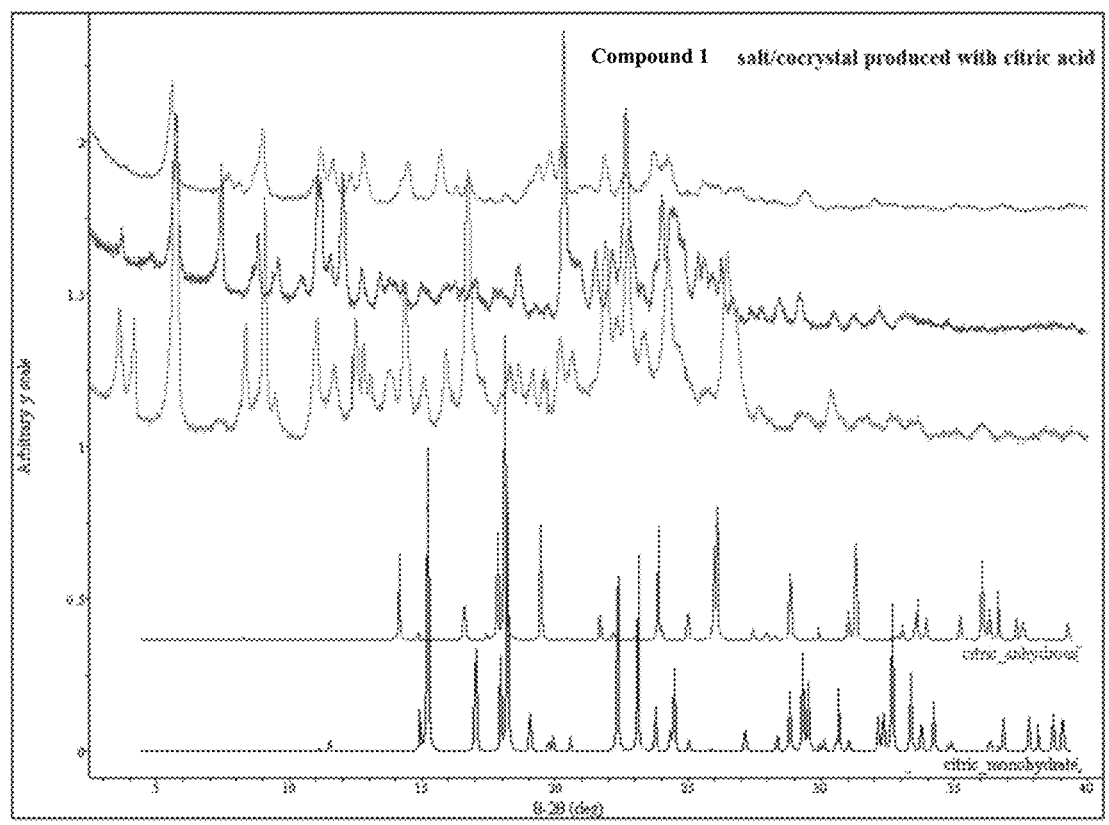
FIG. 2D illustrates X-ray powder diffraction (XRPD) patterns of Compound 1 salt/cocrystal produced with citric acid, prepared according to Example 2.
Figure 2E:
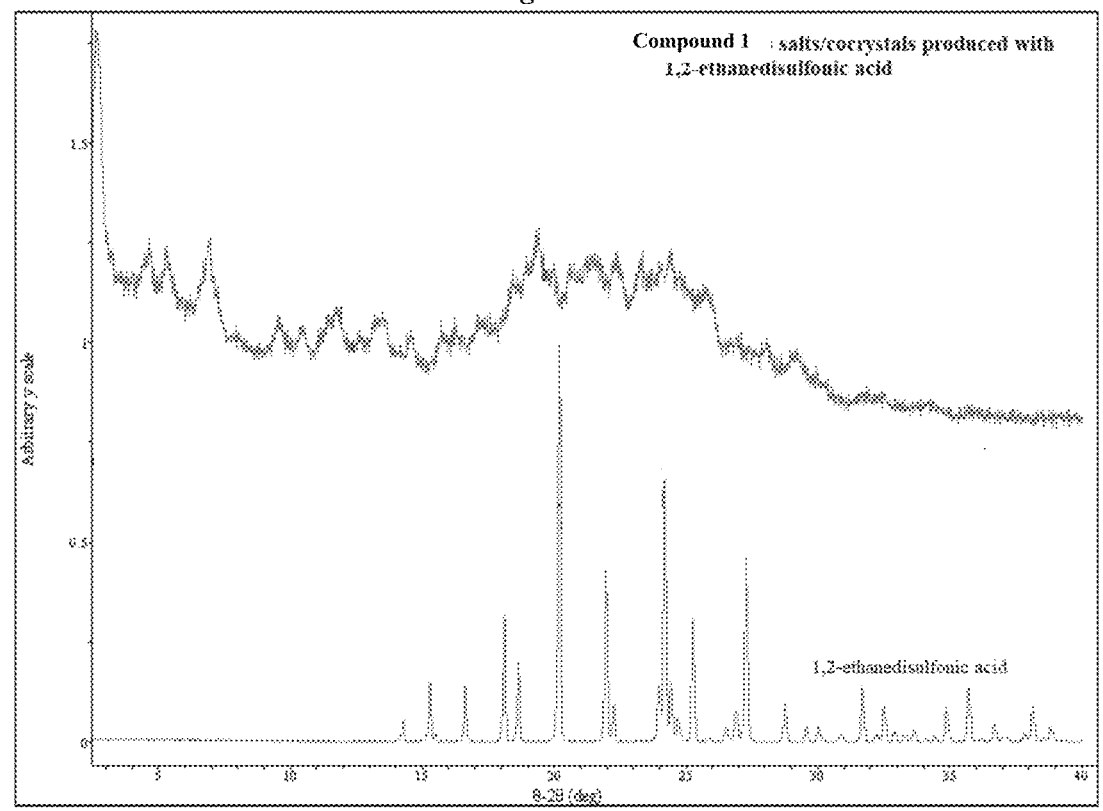
FIG. 2E illustrates X-ray powder diffraction (XRPD) patterns of Compound 1 salt/cocrystal produced with 1,2-ethanedisulfonic acid, prepared according to Example 2.
Figure 2F:
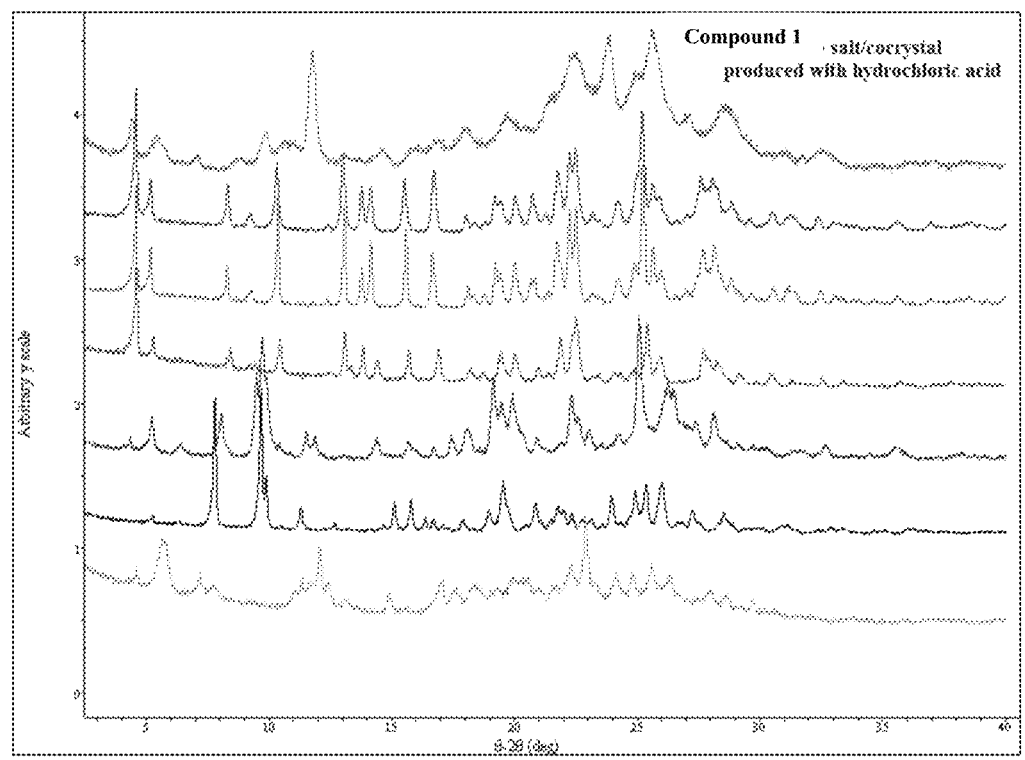
FIG. 2F illustrates X-ray powder diffraction (XRPD) patterns of Compound 1 salt/cocrystal produced with hydrochloric acid, prepared according to Example 2.
Figure 2G:
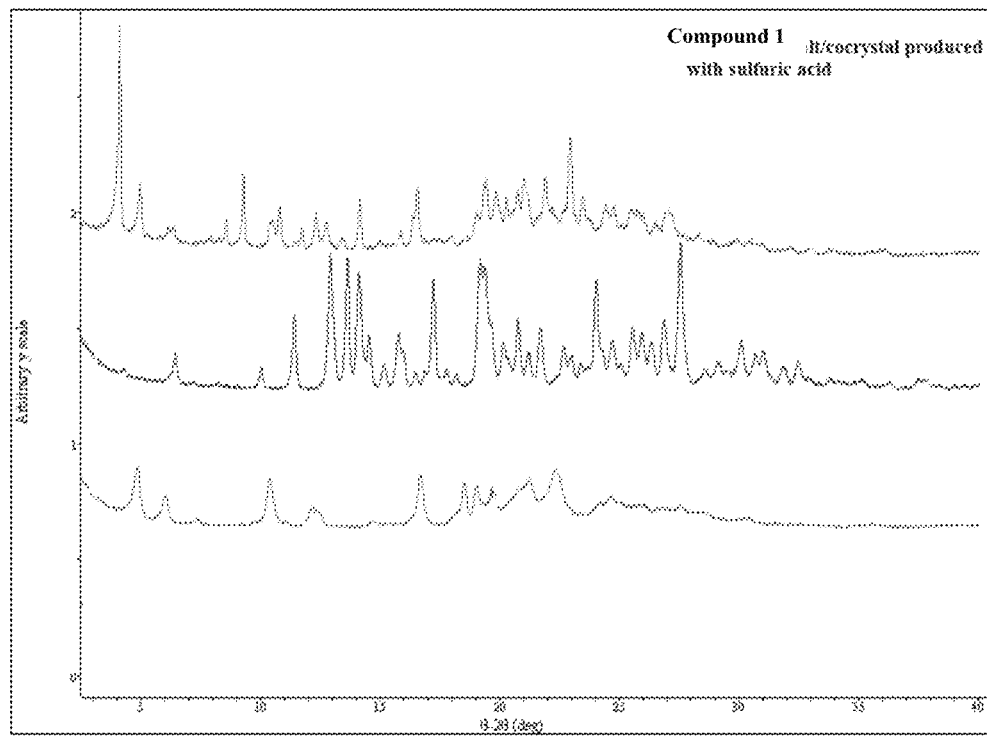
FIG. 2G illustrates X-ray powder diffraction (XRPD) patterns of Compound 1 salt/cocrystal produced with sulfuric acid, prepared according to Example 2.
Figure 2H:
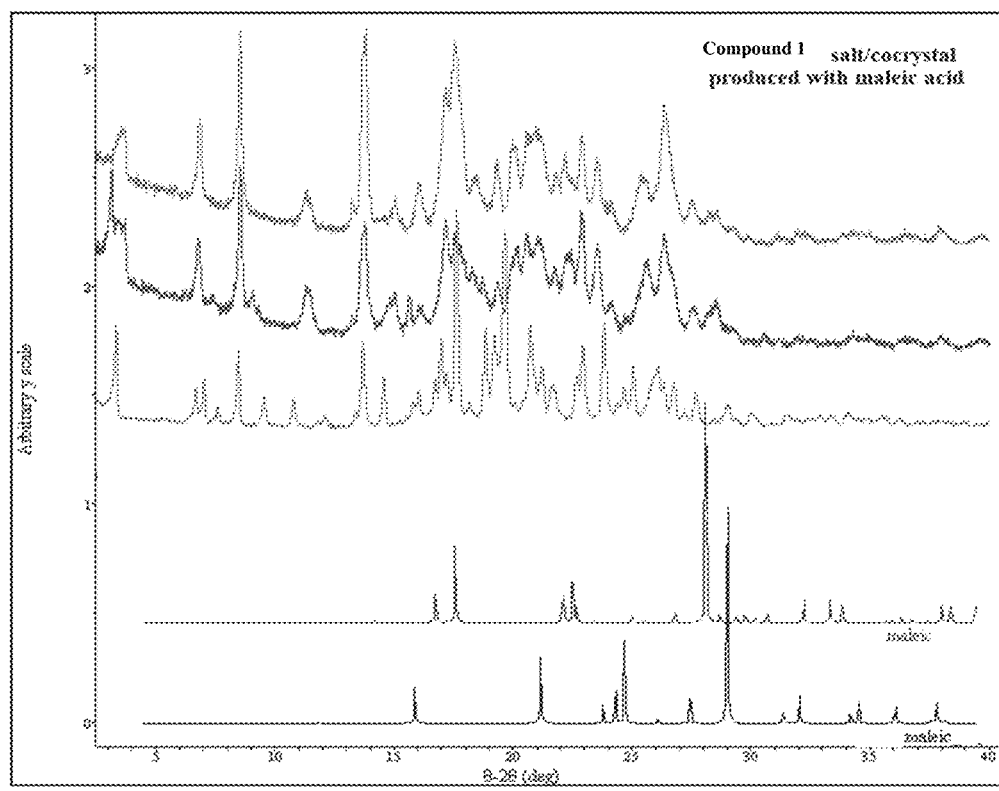
FIG. 2H illustrates X-ray powder diffraction (XRPD) patterns of Compound 1 salt/cocrystal produced with maleic acid, prepared according to Example 2.
Figure 2I:
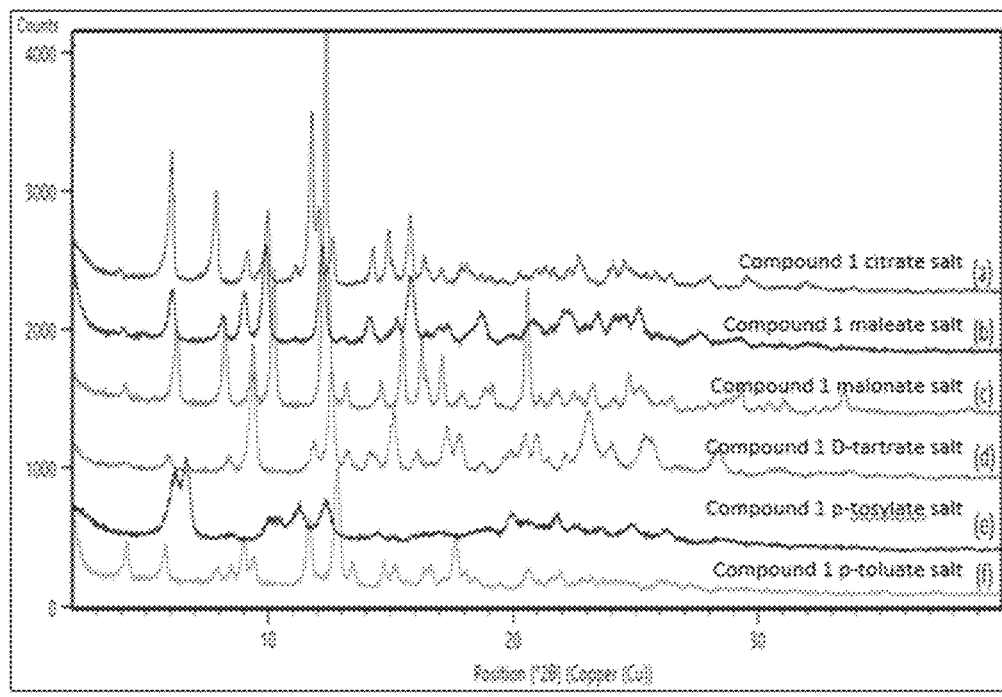
FIG. 2I illustrates X-ray powder diffraction (XRPD) patterns of Compound 1 salt/cocrystal produced with citric acid, maleic acid, malonic acid, D-tartaric acid, p-toluenesulfonic acid, and p-toluic acid.
Figure 2J:
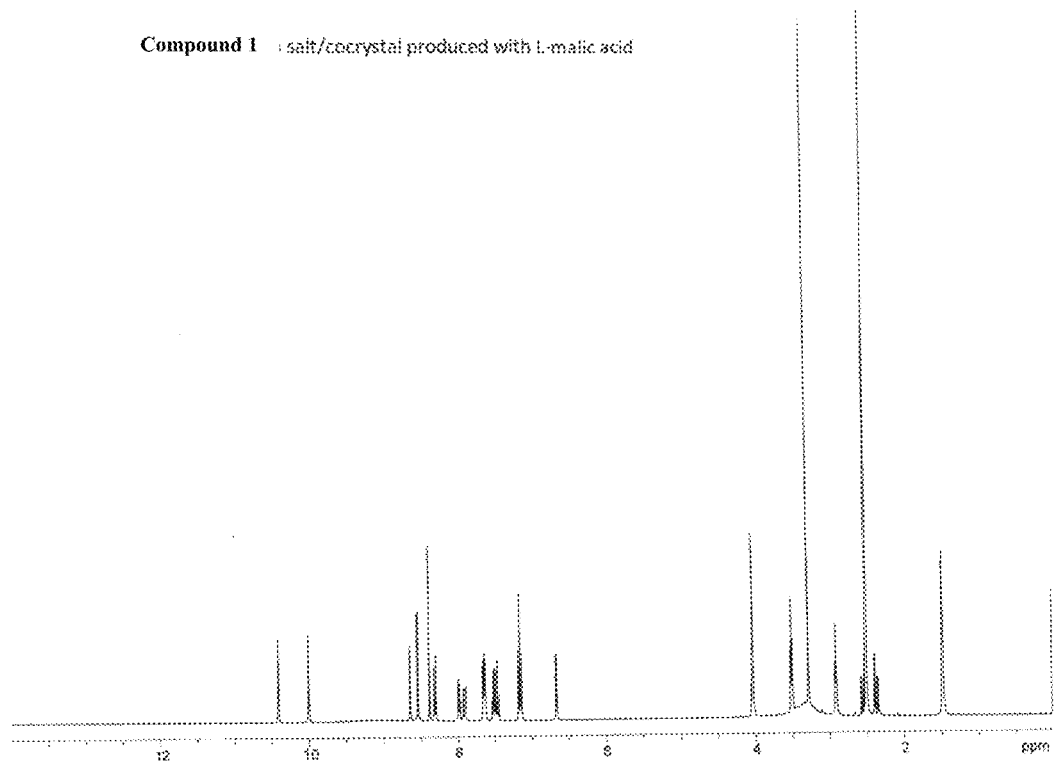
FIG. 2J illustrates a $^1$H-nuclear magnetic resonance ($^1$H-NMR) spectrum of Compound 1 salt/cocrystal produced with L-malic acid, prepared according to Example 2.
Figure 2K:
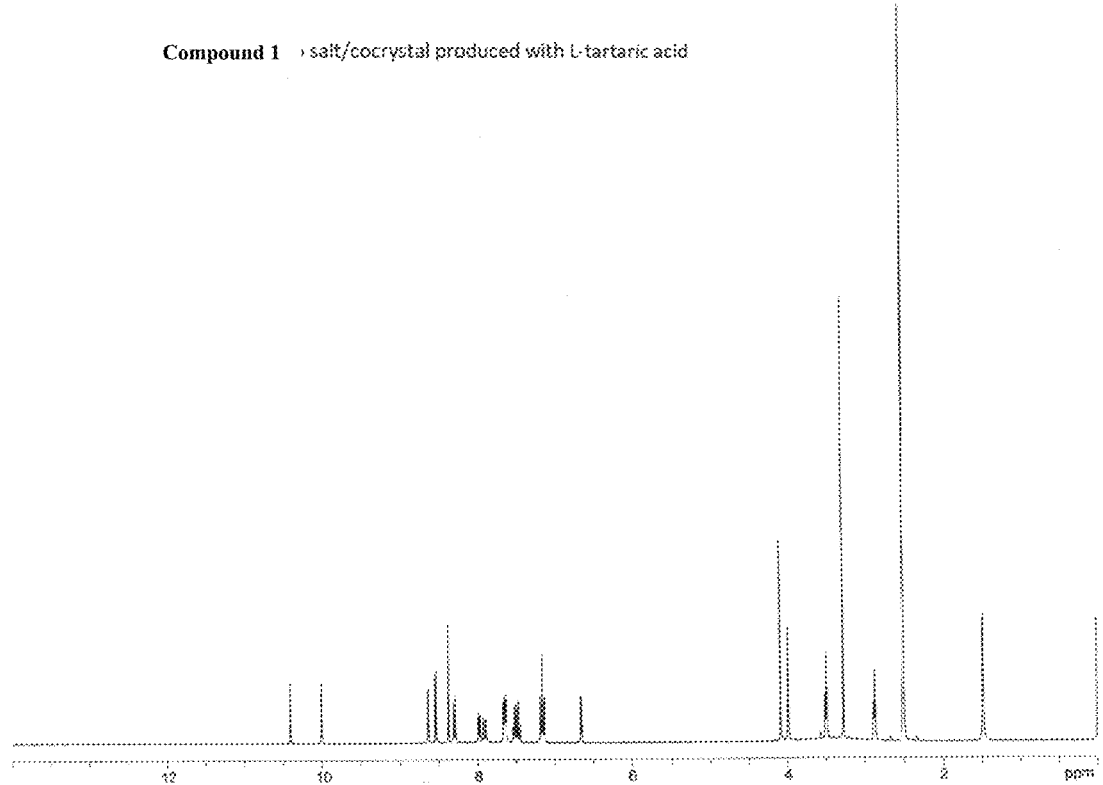
FIG. 2K illustrates a $^1$H-nuclear magnetic resonance ($^1$H-NMR) spectrum of Compound 1 salt/cocrystal produced with L-tartaric acid, prepared according to Example 2.
Figure 2L:
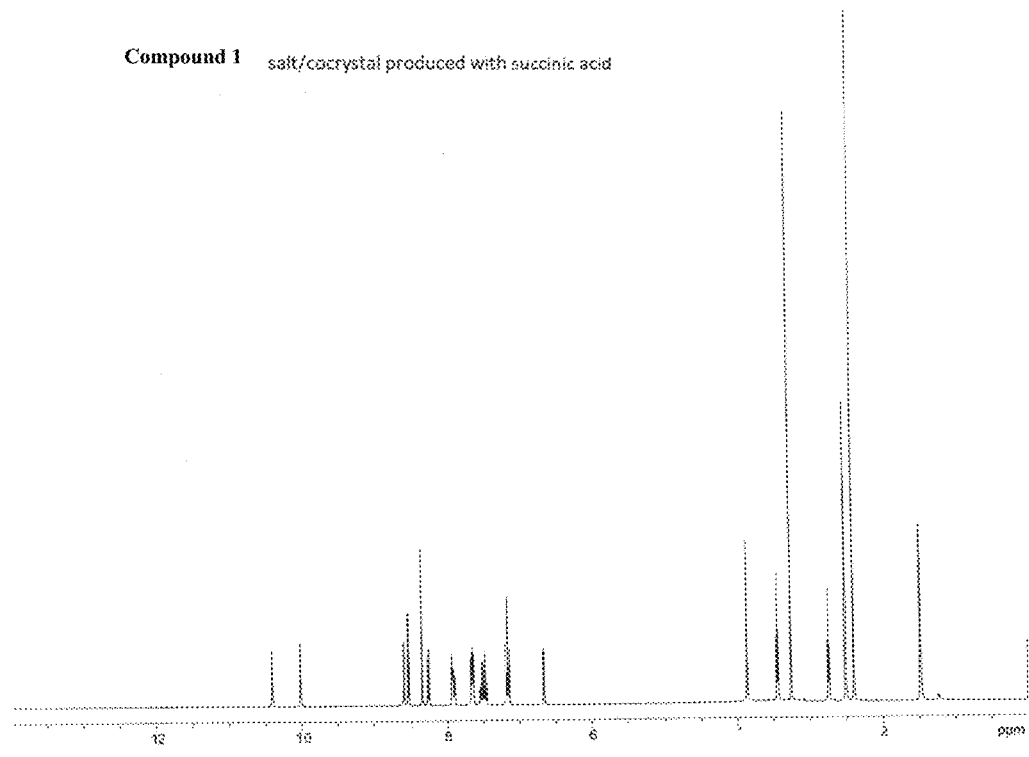
FIG. 2L illustrates a $^1$H-nuclear magnetic resonance ($^1$H-NMR) spectrum of Compound 1 salt/cocrystal produced with succinic acid, prepared according to Example 2.
Figure 2M:
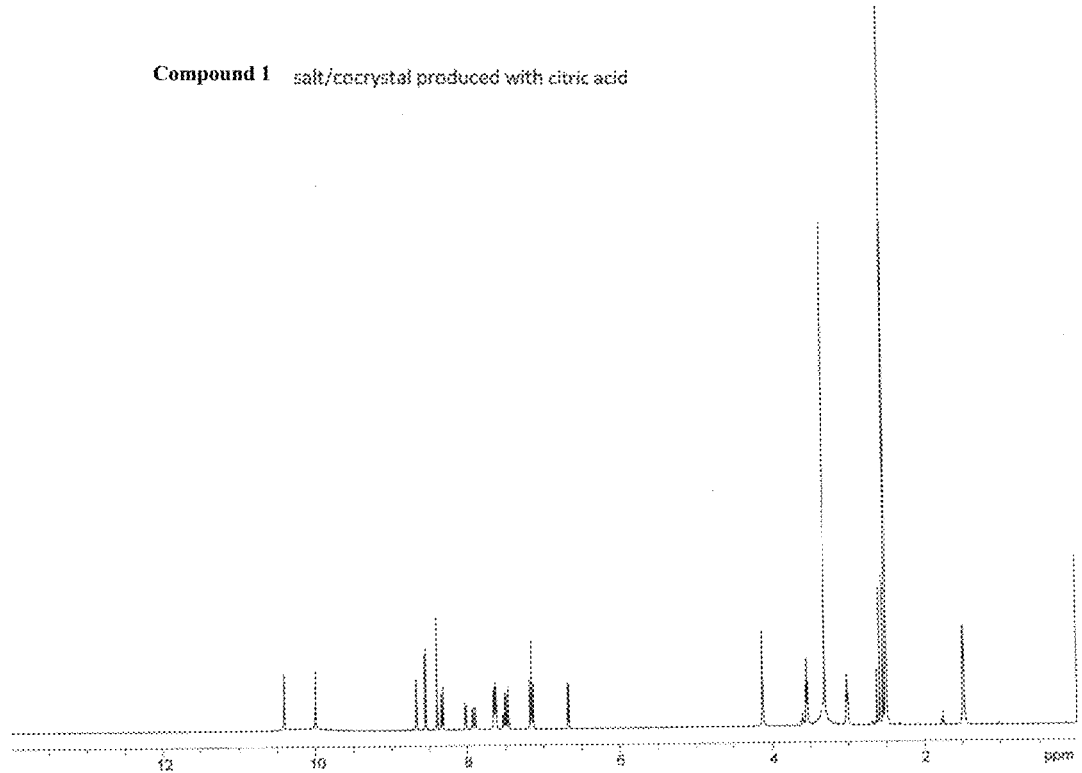
FIG. 2M illustrates a $^1$H-nuclear magnetic resonance ($^1$H-NMR) spectrum of Compound 1 salt/cocrystal produced with citric acid, prepared according to Example 2.
Figure 2N:
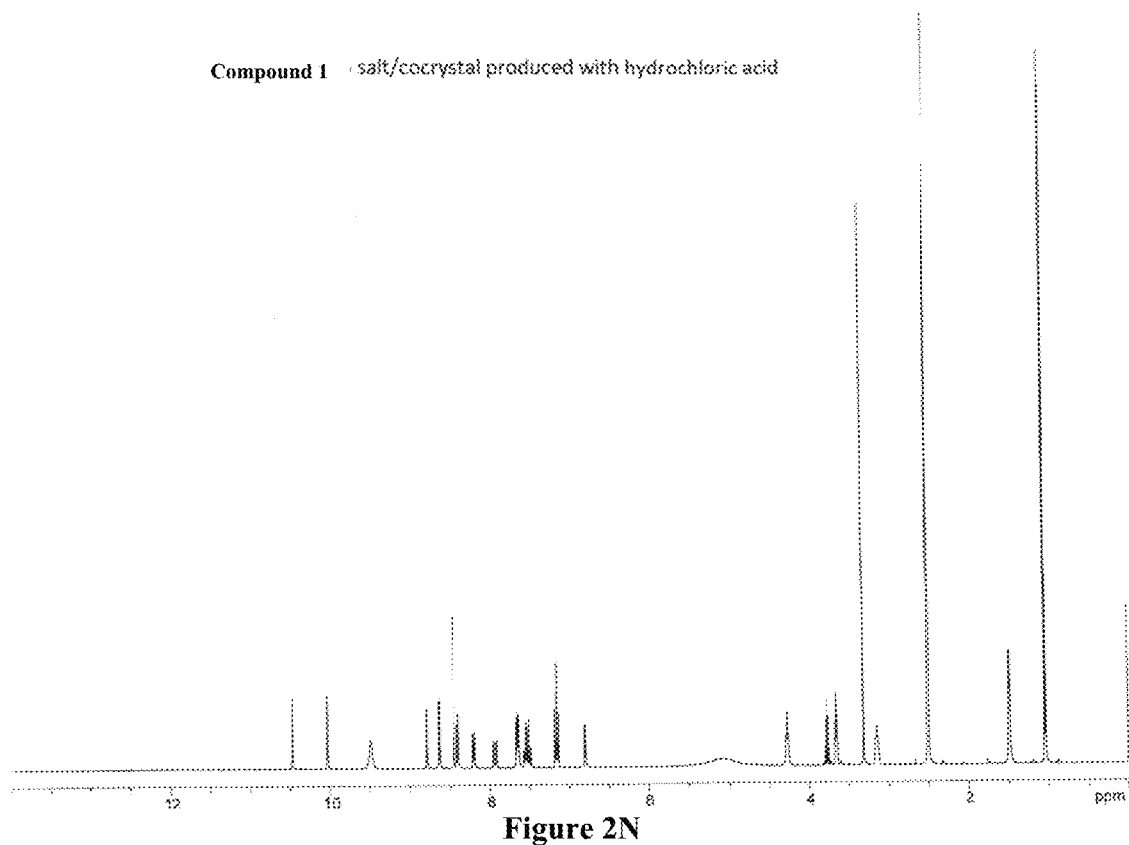
FIG. 2N illustrates a $^1$H-nuclear magnetic resonance ($^1$H-NMR) spectrum of Compound 1 salt/cocrystal produced with hydrochloric acid, prepared according to Example 2.
Figure 2O:
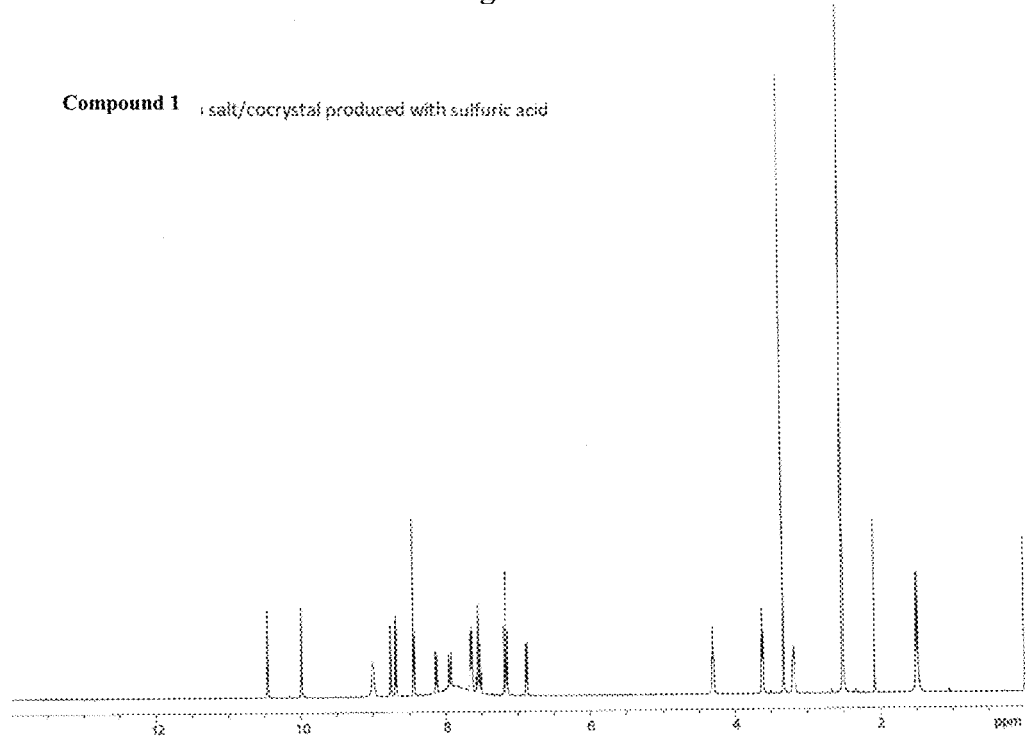
FIG. 2O illustrates a $^1$H-nuclear magnetic resonance ($^1$H-NMR) spectrum of Compound 1 salt/cocrystal produced with sulfuric acid, prepared according to Example 2.
Figure 2P:
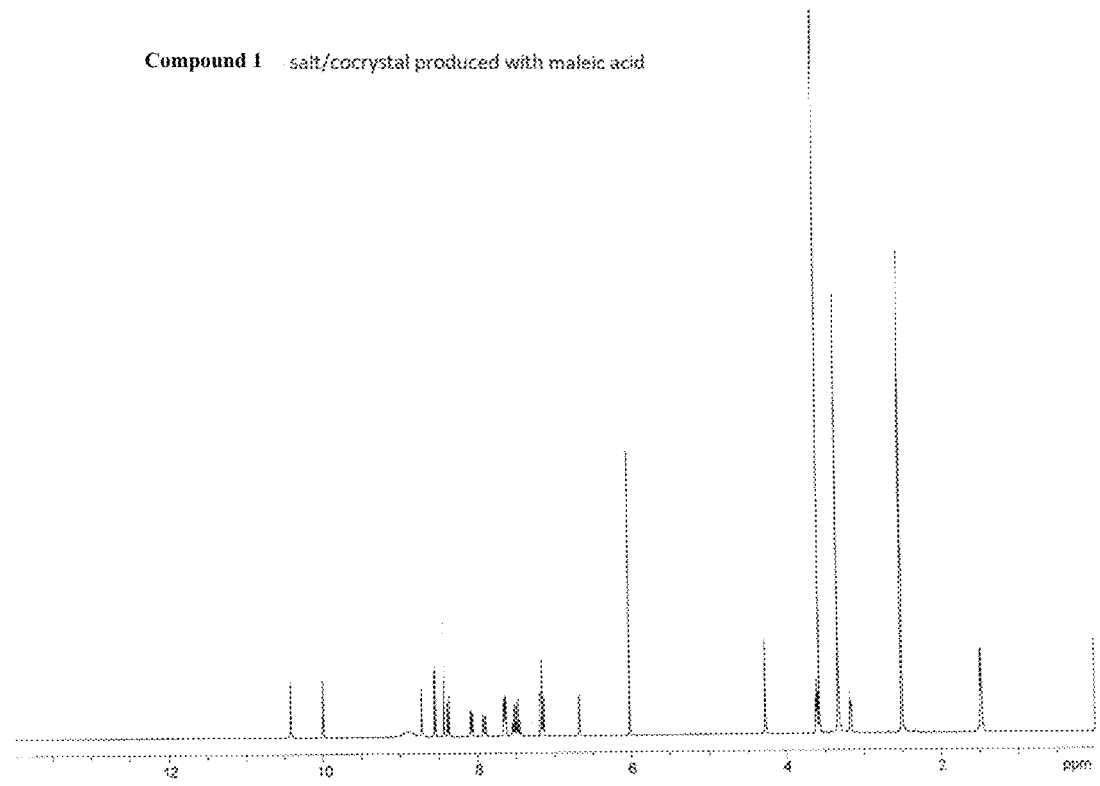
FIG. 2P illustrates a $^1$H-nuclear magnetic resonance ($^1$H-NMR) spectrum of Compound 1 salt/cocrystal produced with maleic acid, prepared according to Example 2.
Figure 2Q:
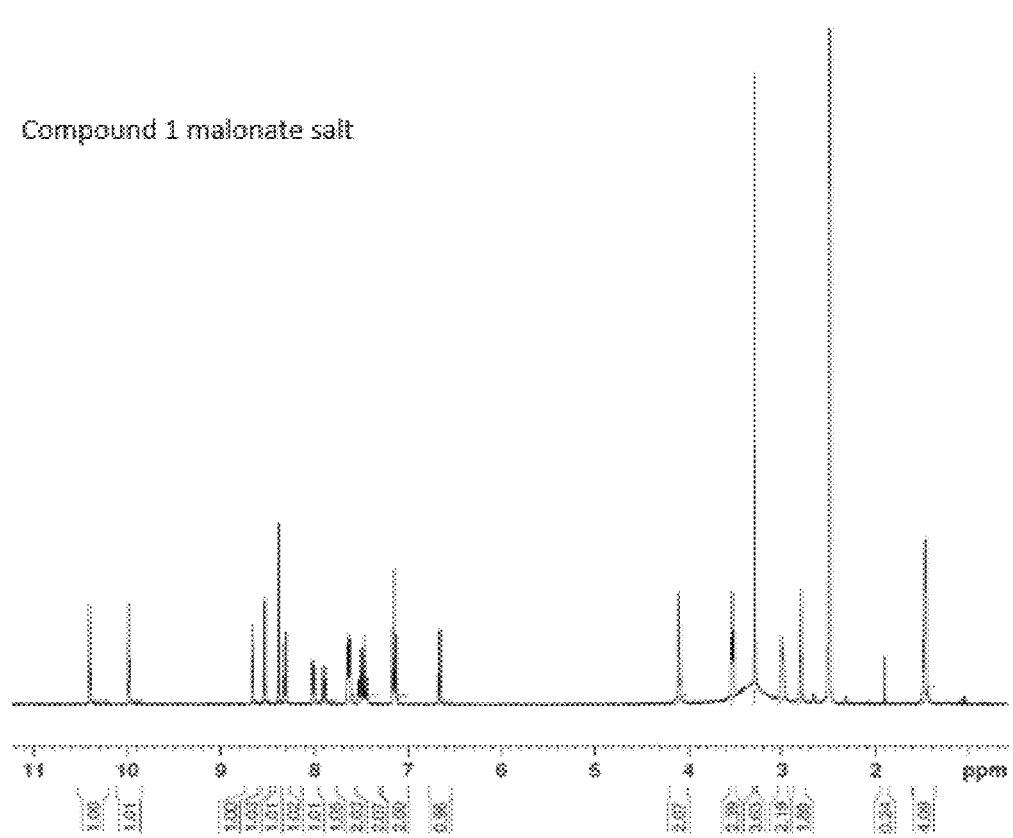
FIG. 2Q illustrates a $^1$H-nuclear magnetic resonance ($^1$H-NMR) spectrum of Compound 1 salt/cocrystal produced with malonic acid.
Figure 2R:
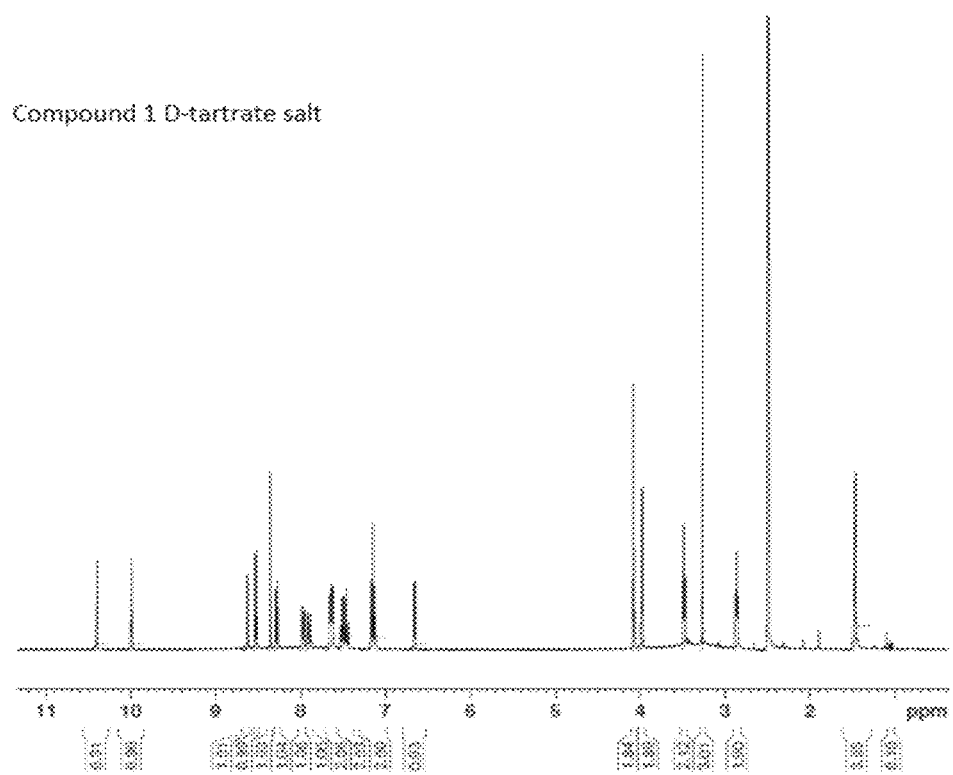
FIG. 2R illustrates a $^1$H-nuclear magnetic resonance ($^1$H-NMR) spectrum of Compound 1 salt/cocrystal produced with D-tartaric acid.
Figure 2S:
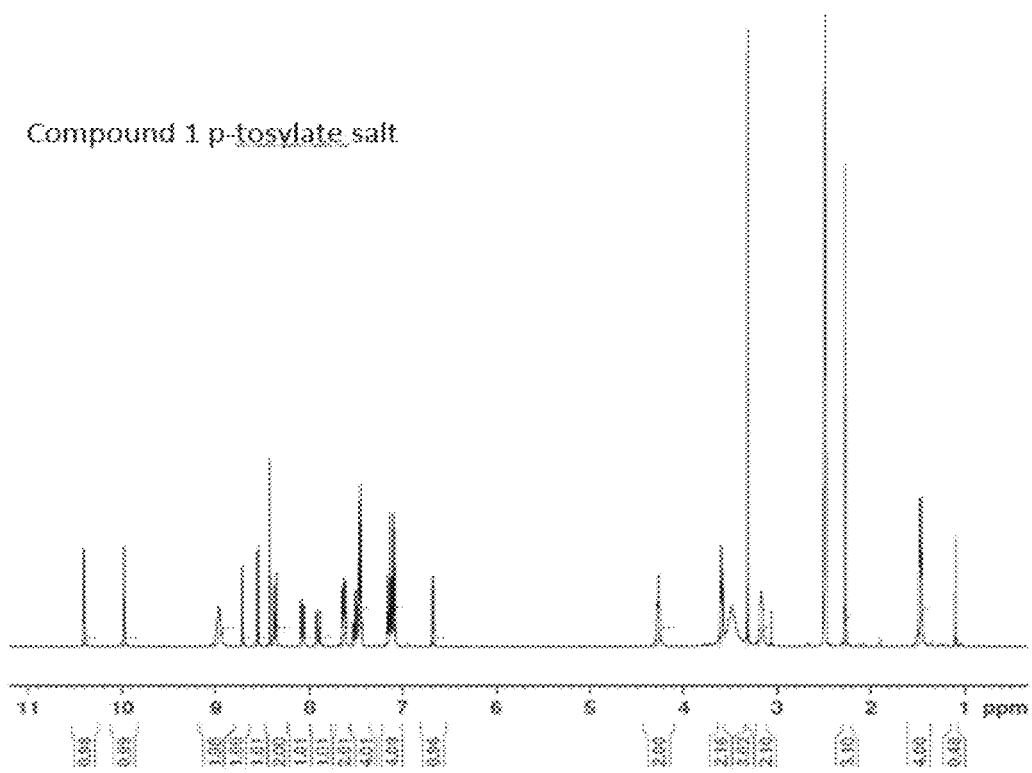
FIG. 2S illustrates a $^1$H-nuclear magnetic resonance ($^1$H-NMR) spectrum of Compound 1 salt/cocrystal produced with p-toluenesulfonic acid.
Figure 2T:
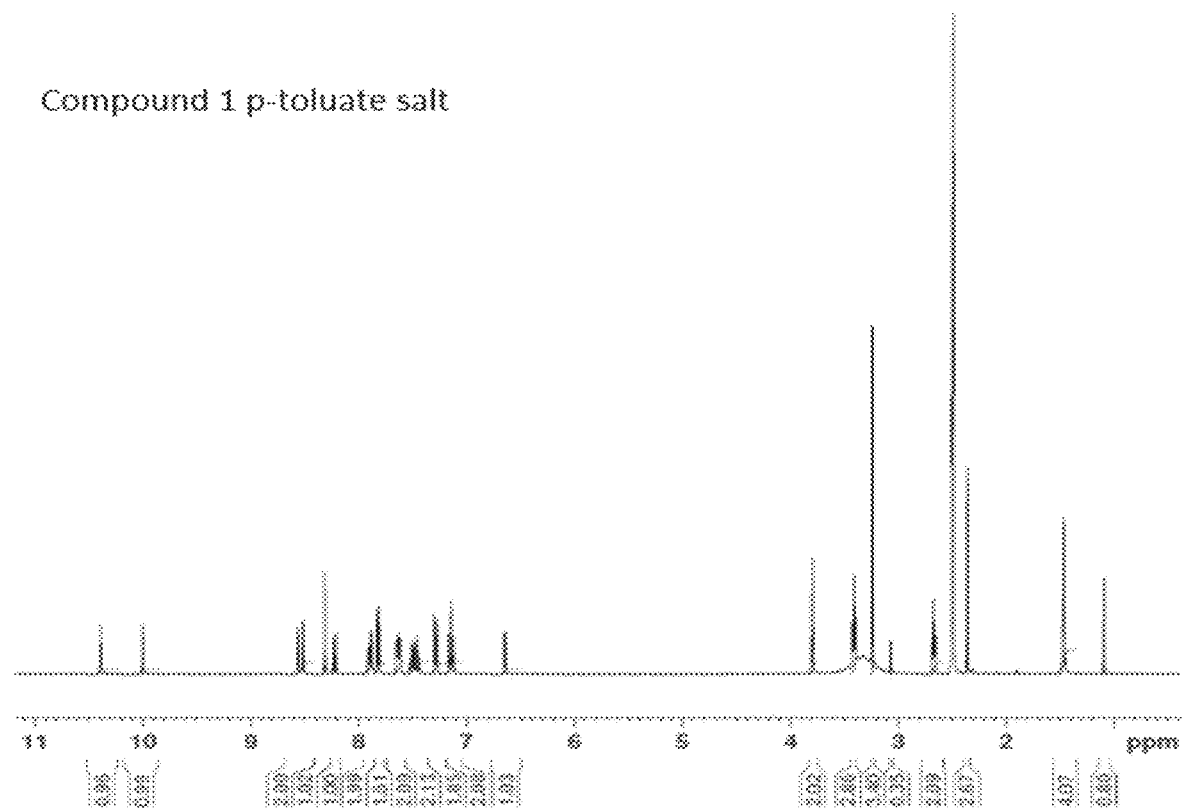
FIG. 2T illustrates a $^1$H-nuclear magnetic resonance ($^1$H-NMR) spectrum of Compound 1 salt/cocrystal produced with p-toluic acid.
Figure 2U:
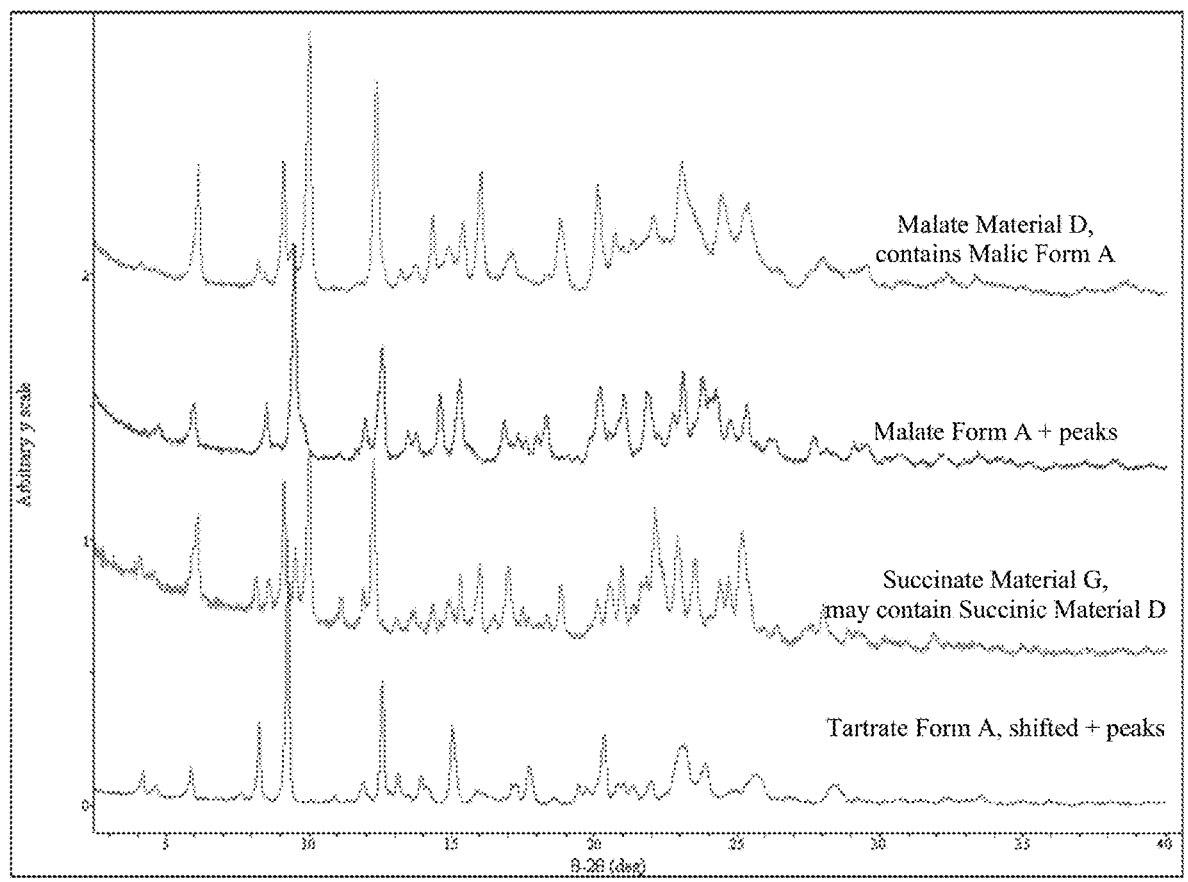
FIG. 2U illustrates X-ray powder diffraction (XRPD) patterns of scaled-up Compound 1 Malate Form A, Malate Material D, Tartrate Form A, and Succinate Material G, prepared according to Example 2.
Figure 2V:
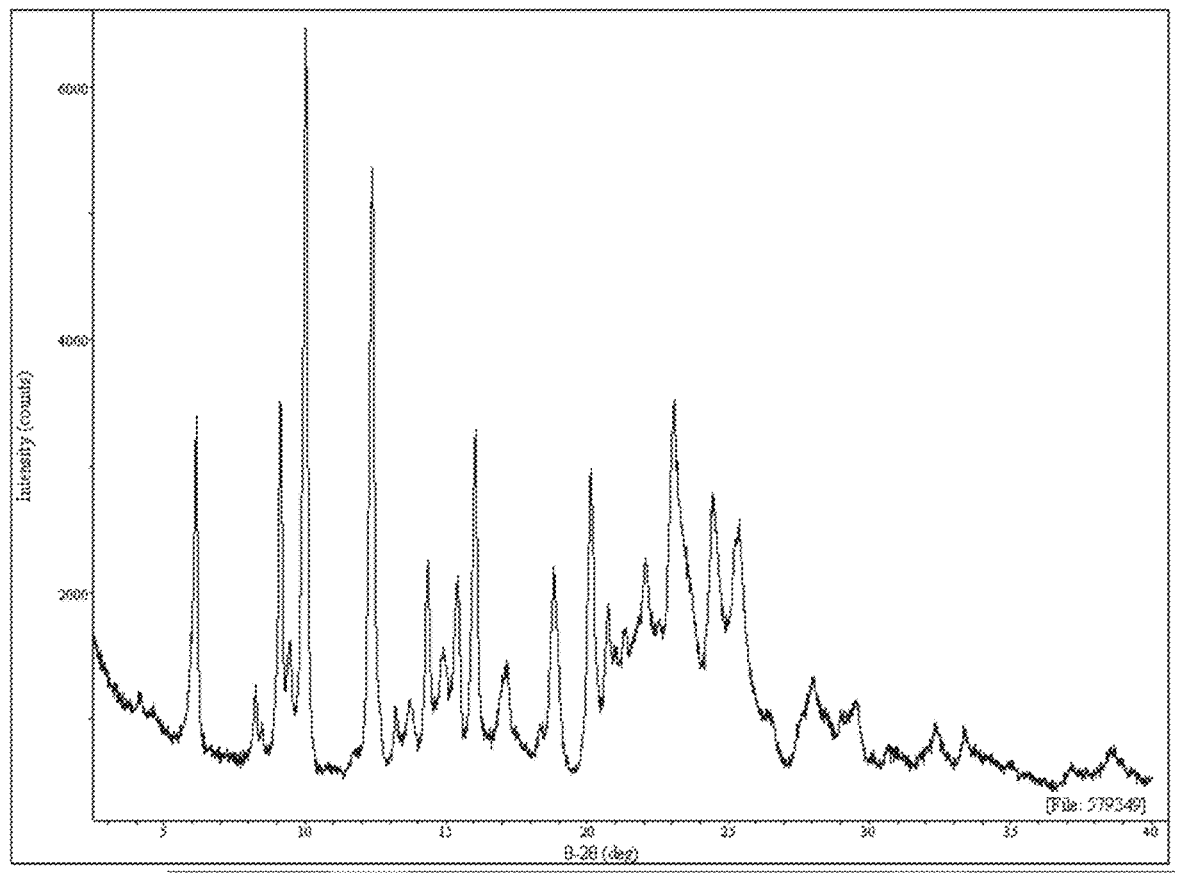
FIG. 2V illustrates an X-ray powder diffraction (XRPD) pattern of Compound 1 Malate Material D prepared according to Example 2.
Figure 2W:
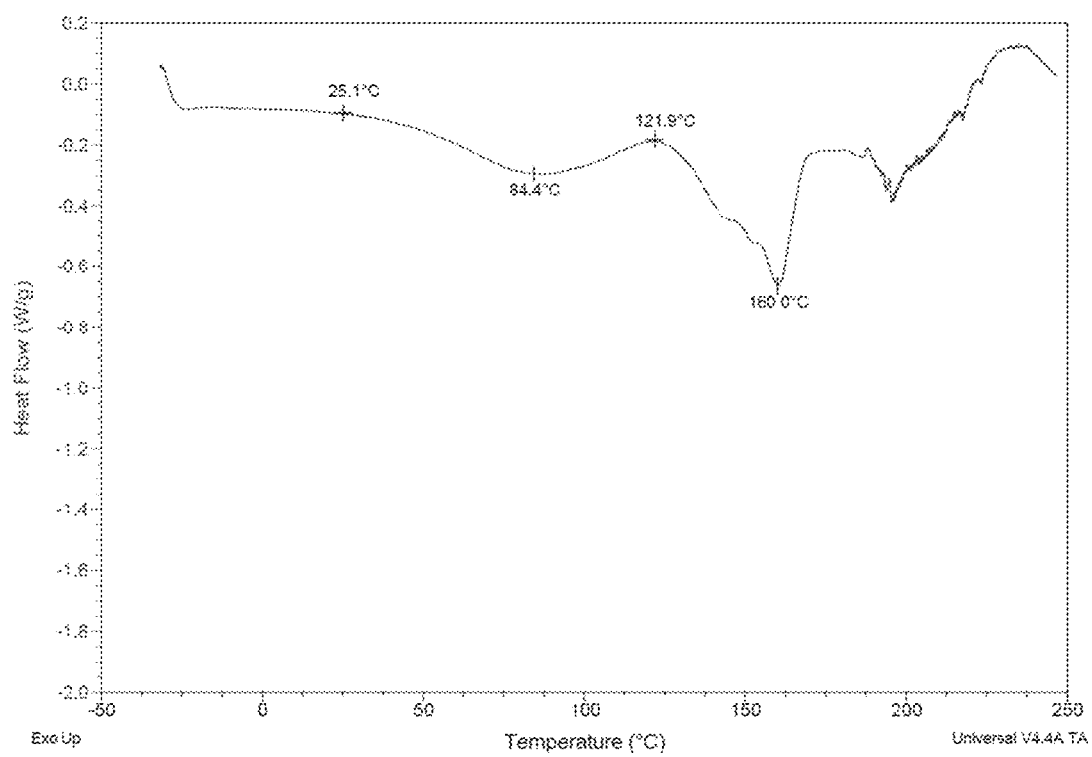
FIG. 2W illustrates a differential scanning calorimetry (DSC) profile of Compound 1 Malate Material D prepared according to Example 2.
Figure 2X:
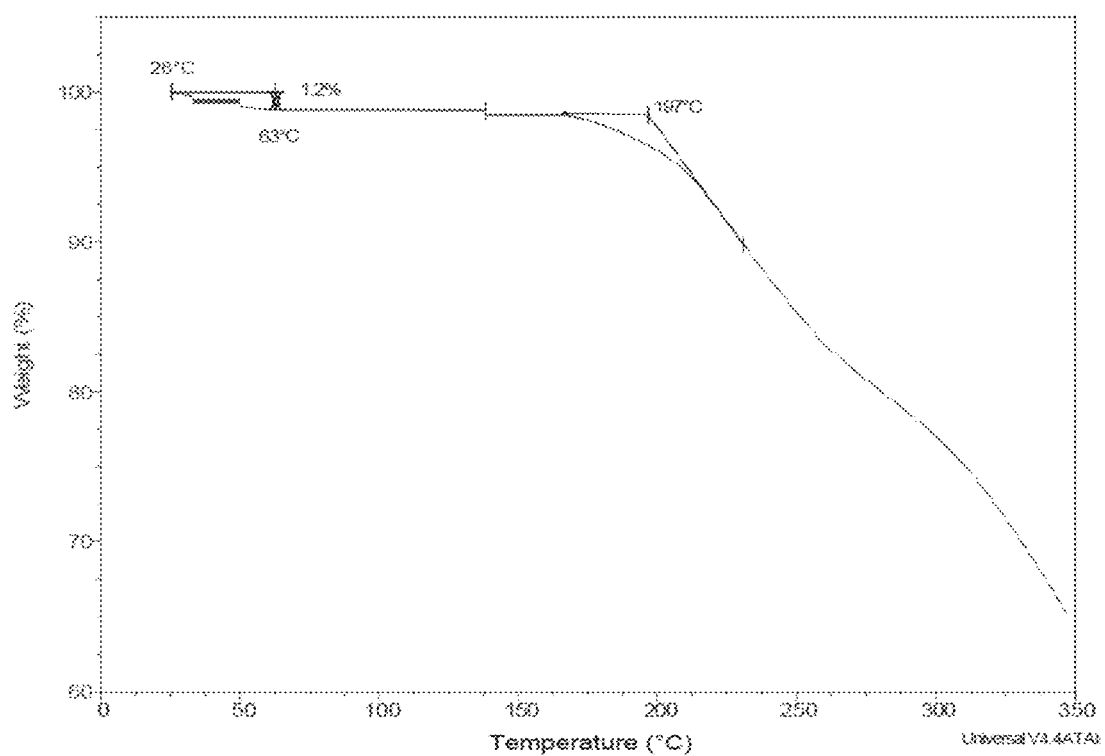
FIG. 2X illustrates a thermogravimetric analysis (TGA) profile of Compound 1 Malate Material D prepared according to Example 2.

The XRPD patterns, DSC and TGA profile of Malate Material D were further shown as FIGS. 2V, 2W and 2X. TGA thermogram showed a loss of volatiles in the 26-63° C. temperature range, which is likely associated with a loss of water, and suggest the sample to be a sesquihydrate with an estimated water loss 3.4 wt %, and the sample exhibits smaller weight loss (~1.2 wt %) possibly due to partial dehydration during storage or due to the use of dry nitrogen during the analysis, and upon further heating the sample displays a sharp loss at ~197° C. (onset) likely due to degradation. DSC thermogram indicates a broad endotherm between ~25° C. and 122° C. (peak maximum at ~84° C.) corresponding to the loss of volatiles observed during the TG analysis and, therefore, likely associated with the release of water, and overlapped endothermic events with an onset at ~122° C. were also observed. And, the XRPD pattern of Malate Materials D is substantially same as that of Malate Form A, but with some shifted peaks.

Figure 2Y:
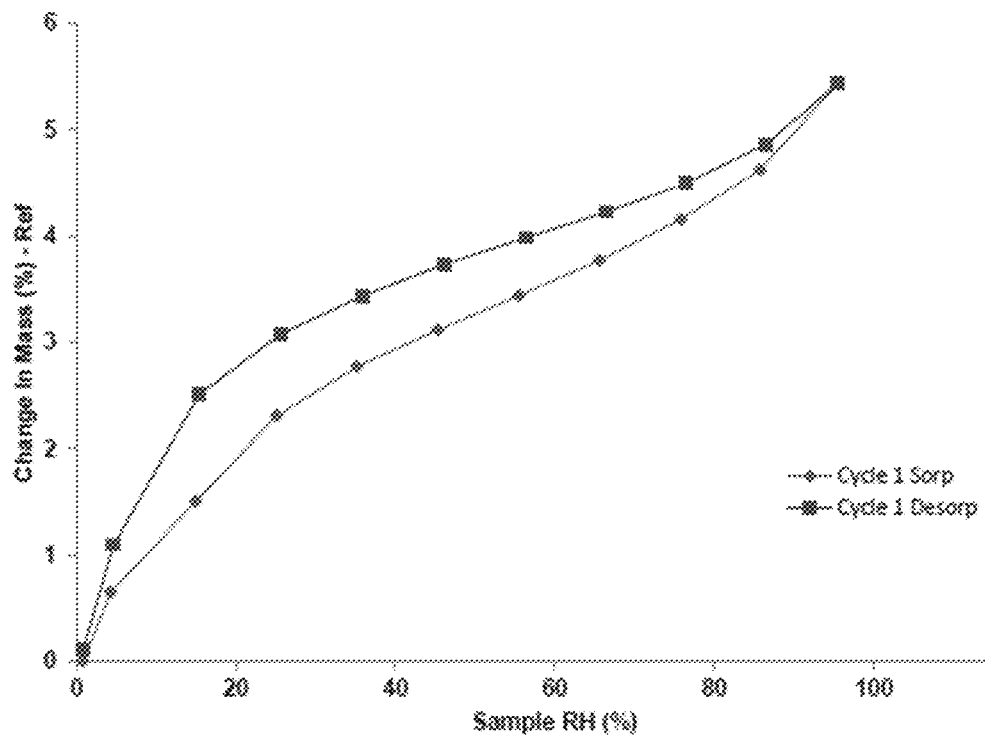
FIG. 2Y illustrates a dynamic vapor sorption (DVS) analysis of Compound 1 Malate Material D prepared according to Example 2.

In addition, based on DVS shown in FIG. 2Y, Malate Material D exhibited a water uptake of ~5.4 wt % (equivalent to ~2.5 mol) over the entire RH range (0-95% RH), which is likely associated with its rehydration to Malate Form A. Upon desorption, the material was observed to lose all the gained moisture with a small hysteresis. Solids after the desorption cycle appeared to be consistent with Malate Material D, based on XRPD data. This is consistent with the expected dehydration during desorption.

Tartrate Form A Obtained

1) The $^1$H NMR spectrum is consistent with Compound 1 containing ~1 mol/mol of tartaric acid, based on the additional peaks near ~4.1 ppm attributable to tartaric counterion and the sample does not exhibit residual organic solvent; 2) the TGA thermogram shows a ~1.9 wt % loss near 25-56° C. associated with a release of volatiles, and sharp weight loss is seen at ~203° C. (onset), typically observed due to degradation; 3) the DSC thermogram exhibits broad endothermic events between at ~25° C. and ~123° C., above which multiple endotherms are observed with peak maxima at ~129° C., and ~189° C.

Succinate Material G Obtained

1) The $^1$H NMR spectrum for the sample is overall consistent with Compound 1 containing ~1 mol/mol of succinic acid, based on additional peaks near ~2.4 ppm, attributable to the counterion, and the sample also contained residual chloroform; 2) the TGA spectrum for the sample shows a loss of volatiles in the 24-116° C. temperature range (—1.1 and ~0.7 wt %), and a sharp weight loss is observed at ~166° C. (onset), likely due to degradation; 3) the DSC thermogram indicates a broad endotherm between ~26° C. and ~102° C. (peak maximum at ~71° C.), corresponding to the loss of volatiles observed during the TG analysis, and above 102° C., the sample exhibits multiple endothems with peak maxima at ~132° C. and ~150° C.

Example 2C Stable Form Screen of Compound 1 Salt/Cocrystal

To attempt an assessment of the most thermodynamically stable form for the L-malic, L-tartaric and succinic salts/cocrystals of Compound 1, the scaled-up materials were triturated in solvent systems with appropriate solubilities for up to one week. Experiments targeting potential hydrates were also performed, mostly under high water activity conditions.

XRPD was used as a primary analytical technique for initial identification of materials obtained with L-malic, L-tartaric, and succinic acids, which are illustrated in FIGS. 2A, 2B and 2C, respectively. The indexing XRPD pattern of Malate Form E is further shown as FIG. 2A(e). The conditions and results of the stable form screens are summarized in Table 2C.

TABLE 2B

Scale-Up of Compound 1 salts /Cocrysatals

| Salt Former | | Conditions (a) | Observation (b) | XRPD Results |
|---|---|---|---|---|
| L-malic Acid (Up to 2 gram scale) | 1 | Dissolved free base in IPA at 78° C., mixed with 1.1 eq. acid (warm solution in IPA) (clear). Stirred at 78° C. for 10 mins. Slowly cooled to RT with stirring (precipitation), reheated to 78° C. (solids remained), seeded with Malate Material D. Slurried at 78° C. for 15 mins. Slowly cooled to RT, filtered in vacuum,, washed with IPA and EtOH, dired in a vacuum oven at 40° C., overnight. | Unknown morphology, opaque aggregates, some birefringence and extinction (c) | Malate Form A + peaks |
| | 2 | Dissolved free base in EtOH at 60° C. Mixed with 1.2 eq. acid (warm solution in EtOH) (clear). Stirred at 60° C. for 30 mins. Slowly cooled to RT with stirring, added more EtOH. Slurried at RT, overnight. Filtered in vacuum washed with EtOH, placed into a vacuum oven at RT for 3 days. (the conditions nearly identical to the conditions shown to be successed in producing malate Form A from Example 2A) | Unknown morphology, possibly very small needles, birefringence and extinction | Malate Material D (close to C), contains Malate Form A |
| L-tartaric acid (1 gram scale) | 1 | Dissolved free base in EtOH at 60° C. Mixed with 1.2 eq. acid (warm solution in EtOH) (clear, then precipitation). Slurried at 60° C. for 6 hours, added more EtOH. Slowly cooled to RT with stirring, slurried, overnight. Filtered in vacuum, washed with EtOH, placed into a vacuum oven at RT For 3 days. | Very small needles, birefringence and extinction | Tartrate Form A shifted + additional peaks |
| Succinic acid (1 gram scale) | 1 | Dissolved free base in chloroform. Mixed with 1.2 eq. acid (solution in MeOH) (clear). Stirred at RT for 30 min. Concentrated solution by evaporation ~1/2 of total volume (precipitation). Slurried at RT, overnight. Filtered in vacuum, washed with DEE, placedplaced into a vacuum oven at RT for 3 days. | — | Succinate Material G, may contain Succinic Material D |

(a) Temperature, duration of experiments, amounts recovered and yields are approximate.
(b) Microscope observations performed in mineral oil unless otherwise specified.
(c) No mineral oil was used.

TABLE 2C

Stable Form Screening Experiments

| Starting material | # | Solvent, Conditions (v/v) | Observation | XRPD Results |
|---|---|---|---|---|
| Malate Form A | 1 | EtOAc, 40° C. | Unknown morphology, opaque aggregates, minor birefringence and extinction | Malate Form A |
| | 2 | IPA, 40° C. | Unknown morphology, opaque aggregates, minor birefringence and extinction | Malate Form A |
| | 3 | MeOH, RT | Unknown morphology, opaque aggregates, minor birefringence and extinction | Malate Form A |
| | 4 | $CH_3NO_2$/MeOH (60/40), RT | Unknown morphology, opaque aggregates, minor birefringence and extinction | Malate Form A |
| | 5 | Acetone/water (75/25), RT | Unknown morphology, opaque aggregates, minor birefringence and extinction | Malate Form A |
| | 6 | Water, 40° C. | Unknown morphology, opaque aggregates, some birefringence and extinction | Malate Form A + small peaks |
| | 7 | TFE, RT | Unknown morphology, opaque aggregates, minor birefringence and extinction | Malate Form E + peaks |
| | 8 | THF/water (90/10), RT | Unknown morphology, opaque aggregates, minor birefringence and extinction | Malate Material F + peaks |
| | 9 | ACN/water (75/25), RT | Unknown morphology, opaque aggregates, minor birefringence and extinction | Malate Material G, contains Malic Form A |
| | 10 | Dioxane/water (80/20), RT | Unknown morphology, opaque aggregates, minor birefringence and extinction | Malate Form A, contains Malate Material J |
| Tartrate Form A | 1 | IPA, 40° C. | Unknown morphology, birefringence and extinction | Tartrate Form A |
| | 2 | Acetone/water (30/70) | Unknown morphology, some birefringence and extinction | Tartrate Form A |
| | 3 | Dioxane/water (30/70) | Unknown morphology, some birefringence and extinction | Tartrate Form A |
| | 4 | THF/water (75/25) | Unknown morphology, some birefringence and extinction | Tartrate Form A |
| | 5 | EtOAc, 40° C. | Unknown morphology, some birefringence and extinction | Tartrate Form A, shifted |
| | 6 | ACN/water (60/40) | Unknown morphology, no birefringence and extinction | Tartrate Form A, shifted + peaks |
| | 7 | Acetone/DMF (33/66) | Unknown morphology, some birefringence and extinction | Tartrate Material D |
| | 8 | Water, 40° C. | Unknown morphology, some birefringence and extinction | Tartrate Material D, contains Tartrate Form A |
| | 9 | EtOAc/DMF (50/50) | Unknown morphology, some birefringence and extinction | Tartrate Material E |
| | 10 | EtOH/DMF (30/70) | Unknown morphology, no birefringence and extinction | Tartrate Material E |
| | 11 | DMF/heptane (50/50) | Unknown morphology, some birefringence and extinction | Tartrate Material F, contains Tartrate Material B |

Example 3

Evaluation of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide Malate Form A (Compound 1 Malate Form A)

Example 3A Critical Relative Humidity

Critical relative humidity (RH) experiments were designed to confirm the physical stability RH range for Malate Form A in the solid-state. A mixture of Malate Form A/Malate Material H, and samples of Malate Form A, Malate Material B, Malate Material C, and Malate Material D were tested at selected RH conditions (see Table 3A(1)). The water content of Malate Form A and Material D were characterized by Karl Fischer analysis. (See Table 3A(2)).

Experiments were carried out by exposing solids of the test materials to various RH conditions. Preparation of specimens for XRPD analyses of post-stress solids was conducted with minimal exposure to ambient conditions. For selected samples, Karl Fischer analysis was done concurrently with XRPD testing. These samples therefore were kept in a glove bag equilibrated at the RH near to the exposure conditions, and the XRPD specimens were prepared inside the glove bag.

A mixture of Malate Form A/Malate Material H was subjected to 0%, 11%, 23%, 69%, and 93% RH, each for approximately 5 days. It should be noted that the stress RH was not maintained during the XRPD specimen preparation and analyses. Therefore, solids from all these stress conditions were briefly exposed to ambient RH estimated as ~21-23% at the time of the analyses.

Solids stressed at 23% RH were still composed of Malate Form A/Malate Material H mixture. However, the amount of Malate Material H appeared to decrease in the stressed sample compared to the original, based on the relative intensities of the XRPD peaks. Solids stressed at 69% and 93% RH were consistent with Malate Form A with improved crystallinity. Malate Material H was no longer observed in these samples indicating its conversion to Malate Form A at elevated RH.

XRPD analysis of solids stressed at or below 11% RH indicated dehydration of Malate Form A. The XRPD patterns after the exposure to 0% and 11% RH showed peaks attributable to Malate Material C and Material D, respectively, and contained Malate Form A.

Malate Materials C and D were suspected to be lower hydrates. Both materials exhibited XRPD patterns similar to each other and to Malate Material B, another potential lower hydrate or an unstable anhydrous material. Upon re-exposure of Malate Materials C and D to 75% RH for ~5 days, conversion to Malate Form A was observed for both materials. This demonstrates that the dehydration of Malate Form A is reversible under the conditions tested.

Based on these results, Malate Form A was confirmed to be physically stable above 23% RH, below which a reversible dehydration was seen. While remaining the same form within the specified RH range, Malate Form A from various samples exhibited shifts of the XRPD peaks. This suggested Malate Form A could be a variable hydrate. For variable hydrates, the amount of water accommodated within crystal lattice varies without a form change.

To investigate this further, stress experiments were conducted at 30% and 93% RH with minimal exposure to ambient RH so that XRPD and water content analyses could be considered representative of the stress conditions. For this purpose, the RH exposure and the preparation of XRPD specimens were conducted in a glove bag with the following assumptions: 1) the glove bag maintained a tight seal throughout the duration of each experiment, 2) the entire glove bag maintained the same humidity without any "pockets" of higher or lower humidity, 3) the polymer film used for XRPD specimens maintained a tight seal throughout XRPD analysis, and 4) the exposure of the sample to ambient conditions during the preparation for Karl Fischer analyses was brief and did not significantly affect the water content. In these experiments, a mixture of Malate Form A/Malate Material H was initially subjected to 93% RH for ~8 days. It was then immediately analyzed by XRPD and Karl Fischer. The same sample was then re-exposed to 30% RH.

As expected from the critical RH study, both samples were consistent with Malate Form A, based on XRPD data. It should be noted that the peaks in the XRPD pattern of the sample exposed to 93% RH were consistently shifted towards lower angles compared to the peaks of the sample from the 30% RH exposure. Such shifts are indicative of expansion of the crystal lattice due to accommodation of a larger amount of water, and are consistent with a higher water content of Malate Form A after exposure to high humidity. In particular, Malate Form A was found to contain 5.3% of water (equivalent to ~2.5 mol) after the 93% RH stress, while the water content of the sample after the 30% RH stress was measured as 3.7% (equivalent to ~1.5 mol). Peak shifts in XRPD for Malate Form A were observed, consistent with Malate Form A being a variable hydrate. And, Malate Form A may contain about 1.5~2.5 moles $H_2O$.

TABLE 3A (1)

Relative Humidity and Heat Stress of Compound 1 L-Malate

| Starting Form/Material | # | Conditions (a) | XRPD Results |
|---|---|---|---|
| Malate Form A/Malate Material H | 1 | 0% RH, RT, 5 days (~25% ambient RH at sample preparation) | Malate Material D, contains Malate Form A |
| | 2 | 11% RH, RT, 5 days. (~23% ambient RH at sample preparation) | Malate Material C, contains Malate Form A |
| | 3 | 23% RH, RT, 5 days. (~23% ambient RH at sample preparation) | Malate Form A (slightly improved crystallinity), contains some Malate Materials. |
| | 4 | 69% RH, RT, 5 days. (~21% ambient RH at sample preparation) | Malate Form A shifted (c) (improved crystallinity) |
| | 5 | 93% RH, RT, 5 days. (~21% ambient RH at sample preparation) | Malate Form A shifted (c) (improved crystallinity) |
| | 6 | 93% RH, RT, 8 days. (~92-95% ambient RH at sample preparation) (b) | Malate Form A, slight peak shifts (c) |
| Malate Form A | 1 | 30% RH, RT, 4 days. (~33% ambient RH at sample preparation) (b) | Malate Form A, slight peak shifts (c) |
| | 2 | 93% RH, RT, 1 day. | Malate Form A, some peaks slightly shifted (b) |
| Malate Material D, contains Malate Form A | 1 | 75% RH, RT, 5 days. (~15% ambient RH at sample preparation) | Malate Form A shifted (c) |

TABLE 3A (1)-continued

Relative Humidity and Heat Stress of Compound 1 L-Malate

| Starting Form/Material | # | Conditions (a) | XRPD Results |
|---|---|---|---|
| Malate Material C, contains Malate Form A | 1 | 75% RH, RT, 5 days. (~15% ambient RH at sample preparation) | Malate Form A shifted (c) |
| Malate Material B | 1 | 75% RH, RT, 6 days. | Malate Form A, increased disorder |

(a) Temperature, % RH, and duration of experiments are approximate.
(b) Specimen for XRPD analysis was prepared in a glove bag equilibrated at specified RH. Samples for Karl Fischer analysis were prepared with minimal exposure to ambient RH.
(c) Peak shifts for Malate Form A are consistent with the material being a variable hydrate.

TABLE 3A(2)

Physical Characterization of of Compound 1 L-Malate

| Sample | KF Analytical Technique | Results |
|---|---|---|
| Malate Form A | ~12% RH at sample preparation | Calculated H2O content: 3.47% (average value from 2 runs- 3.61%, 3.33%) |
| | ~17-18% RH at sample preparation, ~35 seconds for prepation | Calculated H2O content: 3.73% (average value from 2 runs- 3.74%, 3.72%) |
| | ~35-36% RH at sample preparation, ~35 seconds for prepation | Calculated H2O content: 5.32% (average value from 2 runs- 5.30%, 5.35%) |
| Malate Material D, contains small amount of Malate Form A | ~16-17% RH at sample preparation, ~40 seconds for preparation | Calculated H2O content: 0.67% (average value from 2 runs- 0.77%, 0.58%) |

Example 3B Heat and Elevated Temperature/Relative Humidity Stress

Heat and elevated temperature/RH stresses were designed to evaluate the physical stability of Compound 1 Malate Form A at elevated temperature. A mixture of Compound 1 Malate Form A/Malate Material H was utilized for testing. Experiments were conducted by heating solids of the test material at 40, 80, 120, and 140-145° C. Solids were also subjected to a combination of elevated temperature and RH, i.e. 40° C./75% RH and 30° C./60% RH (Table 3B).

As previously seen at lower RH, heating Compound 1 Malate Form A at or above 40° C. resulted in its partial dehydration. The XRPD patterns of the solids stressed for 7 days at 40° C. and 80° C., and at or above 120° C. for ~1 hour were primarily composed of Compound 1 Malate Material C or Malate Material D, both suspected lower hydrates of the salt. Peaks attributable to Malate Form A were still observed in the patterns.

Samples stressed at 40° C./75% RH and 30° C./60% RH for one day were composed of Malate Form A and no longer showed Malate Material H.

TABLE 3B

Relative Humidity and Heat Stress of Compound 1 Malate

| Starting Form/Material | # | Conditions (a) | XRPD Results |
|---|---|---|---|
| Malate Form A/Malate Material H | 1 | 40° C./75% RH, 1 day | Malate Form A, some peaks slightly shifted (b) |
| | 2 | 30° C./60% RH, 1 day | Malate Form A, some peaks slightly shifted (b) |

(a) Temperature, % RH, and duration of experiments are approximate.
(b) Peak shifts for Malate Form A are expected as a variable hydrate.

Example 3C Critical Water Activity/Solvate Formation

An evaluation of the physical stability of Malate Form A under solvent-mediated conditions and assessment of the potential competition between solvate and hydrate formation were conducted by slurrying Malate Form A in various organic solvent/water systems (Table 3C).

An acetone/water system was selected for investigation of the stability at water activities between 0.4 and 0.9. Aqueous ACN, Dioxane, DMF, DMSO, and NMP were also investigated. A mixture of Malate Form A/Malate Material H was primarily used as the starting material. Samples of Malate Form A were combined and utilized as the starting material in a single experiment (acetone/water at low water activity).

No form change was observed for Malate Form A after slurry in acetone/water at water activities of ~0.8 and ~0.9. Based on XRPD, solids from both experiments appeared to be composed of Malate Form A, and no longer contained Malate Material H. This indicated the physical stability of Malate Form A in acetone/water systems with high water activity and conversion of Malate Material H under these conditions.

Slurrying in acetone/water at water activities at or below 0.7 generated mixtures of Malate Material B and Malate Form A. It should be noted that the amount of Malate Material B in the slurried solids may depend on the presence of Malate Material H in the starting material. In particular, based on the experiment at water activity of 0.3, the amount of Malate Material B appeared to be higher in the sample of Malate Form A/Malate Material H mixture used and was lower in the sample Malate Form A used. In this study, Malate Material B was found to rehydrate to Malate Form A after a 75% RH stress, based on XRPD data.

All other aqueous mixtures containing organic solvents other than acetone produced materials that appeared to be unique and were likely solvated. They were new crystalline materials and designated as Malate Materials L through P. These results were consistent with the previously proposed competition between solvates and Malate Form A that depends on solvent and water activity. Indeed, slurrying at water activity of 0.8 in NMP/water led to a complete conversion of Malate Form A to a unique material (designated Malate Material O), while increasing the water activity to 0.9 in the same solvent system resulted only in partial conversion, and the sample still contained Malate Form A.

TABLE 3C

Water Activity Slurries for Compound 1 Malate

| Starting Material | Solvent/ Duration (a) | Water Activity (aw) | XRPD Results |
|---|---|---|---|
| Malate Form A (b) | Acetone/H2O 98/2 1 week | 0.35 | Malate Form A + Malate Material B |
| Malate Form A/ Malate Material H | Acetone/H2O 98/2 1 week | 0.35 | Malate Material B, contains Malate Form A |
| | Acetone/H2O 96/4 1 week | 0.50 | Malate Form A + Malate Material B |
| | Acetone/H2O 93/7 1 week | 0.62 | Malate Form A, contains a small amount of Malate Material B |
| | Acetone/H2O 89/11 1 week | 0.71 | Malate Material B |
| | Acetone/H2O 80/20 2 weeks | 0.82 | Malate Form A (some disorder) |
| | Acetone/H2O 50/50 2 weeks | 0.91 | Malate Form A (some disorder) |
| | ACN/H2O 85/15 2 weeks | 0.92 | Malate Material G + Malate Form A, shifted (c) |
| | Dioxane/H2O 90/10 2 weeks | 0.64 | Malate Material J, shifted |
| | DMF/H2O 70/30 2 weeks | 0.50 | Malate Material M + peaks (similar to Malate Material N) |
| | DMF/H2O 50/50 2 weeks | 0.70 | Malate Material M |
| | DMSO/H2O 80/20 2 weeks | 0.27 | Malate Material N |
| | DMSO/H2O 70/30 2 weeks | 0.42 | Malate Material N |
| | NMP/H2O 50/50 2 weeks | 0.79 | Malate Material O |
| | NMP/H2O 25/75 2 weeks | 0.93 | Malate Material O + Malate Form A |

(a) Organic solvents were dried over molecular sieves prior to use. Temperature, solvent ratio (v/v), and duration of experiments are approximate
(c) Peak shifts for Malate Form A are expected as a variable hydrate.

Example 3D Crystallization Experiments
Compound 1 Malate Form A

Preliminary crystallization experiments targeting the pure phase of Compound 1 Malate Form A were conducted to search for more suitable and controllable crystallization conditions. Several of these experiments used acetone/water, the solvent system in which Compound 1 Malate Form A showed physical stability at certain water activities. Techniques such as cooling, evaporation, and slurry were utilized in the experiments. Details are provided in Table 3D.

Of these experiments, crystalline Compound 1 Malate Form A was generated from slow cooling in acetone, slow cooling in EtOH, and slow cooling in acetone/MeOH followed by sub-ambient crystallization. Disordered Malate Form A was produced by slurry in acetone/water or water. The remaining solvent systems produced unique materials that often contained Malate Form A. Based on XRPD, the most crystalline sample of Malate Form A was generated from the slow cool in acetone/MeOH followed by sub-ambient crystallization.

TABLE 3D

Crystallization Experiments for Compound 1 Malate Form A

| Starting Material | Solvent system | | Conditions (a) | Observations | XRPD Results |
|---|---|---|---|---|---|
| Malate Form A/ Malate Material H | Acetone | 1 | Added solvent and heated at 70° C.; continued adding aliquots of pre-heated solvent at elevated temperature. Separated into two parts. Slowly cooled part 1 from 70° C. to RT. | Unknown morphology, very small; birefringence/ extinction + transparent pieces | Malate Form A, shifted (b) |
| | | 2 | Hot-filtered part 2 obtained above into a new, pre-heated vial. Slowly cooled form 70° C. to RT (radial clusters of dendritic needles; birefringence/extinction). Transferred to sub-ambient (2-8° C.). | Insufficient amount of solids | — |
| | Acetone/FFO 50/50 | 1 | Slurried at RT for 6 days (seeded with Malate Form A) | — | Malate Form A (some disorder) |
| | | 2 | Slowly cooled from 55-60° C. to RT (seeded with Malate Form A at elevated temperature) | Aggregates of small particles with unknown morphology; birefringence/extinction | Malate Form A + Malate Material L |
| | | 3 | Added Acetone then H²O (clear). Slowly evaporated at RT. | Discontinued | — |
| | Acetone/H₂O 75/25 | 1 | Slurried at RT for 3 days. Volume reduction at RT; then slurried at RT for1 day. | Unknown morphology; birefringence/ extinction | Malate Form A + Malate Material U |
| | Acetone/MeOH 59/41 | 1 | Added Acetone and heated at 70° C. Added pre-heated MeOH at elevated temperature (clear). Slowly cooled from 70° C. to RT (aggregates of small fines + needles; birefringence/extinction). Transferred to sub-ambient (2-8° C.). | Clusters of dendritic needles; birefringence/ extinction | Malate Form A |
| | ACN/MeOH 44/56 | 2 | Added ACN and heated at 60° C. (solids remained). Added MeOH at elevated temperature (mostly clear). Fast cooled from 60° C. to RT (clear). Transferred to sub-ambient (2-8° C.). | No solids | — |
| Malate Form A/ Malate Material H | 1-BuOH | 1 | Added solvent and heated at 70° C.; continued adding aliquots of pre-heated solvent at elevated temperature (slightly cloudy, then clear). Separated solution into two parts, part 1 and part 2. Slowly cooled part 1 from 70° C. to RT (radial clusters of dendritic needles; birefringence/extinction). | Unknown morphology, small particles; birefringence/ extinction | Malate Material Q |

TABLE 3D-continued

Crystallization Experiments for Compound 1 Malate Form A

| Starting Material | Solvent system | | Conditions (a) | Observations | XRPD Results |
|---|---|---|---|---|---|
| | | 2 | Transferred to sub-ambient (2-8° C.). Hot-filtered the part 2 obtiaend above into a new, pre-heated vial. Slowly cooled from 70° C. to RT (dendritic needles and fines + radial clusters; birefringence/extinction). Transferred to sub-ambient (2-8° C.). | Very small fines + needles; birefringence/ extinction | Similar to Malate Form E, small peak shifts (b) |
| | Dioxane/H2O 90/10 | 1 | Fast evaporated at 60° C. | Unknown morphology; birefringence/ extinction | Malate Material J |
| | DMF/H2O | 1 | Solvent/Anti-solvent precipitation attempt at RT (clear). Transferred to sub-ambient (2-8° C.). Isolated solids via vacuum filtration while still cold; stored in fridge. | Unknown morphology, very small particles; birefringence/ extinction | Malate Material L, disordered |
| | EtOH | 1 | Added solvent and heated at 55° C. Heat increased to 65-70° C.; added aliquots of pre-heated solvent at elevated temperature (slightly cloudy). Separated into two parts, part 1 and part 2. Slowly cooled part 1 from 70° C. to RT. | Unknown morphology; birefringence/ extinction | Malate Form A |
| | | 2 | Hot-filtered the part 2 obtiened above into a new, pre-heated vial. Slowly cooled from 70° C. to RT (clear). Transferred to sub-ambient (2-8° C.). | Unknown morphology, small particles; birefringence/ extinction | Malate Material K + peak |
| Malate Form A/ Malate Material H | EtOH/H2O 50/50 | 1 | Added solvent and heated at 60° C. (clear). Hot-filtered into a pre-heated vial; slowly cooled from 70° C. to RT. | Unknown morphology; birefringence/ extinction | Malate Material G, shifted (b) + Malate Form A |
| | EtOH/H2O 70/30 | 1 | Fast cooled from 60° C. to RT. Kept at RT. | Insufficient amount of solids | — |
| | H2O | 1 | Slurried at RT for 1 day. | Unknown morphology; birefringence/extinction | Malate Form A, disordered |
| | IPA/H2O 80/20 | 1 | Fast cooled form 60° C. to RT. Decanted solvent; analyzed damp solids. | Radial clusters of tiny needles; birefringence/extinction | Malate Material P |
| | MeOH | 1 | Added solvent and heated at 65-70° C. Added aliquots of pre-heated solvent at elevated temperature (clear). Slowly cooled from 70° C. to RT (solids present). Transferred to sub-ambient (2-8° C.). | Insufficient amount of solids | — |
| | MeOH/EtOAc | 1 | Solvent/Anti-solvent precipitation attempt, 60° C. to sub-ambient (ice bath) (clear). Transferred to sub-ambient (2-8° C.). | No solids | — |
| | THF/heptane | 1 | Solvent/Anti-solvent precipitation, 60° C. to RT (solids immediately precipitated, then clumped together). Slurried at RT. | Discontinued | — |
| Malate Material J | Acetone/H2O 50/50 | 1 | Slurried at RT for 4 days. | Unknown morphology; birefringence/ extinction | Similar to Malate Material L, disordered |

TABLE 3D-continued

Crystallization Experiments for Compound 1 Malate Form A

| Starting Material | Solvent system | | Conditions (a) | Observations | XRPD Results |
|---|---|---|---|---|---|
| Malate Material J | Acetone/H2O 50/50 | 1 | Slurried at RT for 4 days. | — | Malate Material G |
| Malate Form A + Malate Material L | Acetone/H2O 50/50 | 1 | Slurried at RT for 4 days. | — | Malate Form A + Malate Material L |
| Supernatant from the solution generating Malate Form A | Acetone/H2O 50/50 | 1 | Supernatant from the solution generating Malate Form A (produced from a mixture of Malate Form A/Malate Material H in Acetone/H2O 50/50 2 weeks) in Table 3B. Fast evaporation at RT. | Unknown morphology, very small particles; birefringence/extinction | Malate Material L, shifted (b) |
| Supernatant from the solution generating Malate Material J | Dioxane/H2O 90/10 | 1 | Supernatant from the solution generating Malate Material J (produced from a mixture of Malate Form A/Malate Material H in Dioxane/H2O 90/10 2 weeks) in Table 3B. Fast evaporation at RT. | Unknown morphology, small particles; faint birefringence/extinction | Malate Material J |
| Supernatant from the solution generating Malate Material M | DMF/H2O 50/50 | 1 | Supernatant from the solution generating Malate Material M (produced from a mixture of Malate Form A/Malate Material H in DMF/H2O 50/50 2 weeks) in Table 3B. Fast evaporation at RT. | Insufficient amount of solids | — |
| Supernatant from the solution generating a mixture of Malate Material O + Malate Form A | NMP/H2O 25/75 | 1 | Supernatant from the solution generating a mixture of Malate Material O + Malate Form A (produced from a mixture of Malate Form A/Malate Material H in NMP/H2O 25/75 2 weeks) in Table 3B.. Fast evaporation at RT. | Insufficient amount of solids | — |

(a) Temperatures, solvent ratios (v/v), and duration of experiments are approximate.
(b) Peak shifts for Malate Form A were expected as a variable hydrate.
Peak shifts for Malate Material G are relative to those in Example 2. Peak shifts for Malate Material L are relative to those in the previous sample of Malate Material L (disordered) in Table 3C.

Example 4

Stability and In Vivo Studies of N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide malate salt (Compound 1 Malate Form A)

Example 4A: Stability of Compound 1 Malate Form A

Long term stability studies for Compound 1 Malate Form A were conducted at 2-8° C. and 25° C./60% RH. For each test interval, samples are packaged into double polyethylene bags, individually zip tied and stored in 30 mL white screw cap HDPE bottles.

Stability data through 24 months are provided in Table 4A. Results shows that Compound 1 Malate Form A is stable after 24 months storage at 2-8° C. or 25° C./60% RH, after 6 months storage at 40° C./75% RH, after 12 months storage at 40° C./75% RH.

TABLE 4A

Stability of Compound 1 Malate Form A

Related Impurities (HPLC): Total impurities/%

| Form | 2-8° C. Time/month | | | | | 25° C./60% RH | | | | |
|---|---|---|---|---|---|---|---|---|---|---|
| | 0 | 3 | 6 | 12 | 24 | 0 | 3 | 6 | 12 | 24 |
| Compound 1 Malate Form A | 0.86 | 0.87 | 0.79 | 0.78 | 0.80 | 0.86 | 0.76 | 0.83 | 0.80 | 0.90 |

Example 4B: Compound 1 Malate Form A Exhibits Improved PK Parameters Compared to Compound 1 Free Base Amorphous in the Presence of Surfactant The following Example illustrates that Compound 1 Malate Form A, exhibits a two-fold improvement in Pharmacokinetic (PK) parameters and in vivo bioavailability compared to formulations of Compound 1 containing Tween-20.

Methods (1) Animals

Three male and three female purebred beagle dogs (non-naïve) per group were used to test animals for pharmacokinetic experiments to examine each formulation. The animals were acclimated to study conditions for 3 days prior to initial dose administration and were housed in accordance with all applicable laws, regulations and guidelines of the Institutional Animal Care and Use Committee (IACUC). At initial dosing, the animals weighed 6.6 to 10.8 kg and were young adult/adult in age.

(2) Dosing

For Phase 1, individual doses were administered on a fixed-dose basis of 20 mg/day. Doses were administered orally, followed by a 10 mL flush with water to help ensure swallowing.

For Phase 2, individual doses were administered on a fixed basis of 2 mg/day IV (single dose). A single dose was administered by bolus intravenous injection, followed by a flush with approximately 2 mL of saline.

On each day of dosing (all groups), animals were fasted for approximately 1 hour prior to treatment. And food was returned approximately 1 hour post dose.

(3) Sample Collection and Analysis

For each phase, blood (approximately 1 mL) was collected from a jugular vein into tubes containing $K_2EDTA$ predose and at approximately 0.5, 1, 2, 4, 6, 8, 12, 24, and 48 hours postdose.

Blood was maintained in chilled cryoracks prior to centrifugation to obtain plasma. Centrifugation began within 1 hour of collection. Plasma was placed into 96-well tubes with barcode labels. Plasma was maintained on dry ice prior to storage at approximately −70° C.

Samples were analyzed using an established liquid chromatography/mass spectrometry (LC-MS/MS) method.

Results

Figure 3A:
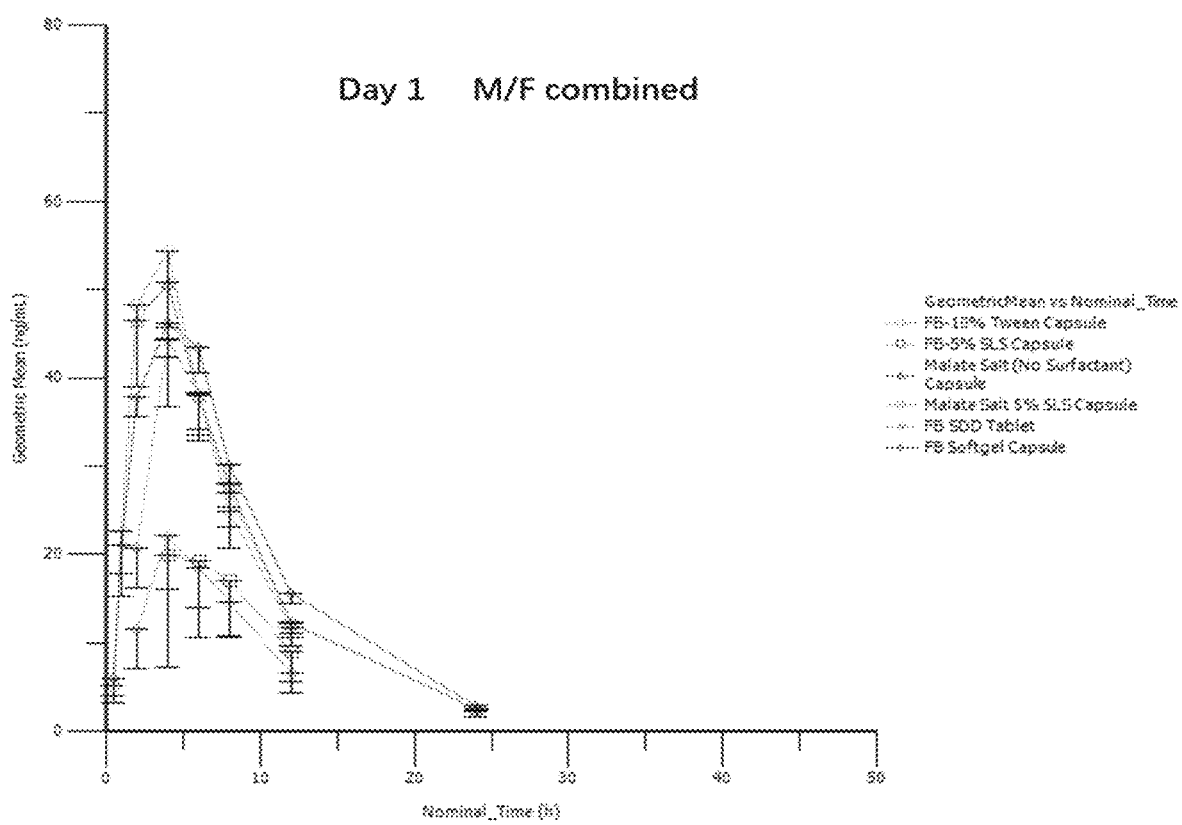
FIG. 3A illustrates a comparison of mean plasma concentration profile with time in beagle dogs for Compound 1 administered as capsules and tablets of Compound 1 free base compared to Compound 1 L-malate capsules.

The results of the comparison of the oral dosing of Compound 1 Malate Form A and Compound 1 free base amorphous in Tween-20 after a single dose at 20 mg/kg or solutions of each dosed intravenously at 2 mg/kg are show in Table 4B and FIG. 3A. The absolute bioavailability of Compound 1 Malate Form A and Compound 1 amorphous in Tween-20 is shown in Table 4C.

TABLE 4B

Comparison of Oral and Intravenous Exposure Levels of Compound 1 Malate Form A and Compound 1 Amorphous in Tween-20

| Day | Route | Dose (mg/day) | Phase | Formulation | DN $AUC_{0\text{-}inf}$ [h*ng/ml/(mg/day)] |
|---|---|---|---|---|---|
| 1 | Oral | 20 | 1 | Compound 1 Malate Form A (No surfactant) Capsule | 21.4 |
| | Oral | 20 | 1 | Compound 1 Amorphous + 10% Tween 20 Capsule | 11.2 |
| | IV | 2 | 2 | Compound 1 Malate Form A Solution | 62.6 |
| | IV | 2 | 2 | Compound 1 Amorphous + 10% Tween 20 Solution | 69.1 |

TABLE 4C

Absolute Bioavailability of Orally Administered Compound 1 Malate Form A and Compound 1 Amorphous in Tween-20

| | Formulation | DN $AUC_{0\text{-}inf}$ [h*ng/ml/(mg/day)] |
|---|---|---|
| Absolute Bioavailability (%) (DN AUC [Oral]/DN AUC [IV]) * 100 | Compound 1 Malate Form A | 34.2 |
| | Compound 1 Amorphous + 10% Tween 20 | 16.2 |

These data demonstrate that the Compound 1 Malate Form A exhibits a 2-fold improvement in oral bioavailability in dogs, in the absence of surfactant, compared to the amorphous of Compound 1 free base plus surfactant. Whereas, IV dosing of the two formulations results in similar in vivo exposure demonstrating that the Compound 1 Malate Form A exhibits greatly improved oral exposure of the compound thereby obviating the need to include a surfactant in the oral formulation comprising the Compound 1 Malate Form A.

Example 4C: Compound 1 Malate Exhibits Improved Bioavailability Compared to Compound 1 Free Base in Healthy Patients A Phase 1, 2-part, open-label, single-dose, crossover study was conducted to evaluate the relative bioavailability of Compound 1 Malate vs Compound 1 Free base capsule formulations in Healthy Subjects following oral administration.

Figure 3B:
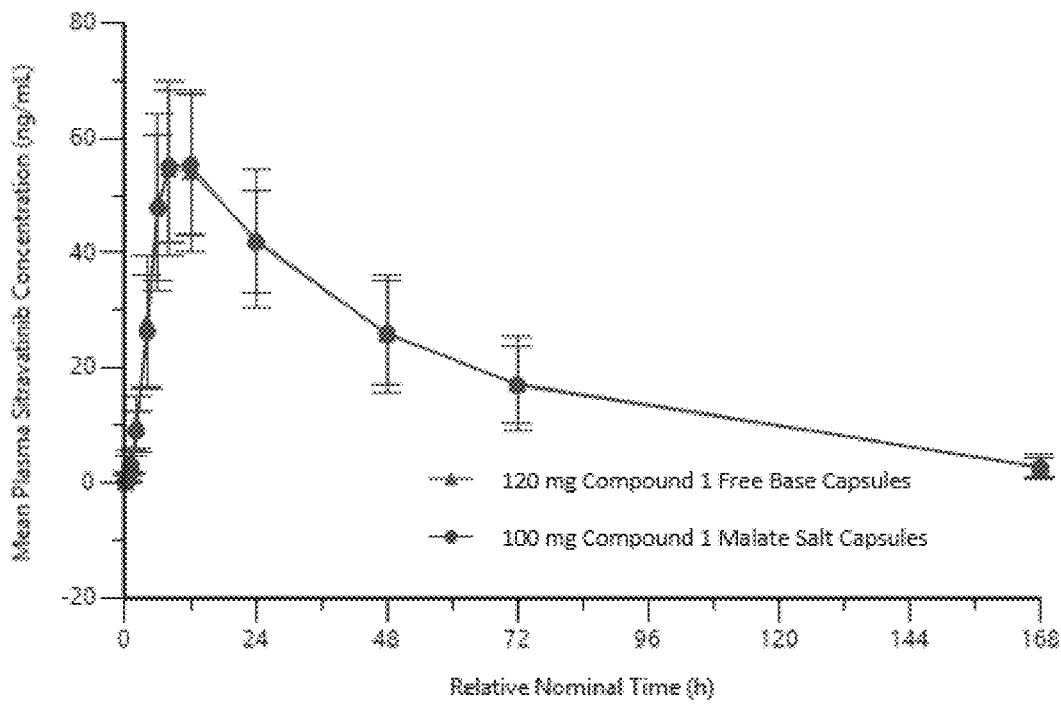
FIGS. 3B and 3C illustrate the mean plasma concentration profile with time in humans for Compound 1 administered as 120 mg free base capsules compared to 100 mg L-malate capsules and corresponding ratio of geometric means and 90% confidence interval for key parameters of the profile, establishing bioequivalence between the two formulations.
Figure 3C:
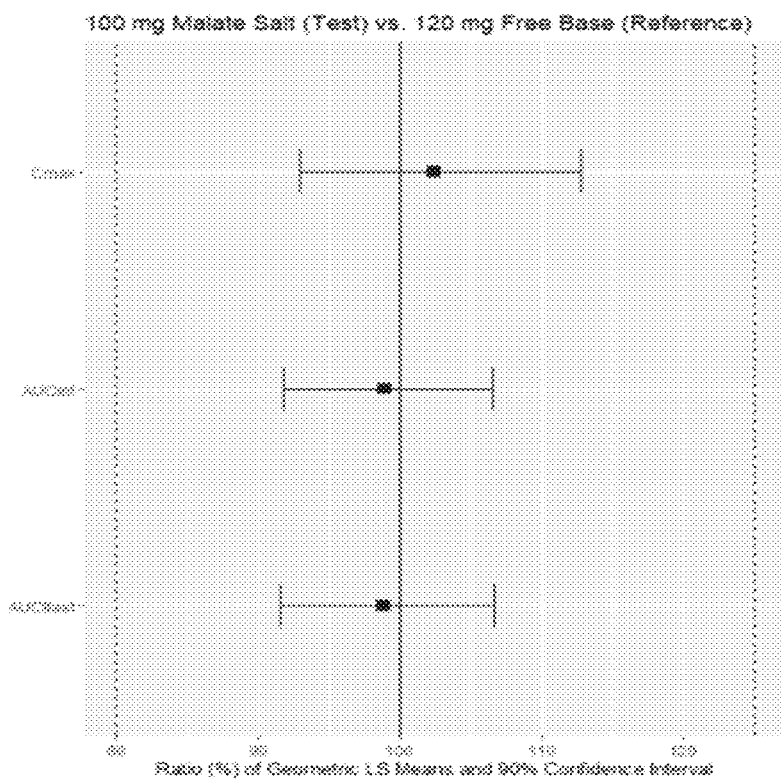

The mean plasma concentration profile with time and relative bioavailability for the two formulations is shown in FIG. 3B and FIG. 3C, demonstrating that bioequivalence was achieved between 100 mg Compound 1 Malate and 120 mg Compound 1 Free base capsule formulations in healthy subjects following oral administration. The results also demonstrate Compound 1 Malate increased absorption and bioavailability compared to Compound 1 Free Base following oral administration.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide malate (1:1).

2. A crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1).

3. A crystalline form of N-(3-fluoro-4-((2-(5-(((2-methoxyethyl)amino)methyl)pyridin-2-yl)thieno[3,2-b]pyridin-7-yl)oxy)phenyl)-N'-(4-fluorophenyl)cyclopropane-1,1-dicarboxamide (S)-2-hydroxysuccinate (1:1), containing 0-3.0 mols of $H_2O$ per mol.

4. The crystalline form according to claim 2, wherein the crystalline form has an X-ray powder diffraction pattern comprising a diffraction peak having ° 2θ angle values in the range of 9.4° to 10.2°.

5. The crystalline form according to claim 2, wherein the crystalline form has an X-ray powder diffraction pattern comprising a diffraction peak having ° 2θ angle value of 9.6±0.2.

6. The crystalline form according to claim 4, wherein the crystalline form has an X-ray powder diffraction pattern furtherly comprising diffraction peaks having ° 2θ angle values of 12.6±0.2.

7. The crystalline form according to claim 6, wherein the crystalline form has an X-ray powder diffraction pattern furtherly comprising diffraction peaks having ° 2θ angle values independently selected from the group consisting of ° 2θ values at 15.3±0.2°, 20.3±0.2°, 21.0±0.2° and 24.1±0.2°.

8. The crystalline form according to claim 6, wherein the crystalline form has an X-ray powder diffraction pattern furtherly comprising diffraction peaks having ° 2θ angle values independently selected from the group consisting of 12.0±0.2°, 15.3±0.2°, 20.3±0.2°, 21.0±0.2°, 22.0±0.2°, 23.2±0.2°, 24.1±0.2°, and 24.2±0.2°.

9. The crystalline form according to claim 6, wherein the crystalline form has an X-ray powder diffraction pattern furtherly comprising diffraction peaks having ° 2θ angle values independently selected from the group consisting of 6.1±0.2°, 8.6±0.2°, 12.0±0.2°, 13.5±0.2° 15.3±0.2°, 16.9±0.2°, 17.4±0.2°, 17.7±0.2°, 18.1±0.2°, 18.4±0.2°, 20.0±0.2°, 20.3±0.2°, 21.0±0.2°, 22.0±0.2°, 22.9±0.2°, 23.2±0.2°, 24.1±0.2°, 24.2±0.2°, 24.8±0.2° and 25.4±0.2°.

10. The crystalline form according to claim 6, wherein the crystalline form has an X-ray powder diffraction pattern furtherly comprising diffraction peaks having ° 2θ angle values independently selected from the group consisting of 6.1±0.2°, 8.6±0.2, 12.0±0.2°, 13.5±0.2° 15.3±0.2°, 16.9±0.2°, 17.4±0.2°, 17.7±0.2°, 18.1±0.2°, 18.4±0.2°, 20.0±0.2°, 20.3±0.2°, 21.0±0.2°, 22.0±0.2°, 22.9±0.2°, 23.2±0.2°, 24.1±0.2°, 24.2±0.2°, 24.8±0.2°, 25.4±0.2°, 25.6±0.2°, 26.2±0.2°, 27.8±0.2°, 28.2±0.2° and 29.1±0.2°.

11. The crystalline form according to claim 4, wherein the crystalline form is designated as Malate Form A.

12. The crystalline form according to claim 11, wherein Malate Form A has an XRPD pattern substantially as shown in FIG. 1A.

13. The crystalline form according to claim 11, wherein Malate Form A is characterized by having a broad endothermic peak in the 50-125° C. range and overlapping endothermic events with a peak maximum at about 171° C. by differential scanning calorimetry (DSC).

14. The crystalline form according to claim 11, wherein Malate Form A has a DSC thermogram substantially as shown in FIG. 1B.

15. The crystalline form according to claim 4, wherein the crystalline form has an XRPD pattern substantially as shown in FIG. 2A(a).

16. A pharmaceutical composition, comprising a therapeutically effective amount of a crystalline form according to claim 2, further comprising at least one pharmaceutically acceptable excipient.

17. A pharmaceutical composition comprising a therapeutically effective amount of a crystalline form according to claim 4, further comprising at least one pharmaceutically acceptable excipient.

18. A method for treating cancer in a subject in need thereof comprising administering to the subject with a therapeutically effective amount of a crystalline form according to claim 2, wherein the cancer is non-small cell lung cancer.

19. A method for treating cancer in a subject in need thereof comprising administering to the subject with a therapeutically effective amount of a crystalline form according to claim 4, wherein the cancer is non-small cell lung cancer.

20. The method according to claim 19, wherein the therapeutically effective amount of the crystalline form is between about 0.01 to 100 mg/kg per day.

21. The method according to claim 19, wherein the therapeutically effective amount of the crystalline form is between about 0.1 to 50 mg/kg per day.

22. The method according to claim 18, wherein the subject is a human.

23. The crystalline form according to claim 4, obtained by the process comprising any one of the following procedures:
   a) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a water-miscible solvent, wherein the solvent is selected from methanol, ethanol, acetone or an aqueous mixture thereof, heating, cooling, or furtherly removing the solvent, to obtain the desired crystalline form;
   b) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) and The desired crystalline form as crystal seed in the water-miscible solvent acetone, heating, adding methanol, cooling, to obtain The desired crystalline form;
   c) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a water-miscible solvent acetone, slurrying, to obtain The desired crystalline form;
   d) suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a water-miscible ethanol, heating, slurrying, cooling, stirring, to obtain The desired crystalline form (shifted).

24. The crystalline form according to claim 4 obtained by the process comprising the steps:
   1) Suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in a mixture acetone and methanol;
   2) Heating the resulting suspension to about 70° C. to generate a clear solution;
   3) Cooling the solution to stimulate crystal formation; and,
   4) removing the organic solvent mixture to obtain The desired crystalline form.

25. The crystalline form according to claim 4 obtained by the process comprising the steps:
   1) Suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) and The desired crystalline form as crystal seed in a water-miscible solvent acetone;
   2) Heating the resulting suspension to about 70° C. to;
   3) Adding a hot water-miscible organic solvent methanol;
   4) Cooling the solution to stimulate crystal formation; and,
   5) removing the acetone-methanol mixture to obtain The desired crystalline form.

26. The crystalline form obtained by the process according to claim 23, wherein the percent volume ratio of acetone to methanol is 59:41 (v/v).

27. The crystalline form according to claim 4 obtained by the process comprising the steps:
   1) Suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide (S)-2-hydroxysuccinate (1:1) in ethanol;
   2) Heating the resulting suspension to about or over 55° C.;
   3) Raising the temperature of the resulting suspension to a temperature of about 65-70° C.; and,
   4) Slowly cooling the suspension to ambient temperature to obtain The desired crystalline form.

28. The crystalline form of claim 4 obtained by the process comprising the steps:
   1) Suspending N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide in ethanol;
   2) Heating the resulting suspension to about 75° C.;
   3) Cooling the temperature of the resulting suspension to a temperature of about 62° C.;
   4) Adding L-malic acid to form the malate salt;
   5) Slowly cooling the suspension to a temperature of about 25° C. to initiate a crystalline form; and,
   6) Cooling the suspension to a temperature of about 0° C. to obtain The desired crystalline form.

* * * * *